(12) United States Patent
Bharti et al.

(10) Patent No.: US 11,458,225 B2
(45) Date of Patent: Oct. 4, 2022

(54) 3D VASCULARIZED HUMAN OCULAR TISSUE FOR CELL THERAPY AND DRUG DISCOVERY

(71) Applicant: THE UNITED STATES OF AMERICA, as represented by the Secretary, Department of Health and Human Services, Bethesda, MD (US)

(72) Inventors: Kapil Bharti, Potomac, MS (US); Min Jae Song, Olney, MD (US); Russell Louis Quinn, Washington, DC (US)

(73) Assignee: THE UNITED STATES OF AMERICA, as represented by the Secretary, Department of Health and Human Services, Bethesda, MD (US)

( * ) Notice: Subject to any disclaimer, the term of this patent is extended or adjusted under 35 U.S.C. 154(b) by 627 days.

(21) Appl. No.: 16/347,939

(22) PCT Filed: Nov. 8, 2017

(86) PCT No.: PCT/US2017/060666
§ 371 (c)(1),
(2) Date: May 7, 2019

(87) PCT Pub. No.: WO2018/089515
PCT Pub. Date: May 17, 2018

(65) Prior Publication Data
US 2019/0290803 A1    Sep. 26, 2019

Related U.S. Application Data

(60) Provisional application No. 62/419,835, filed on Nov. 9, 2016.

(51) Int. Cl.
| | | |
|---|---|---|
| *A61L 27/38* | (2006.01) | |
| *A61L 27/18* | (2006.01) | |
| *A61L 27/24* | (2006.01) | |
| *A61L 27/52* | (2006.01) | |
| *C12N 5/079* | (2010.01) | |
| *C12N 5/077* | (2010.01) | |
| *C12N 5/071* | (2010.01) | |
| *A61L 27/58* | (2006.01) | |
| *A61L 27/56* | (2006.01) | |

(52) U.S. Cl.
CPC ........... *A61L 27/3813* (2013.01); *A61L 27/18* (2013.01); *A61L 27/24* (2013.01); *A61L 27/3808* (2013.01); *A61L 27/3891* (2013.01); *A61L 27/52* (2013.01); *C12N 5/069* (2013.01); *C12N 5/0621* (2013.01); *C12N 5/0656* (2013.01); *A61L 27/56* (2013.01); *A61L 27/58* (2013.01); *A61L 2430/16* (2013.01); *C12N 2500/38* (2013.01); *C12N 2501/105* (2013.01); *C12N 2501/11* (2013.01); *C12N 2501/115* (2013.01); *C12N 2501/165* (2013.01); *C12N 2501/17* (2013.01); *C12N 2501/39* (2013.01); *C12N 2501/90* (2013.01); *C12N 2533/40* (2013.01); *C12N 2533/50* (2013.01); *C12N 2533/54* (2013.01)

(58) Field of Classification Search
None
See application file for complete search history.

(56) References Cited

U.S. PATENT DOCUMENTS

| | | |
|---|---|---|
| 2011/0000430 A1 | 1/2011 | Tao et al. |
| 2013/0004469 A1 | 1/2013 | Glazier et al. |
| 2015/0250828 A1 | 9/2015 | Kamao |
| 2016/0122723 A1 | 5/2016 | Retting et al. |

FOREIGN PATENT DOCUMENTS

| | | |
|---|---|---|
| EP | 2 889 374 A1 | 7/2015 |
| WO | WO 2012/177968 A1 | 12/2012 |
| WO | WO 2014/030749 A1 | 2/2014 |
| WO | WO 2014/121077 | 8/2014 |
| WO | WO 2016/007852 A1 | 1/2016 |
| WO | WO 2016/049345 A1 | 3/2016 |
| WO | WO 2017/044483 | 3/2017 |
| WO | WO 2018/144515 | 8/2018 |

OTHER PUBLICATIONS

Chen et al., "Layer-by-Layer Bioprinting of Stem Cells for Retinal Tissue Regeneration," University of California, San Diego, 14 pages (Dec. 1, 2016).
International Search Report and Written Opinion mailed in International Application No. PCT/US2017/060666, dated Apr. 9, 2018, 15 pages.

*Primary Examiner* — Allison M Fox
(74) *Attorney, Agent, or Firm* — Klarquist Sparkman, LLP

(57) ABSTRACT

Methods are disclosed for fabricating a three-dimensional engineered blood retinal barrier (BRB) comprising a choroid and retinal pigment epithelial cells. The methods include the use of bioprinting. Also disclosed is a three-dimensional engineered BRB, and its use. Methods are also disclosed for using the three-dimensional engineered BRB, such as for the treatment of retinal degeneration in a subject or screening. A three-dimensional printing insert that is adapted for bioprinting on a culture substrate sheet that is securely retained within and exposed through a printing frame is also disclosed.

30 Claims, 29 Drawing Sheets

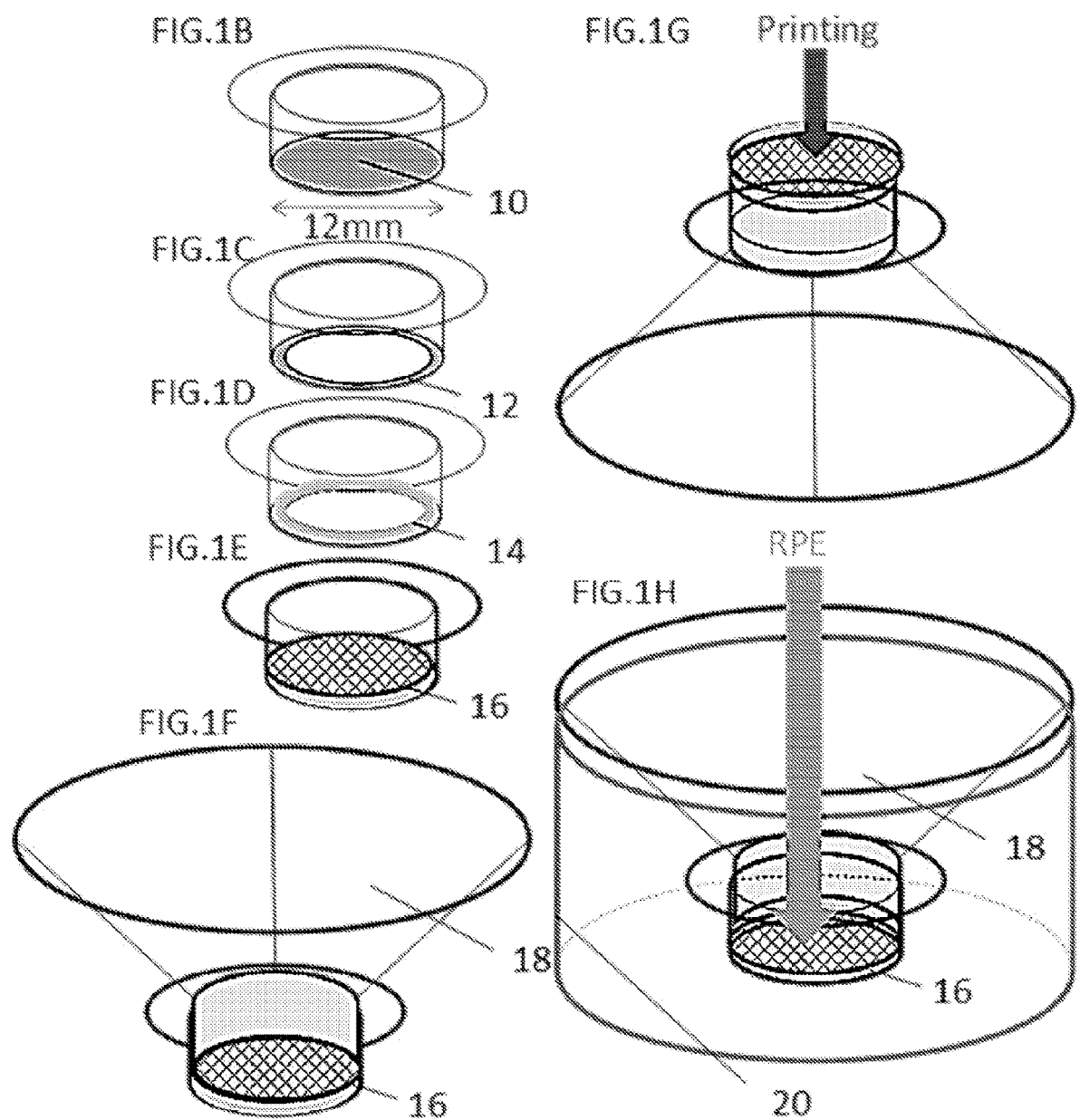

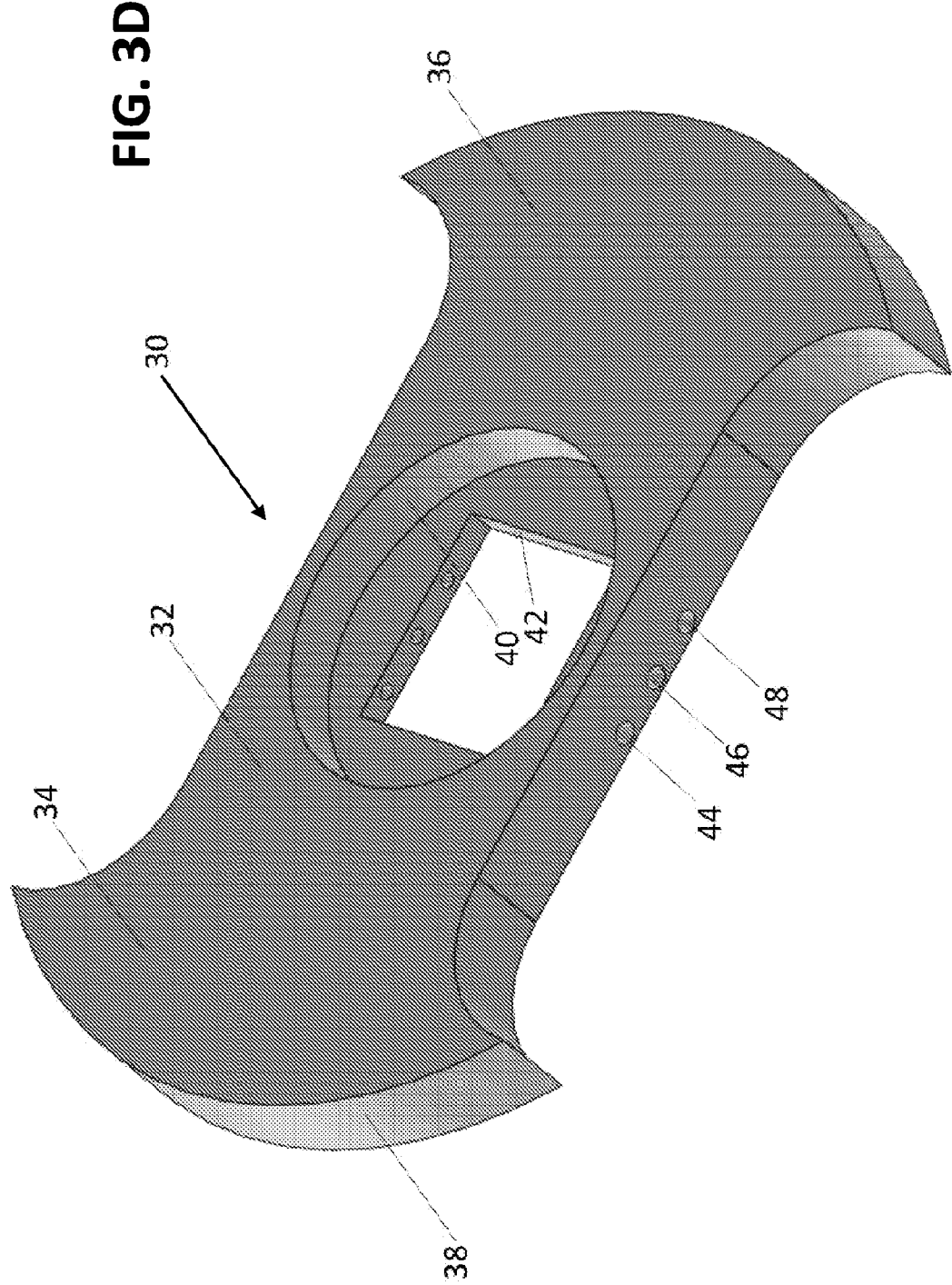

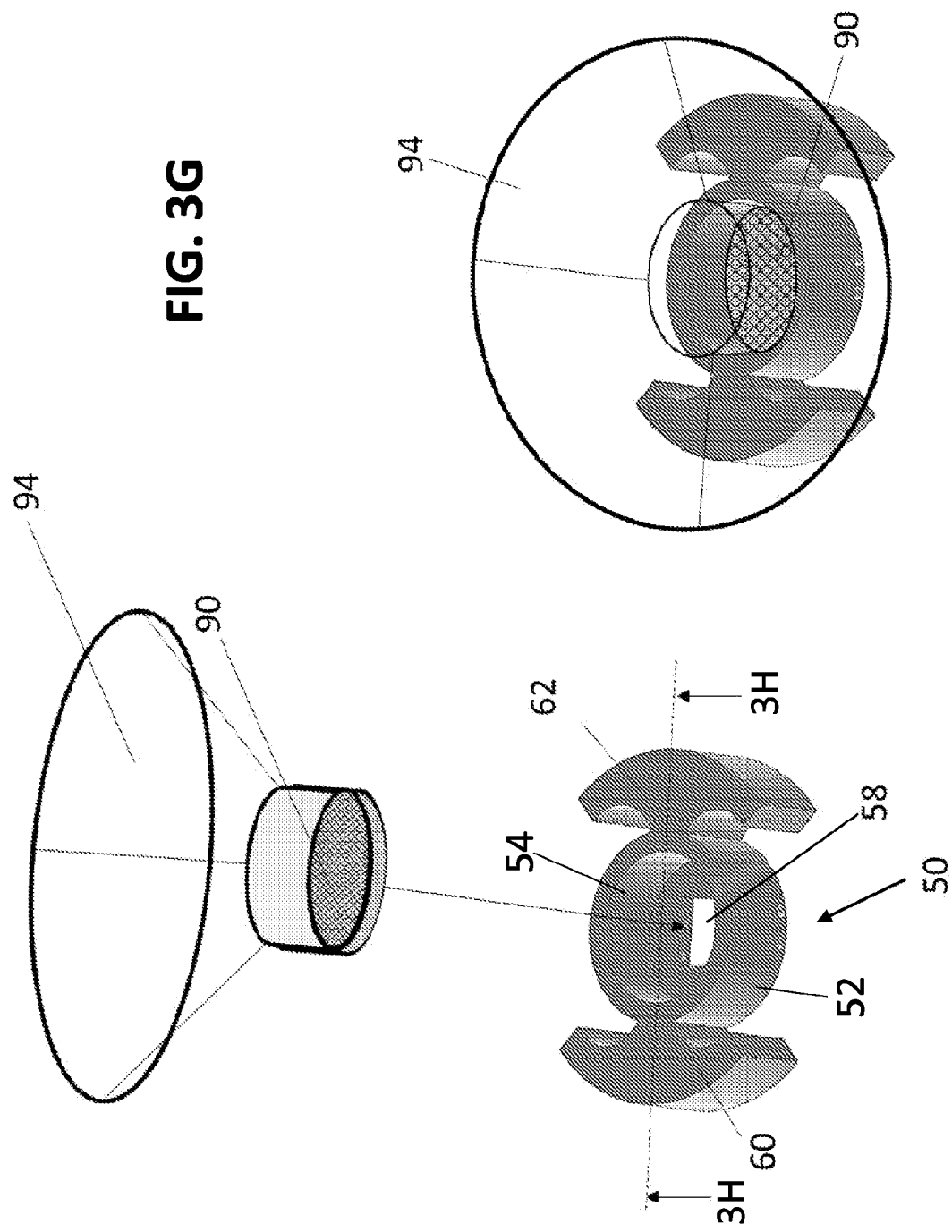

|  | Group1 | Group2 | Group 3 | Group 4 |
|---|---|---|---|---|
| Day 0 (Printing) | +EGF +ANG-1 High VEGF | -EGF +ANG-1 High VEGF | +EGF -ANG-1 High VEGF | -EGF -ANG-1 High VEGF |
| Day 3 | +EGF +ANG-1 Low VEGF | -EGF +ANG-1 Low VEGF | +EGF -ANG-1 Low VEGF | -EGF -ANG-1 Low VEGF |
| Day 5 |  | +EGF +ANG-1 Low VEGF | +EGF +ANG-1 Low VEGF | +EGF +ANG-1 Low VEGF |
| Day 9 | Fixation | | | |

FIG. 5C
Group 1 (Day 9)
GFP expressing endothelial cells
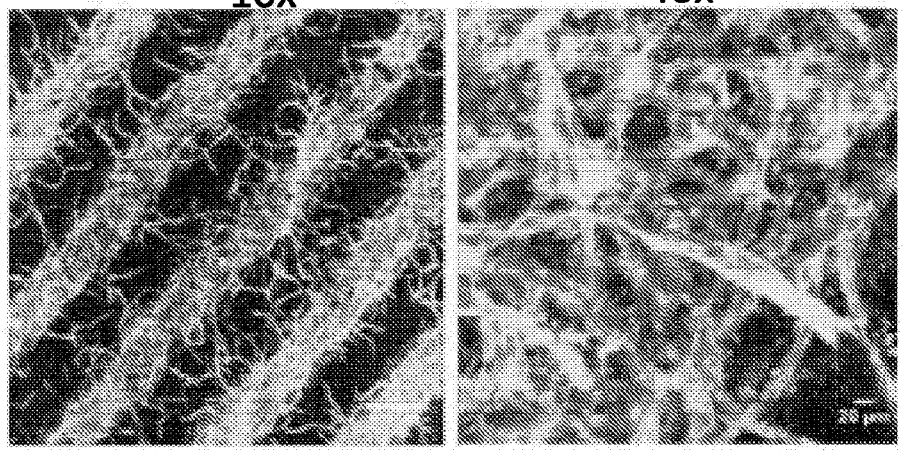
Non-fluorescent endothelial cells
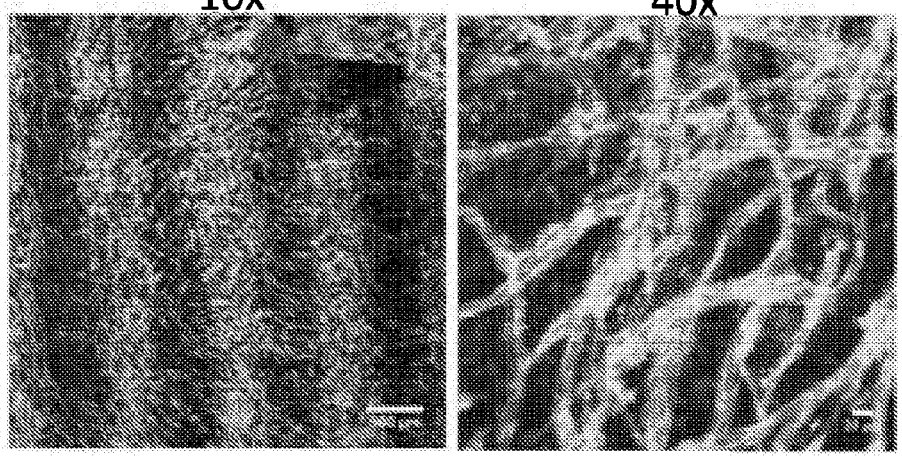
Human iPSC derived endothelial cells
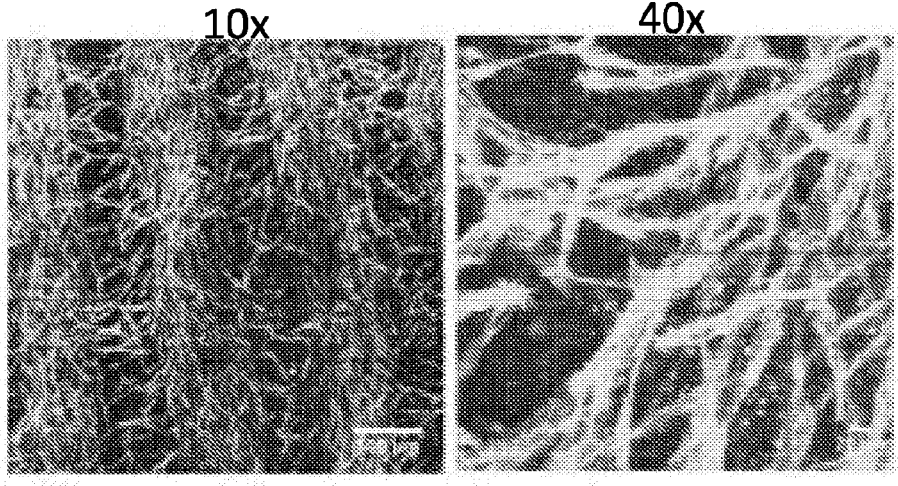

FIG. 6A　　　　　　　　FIG. 6C
VEGF　GFP expressing endothelial cells (15 days)　　human iPSC derived endothelial cells (9 days)
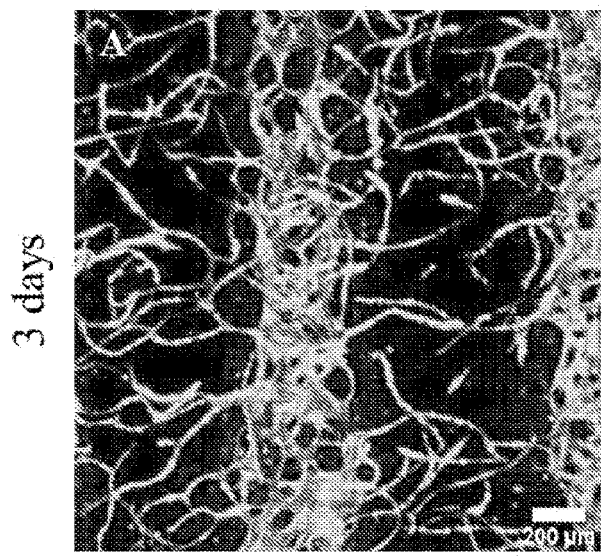
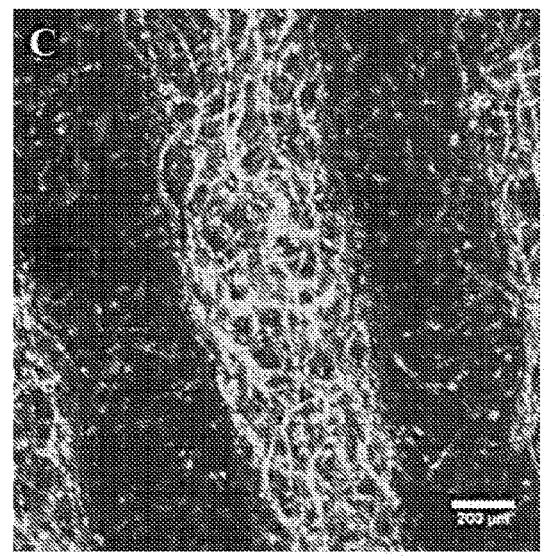
3 days
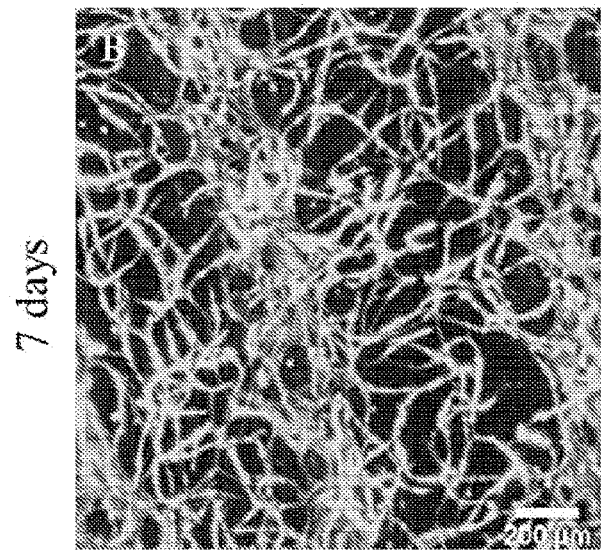
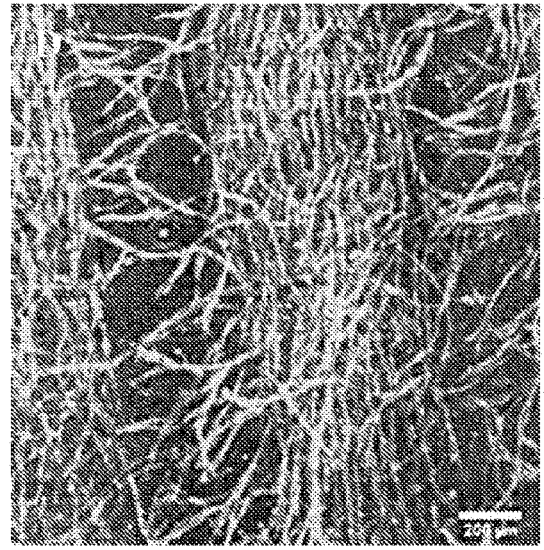
7 days
FIG. 6B　　　　　　　　FIG. 6D

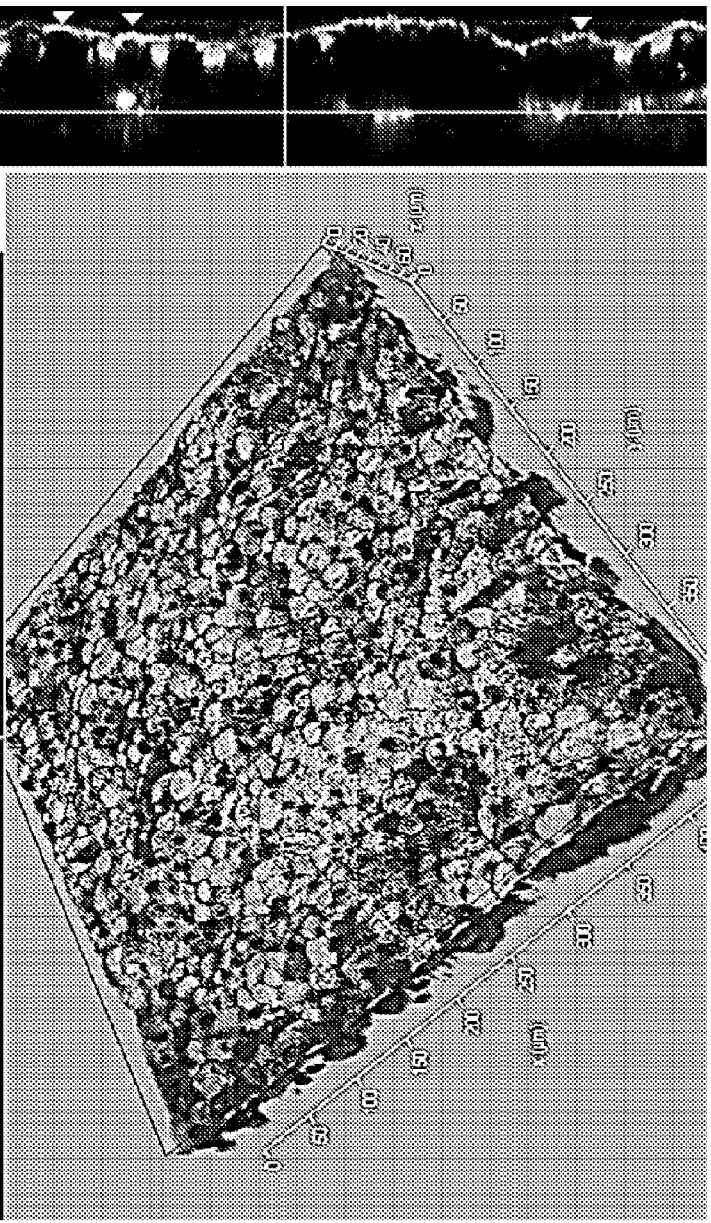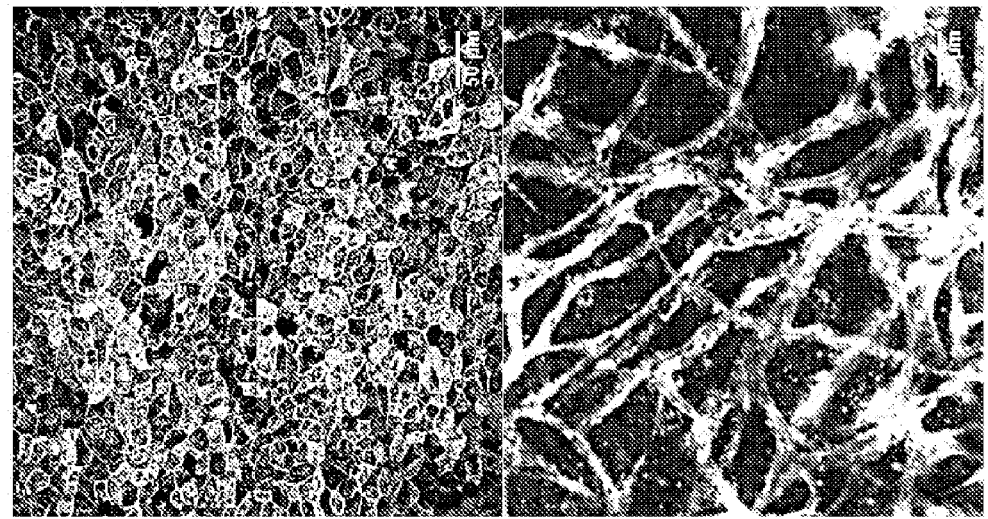
FIG. 15A
FIG. 15B
FIG. 15C

E-cadherin

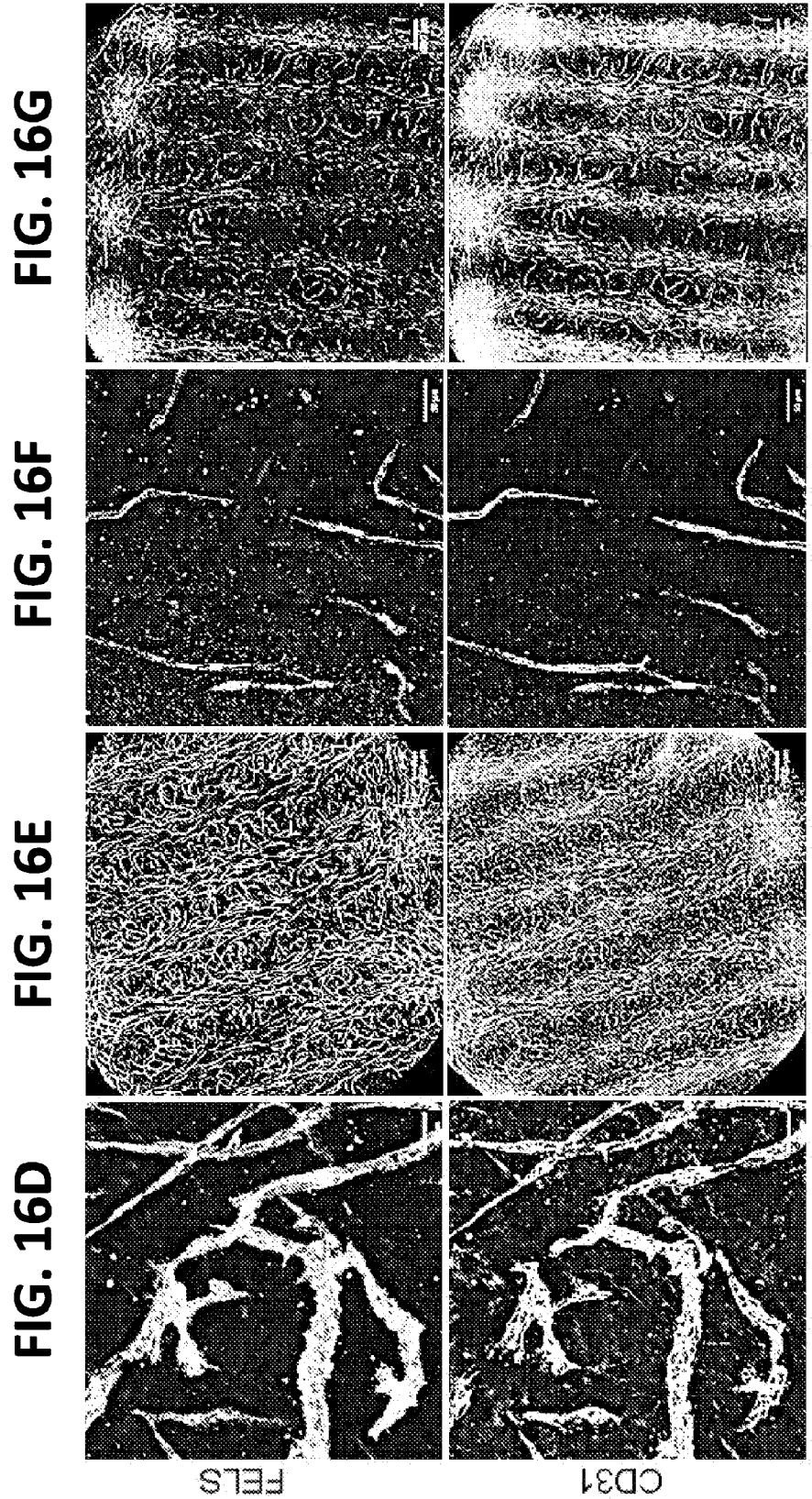

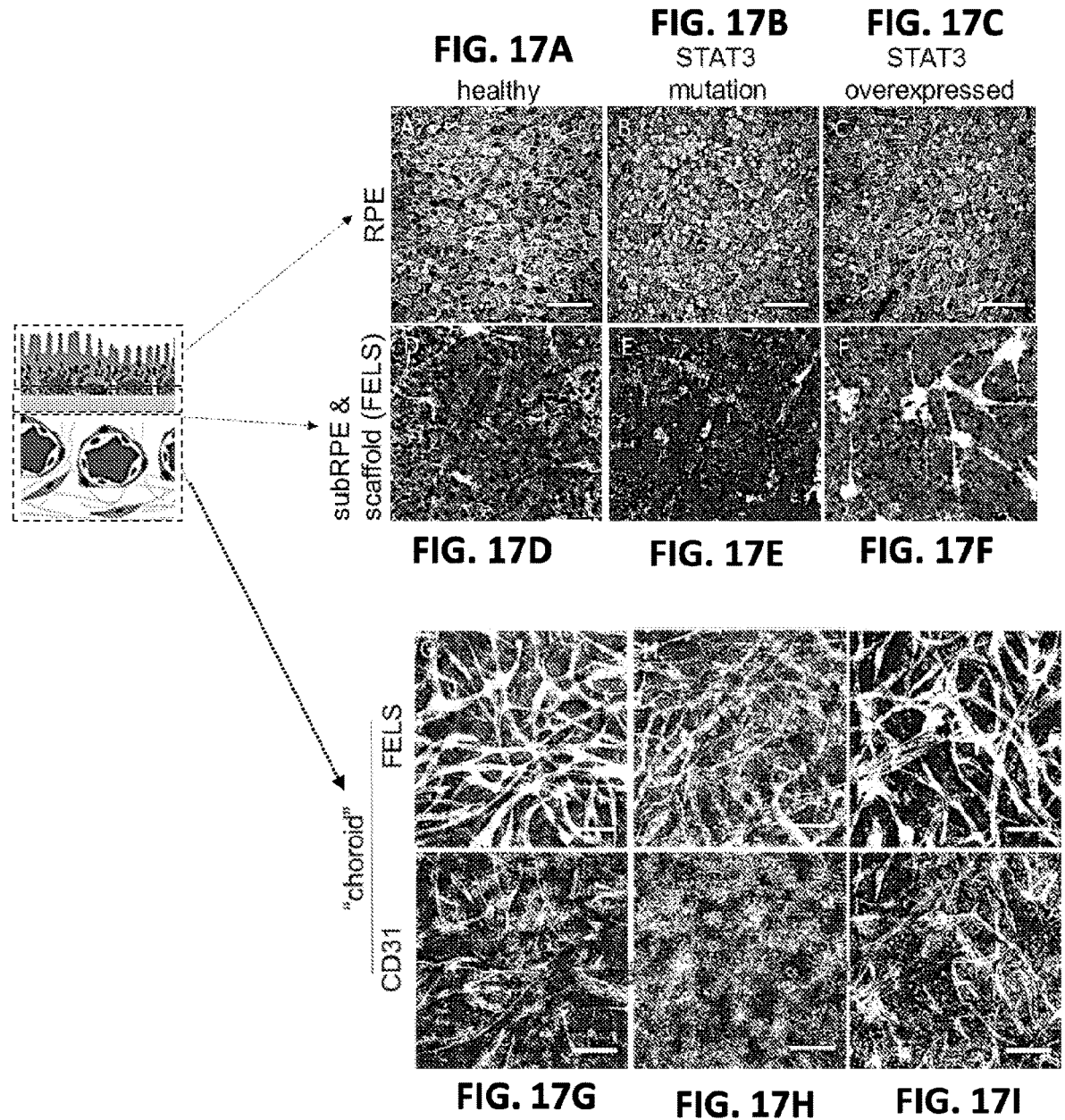

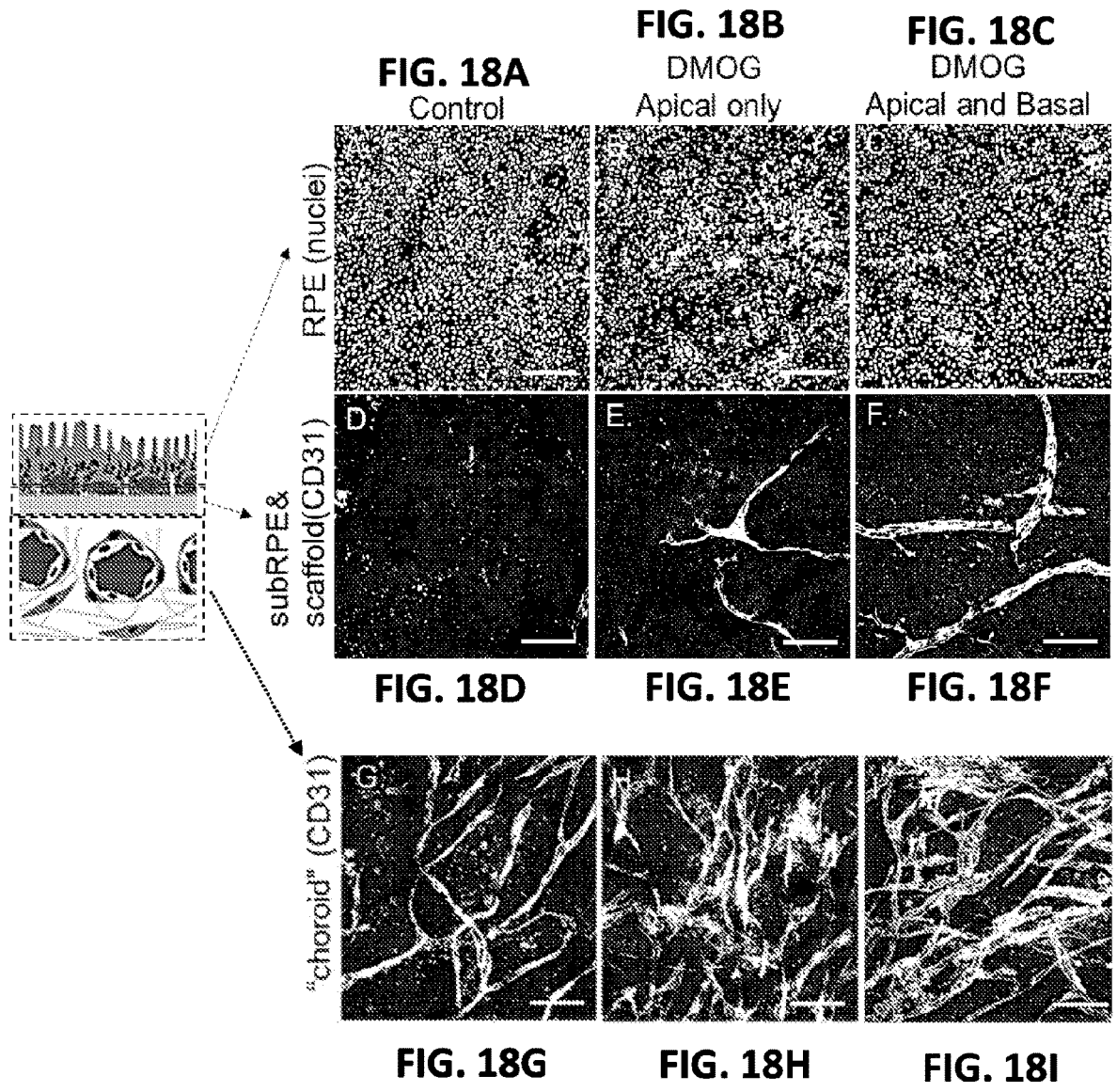

3D VASCULARIZED HUMAN OCULAR TISSUE FOR CELL THERAPY AND DRUG DISCOVERY

CROSS REFERENCE TO RELATED APPLICATION

This is a § 371 U.S. national stage of International Application No. PCT/US2017/060666, filed Nov. 8, 2017, which was published in English under PCT Article 21(2), and which claims the benefit of U.S. Provisional Application No. 62/419,835, filed Nov. 9, 2016, which is incorporated by reference herein in its entirety.

STATEMENT OF GOVERNMENT SUPPORT

This invention was made with government support under project no. Z01 #: EY000532-04 awarded by the National Institutes of Health, the National Eye Institute. The government has certain rights in the invention.

FIELD OF THE DISCLOSURE

This disclosure relates to the field of artificial organs, specifically to the use of three-dimensional (3D) bioprinting to produce a three-dimensional engineered outer blood retinal barrier (BRB) comprising a choroid and retinal pigmented epithelial cells.

BACKGROUND

The retina is a layer of specialized light sensitive neural tissue located at the inner surface of the eye of vertebrates. Light reaching the retina after passing through the cornea, lens and vitreous humor is transformed into chemical and electrical events that trigger nerve impulses. The cells that are responsible for transduction, the process for converting light into these nerve impulses are specialized neurons called photoreceptor cells.

Many ophthalmic diseases, such as (age-related) macular degeneration, macular dystrophies such as Stargardt's and Stargardt's-like disease, Best disease (vitelliform macular dystrophy), and adult vitelliform dystrophy or subtypes of retinitis pigmentosa, are associated with a degeneration or deterioration of the retina itself. It has been demonstrated in animal models that photoreceptor rescue and preservation of visual function could be achieved by subretinal transplantation of retinal pigment epithelial cells (Coffey et al. Nat. Neurosci. 2002:5, 53-56; Lin et al. Curr. Eye Res. 1996:15, 1069-1077; Little et al. Invest. Ophthalmol. Vis. Sci. 1996: 37, 204-211; Sauve et al. Neuroscience 2002:114, 389-401). There is a need to find ways to produce an engineered vascularized outer blood retinal barrier (BRB) for transplantation, which can be used for the evaluation of potential therapeutic agents and for the treatment of retinal degenerative diseases and injuries.

SUMMARY OF THE DISCLOSURE

In some embodiments, a method is disclosed for fabricating a three-dimensional engineered blood retinal barrier (BRB) comprising a choroid and retinal pigment epithelial cells. The method includes a. depositing a first bio-ink comprising endothelial cells, a hydrogel and a first medium, onto a biocompatible scaffold having first and second surfaces, such that the hydrogel containing endothelial cells adhere to the first surface of the biocompatible scaffold;

b. maturing the deposited first bio-ink on the first surface in a second medium for at least four days to allow the endothelial cells to form vessels;

c. depositing retinal pigment epithelial cells in a third medium to form a single cell layer on the second surface of the biocompatible scaffold, such that the biocompatible scaffold is between the endothelial cells and the retinal pigment epithelial cells; and d. culturing the deposited retinal pigment epithelial cells in the third medium so that they proliferate and mature.

Optionally, the first bio-ink can also include fibroblasts and pericytes.

The three-dimensional engineered BRB made by the method provides an artificial choroid on the first surface and an artificial retinal pigment epithelium on the second surface.

In additional embodiments, methods are disclosed for treating a subject with acute macular or retinal degeneration, by transplanting the engineered BRB that comprises the choroid and retinal pigment epithelial cells into the eye of the subject.

In some embodiments, disclosed is a three-dimensional, engineered ocular tissue model.

The three-dimensional, engineered ocular tissue model includes a three-dimensional, engineered outer blood retinal barrier (BRB), wherein the engineered outer retinal barrier includes a first layer comprising choroidal vasculature and a second layer including a plurality of retinal pigment epithelial cells. The choroidal vasculature includes a first bio-ink, wherein first bio-ink includes a plurality of endothelial cells, and optionally fibroblasts and/or pericytes. The three-dimensional, engineered ocular tissue model can be used as a model of wild-type ocular tissue, or can be a model of an ocular disease or a potential tissue therapy or used to test a potential gene therapy.

In further embodiments, methods are provided for determining the effect of a test agent using the disclosed three-dimensional engineered BRB comprising a choroid and retinal pigment epithelial cells. The methods include contacting the three-dimensional engineered BRB with the test agent, and evaluating a phenotype of cells within the choroid with retinal pigment epithelial cells, and/or evaluating a three-dimensional structure of the choroid with retinal pigment epithelial cells. A change in the phenotype of the cells or a change in the three-dimensional structure indicates that the agent has a biological effect, such as a biological test activity. The test agent can be of use for the treatment of an ocular disease or can be used in in situ gene therapy.

More specific non-limiting examples of methods for fabricating a three-dimensional BRB are disclosed. In some specific non-limiting examples, the methods include:

a. providing a first bio-ink including endothelial cells, fibroblasts and pericytes in a collagen or fibrinogen hydrogel and a first medium including thrombin, vascular endothelial grown factor, epithelial growth factor (EGF), fibroblast growth factor (FGF), insulin-like growth factor (IGF), ascorbic acid, hydrocortisone, heparin sulfate, angiopoietin-1, and aprotinin, and depositing the first bio-ink onto a biocompatible oxygen plasma treated lactide/glycolide polymer, such as a poly (D, L-lactide co-glycolide) PDGLA scaffold, such that the hydrogel containing the endothelial cells, fibroblasts and pericytes adhere to a first surface of the biocompatible scaffold;

b. maturing the deposited first bio-ink in a second medium on the first surface, wherein the second medium includes an effective amount of vascular endothelial growth factor, EGF, FGF, IGF, ascorbic acid, hydrocortisone, heparin sulfate, and angiopoietin-1 and aprotinin, in the absence of thrombin, for at least four days to allow the endothelial cells to form vessels;

c. depositing retinal pigment epithelial cells in a third medium to form a layer on a second surface of the biocompatible scaffold, wherein the first and the second surfaces of the biocompatible scaffold are opposite surfaces, such that biocompatible scaffold is between the endothelial cells and the retinal pigment epithelial cells, wherein the second surface is coated with vitronectin, and the third medium includes an effective amount of taurine-hydrocortisone-triiodo-thyronin, hydrocortisone, triiodo-thyronin, fetal bovine serum;

d. culturing the deposited retinal pigment epithelial cells on the second surface in the third medium that includes the effective amount of taurine-hydrocortisone-triiodo-thyronin, hydrocortisone, triiodo-thyronin, fetal bovine serum so that the deposited retinal pigment epithelial cells proliferate and mature; and e. culturing the endothelial cells, fibroblasts and the pericytes in a fourth medium including an effective amount of vascular endothelial grown factor, and optionally one, more, or all of epidermal growth factor (EGF), fibroblast growth factor (FGF), insulin like growth factor (IGF), ascorbic acid, hydrocortisone, heparin sulfate, and aprotinin, wherein the fourth medium does not include thrombin and angiopoietin-1;

f. culturing the endothelial cells, fibroblasts and the pericytes in a fifth medium including an effective amount of vascular endothelial grown factor, and optionally one, more, or all of EGF, FGF, IGF, ascorbic acid, hydrocortisone, and heparin sulfate wherein the fifth medium does not include thrombin, angiopoietin-1, and aprotinin; and g. culturing the retinal pigment epithelial cells in a sixth medium including an effective amount of prostaglandin E2 added to the third medium, wherein the cultured endothelial cells form an artificial choroid and the cultured retinal pigment epithelium cells form an artificial retinal pigment epithelium of the engineered BRB The foregoing and other features and advantages of the invention will become more apparent from the following detailed description of several embodiments which proceeds with reference to the accompanying figures.

BRIEF DESCRIPTION OF THE FIGURES

FIGS. 1A-1H. FIG. 1A is a schematic illustration of three-dimensional (3D) bioprinting of blood retina barrier (BRB) using human iPSC derived endothelial cells and RPE cells. (A) Graphic abstract of 3D engineered tissue for modeling dry and wet-form of age related macular degeneration (AMD). Mixture of inducted pluripotent stem cell (iPSC)-derived endothelial cells, pericytes, and fibroblasts in a fibrin based gel is printed on a poly(lactic-co-glycolic acid (PLGA) electrospun (or other) scaffold. iPSC derived retina pigment epithelial (RPE) cell monolayer forms on the other side of scaffold. This RPE-scaffold-"choroid" becomes a basic prototype to develop a disease model or a tissue therapy. Defined printing geometry distinguishes angiogenesis from vasculogenesis and it facilitates quantification of angiogenesis. A prototype of engineered BRB includes a biodegradable polymer scaffold between a retina pigment epithelial cells (RPE) cell monolayer and printed choroid. FIGS. 1B-1H schematically illustrate steps in an example of a bioprinting method in which the scaffold is placed inside an insert (FIG. 1E) that is attached to a funnel-shaped holder (FIG. 1F) that is inverted for bioprinting (FIG. 1G), then reinverted with the insert placed in a culture chamber (FIG. 1H) with the insert suspended by the holder from the rim of the culture chamber.

FIGS. 3A-3H depict the disclosed devices and methods for bioprinting. FIG. 3A shows three-dimensional (3D) printed transwell designs based on a multiwell platform using a 6 well and 12 well microfluidics approach. PLA mixed with glass/carbon is used to make the insert to minimize shrinking and enhance biocompatibility. The printed wells are sterilized by oxygen plasma and submerging in 70% ethyl alcohol. FIG. 3B shows a water drop (arrow) test on Teflon with oxygen plasma treatment for 30 minutes which illustrates that the treated scaffold surface is changed from hydrophobic to hydrophilic to enable printing of bio-ink on it. FIG. 3C illustrates bioprinting on the surface of a PDLGA scaffold retained in a frame of the inverted insert. FIGS. 3D-3F are enlarged views of different embodiments of the insert, and FIG. 3G schematically illustrates how the insert would be used in a culture well. FIG. 3H is an enlarged cross-sectional view taken along section line 3H-3H in FIG. 3G. FIG. 3H shows an assembled printing insert wedged into the bottom of a culture well. The scaffold sheet is positioned inside the central collar of the insert, and the scaffold sheet is exposed through a square printing frame formed by a recess in the bottom wall of the insert body. A cylindrical portion of a funnel-shaped culture well holder is inserted into a central cylindrical recess of the insert to secure the scaffold sheet in the printing frame. The holder is shown suspended from the walls of the culture well by a peripheral lip of the funnel.

FIGS. 5A-5C illustrate optimization of media components using three types of endothelial cells: GFP positive endothelial cells, Non fluorescent endothelial cells, and iPSC-derived endothelial cells. A. Effects of endothelial growth factor (EGF) and angiopoietin (ANG)-1 on tube formation. Scale bar shows 500 μm. B. Time frame of changing media components. C. Tube formation is confirmed in group 1 media (Day 9).

FIGS. 6A-6D show printed tissue response to vascular endothelial growth factor (VEGF) treatment. Printed tissue with (A, B) GFP endothelial cells and (C, D) human iPSC derived endothelial cells with 3 days (A, C), 7 days (B, D)

of VEGF treatment. Green indicates GFP/CD31, and blue indicates nuclei. Scale bar is 200 μm.

Figure 7:
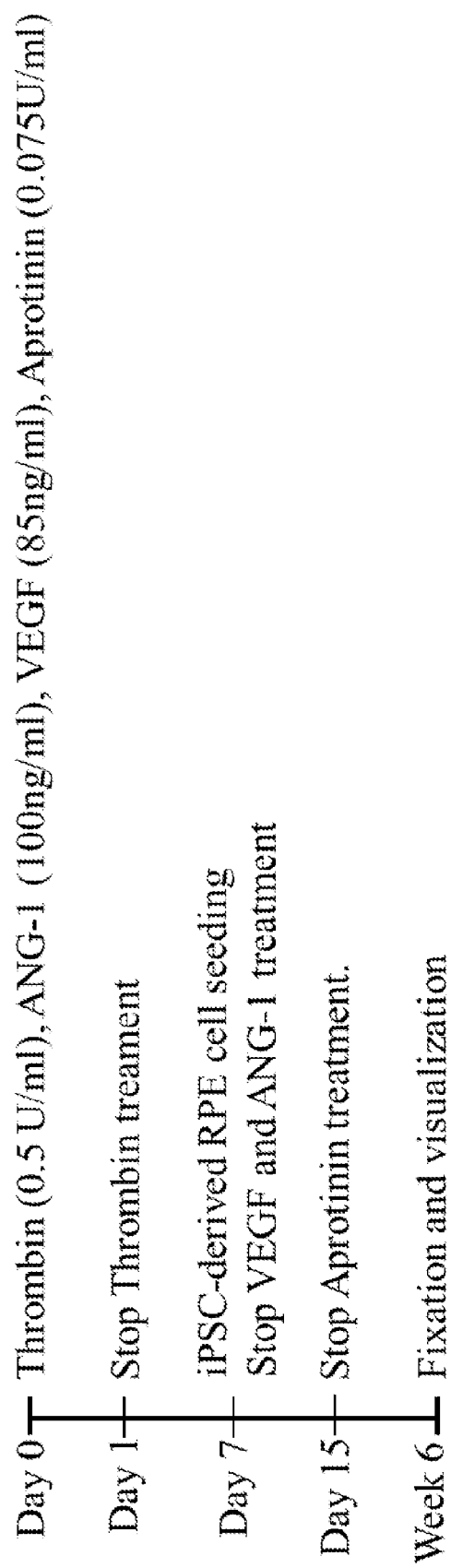

FIG. 7 schematically depicts a time frame of tissue culture after bioprinting. Endothelial cells ($5.5 \times 10^6$ cells/ml), Fibroblasts ($10^7$ cells/ml), and pericytes ($5 \times 10^5$ cells/ml) in fibrin gel (2.5 mg/ml) are printed on scaffolds. 24 hour treatment of thrombin polymerizes fibrinogen. VEGF is important for tube formation and ANG-1 enhances vessel stability. Aprotinin minimizes degradation of fibrin gel.

Figure 8:
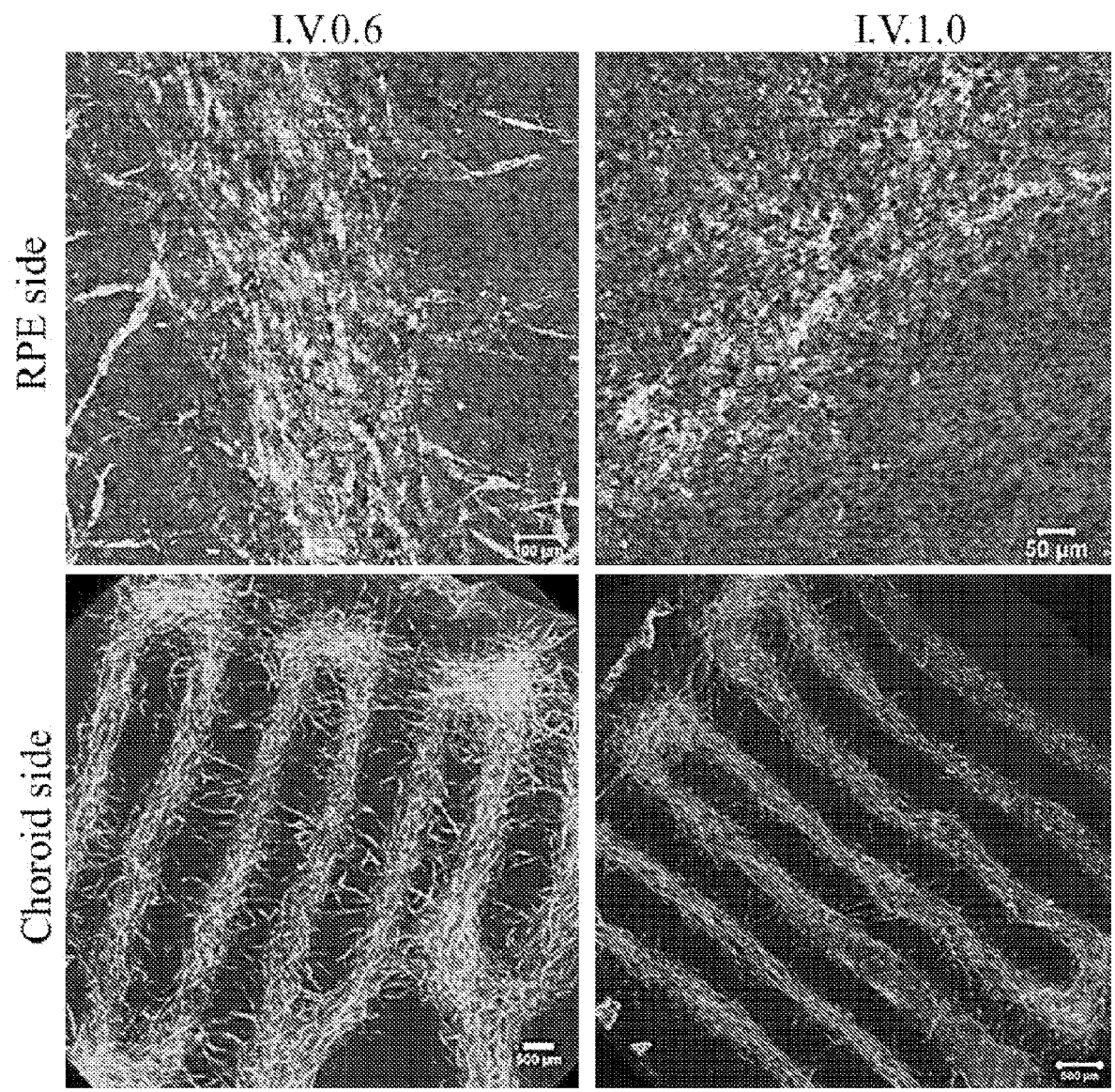

FIG. 8 is a photomicrograph showing bioprinting of choroid and iPSC derived RPE cell seeding on PDLGA scaffolds of I.V.0.6 and I.V. 1.0. Printed tissues were fixed with 4% paraformaldehyde at week 7~8 after printing. Tissues were immunostained with ZO-1 (Tight junction, red), CD31 (endothelial cell/vasculature marker, green), and Hoescht (nulcei, blue). Images were taken by confocal microscope (Zeiss 710).

Figure 9:
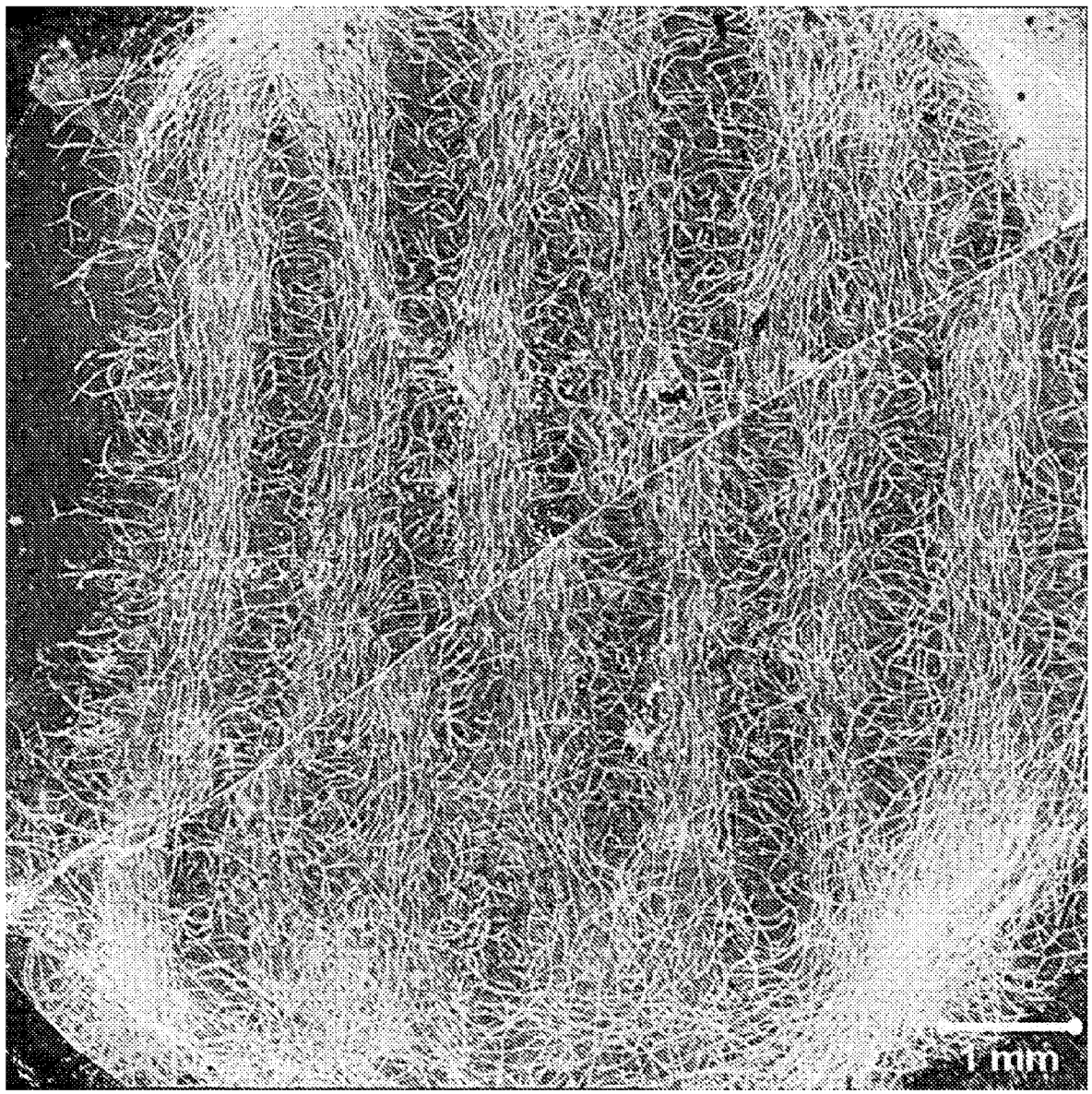

FIG. 9 is a photomicrograph showing 3D bioprinted microvessel seen on the surface one of a scaffold. Microvessels grow in between bioprinted vessels.

Figure 10:
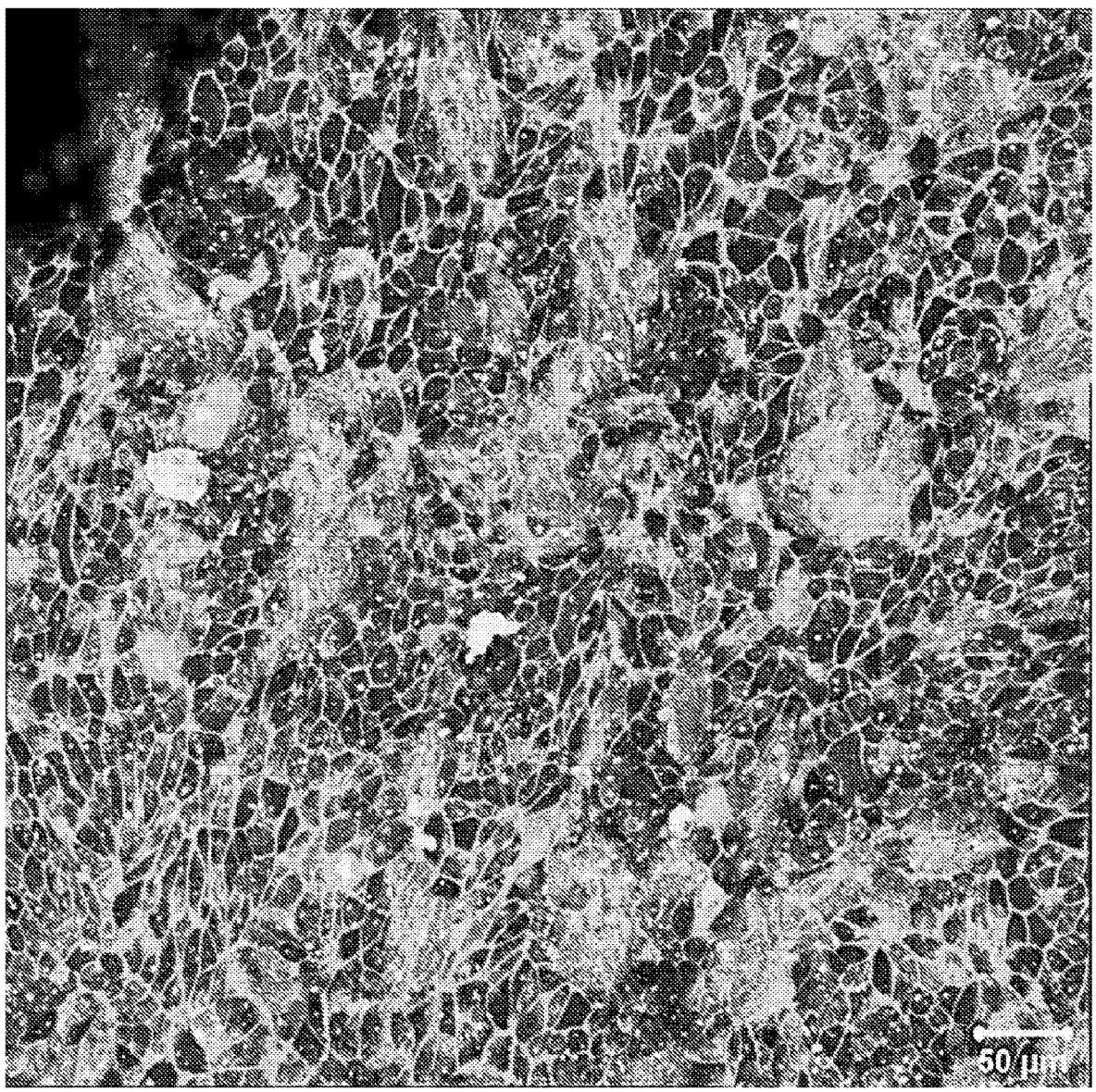

FIG. 10 is a photomicrograph showing iPSC-RPE on surface two of the scaffold.

Figure 11A:
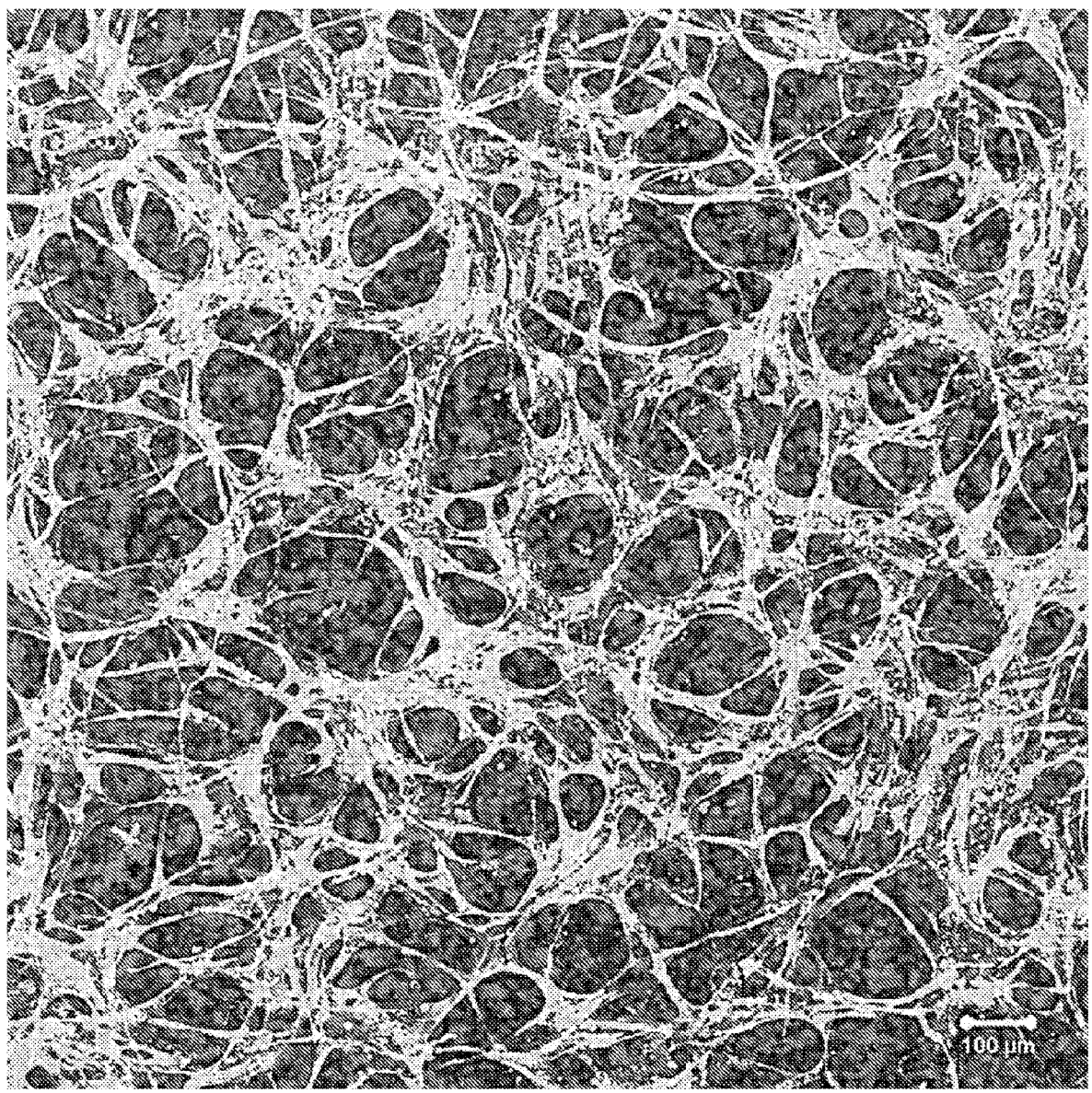
Figure 11B:
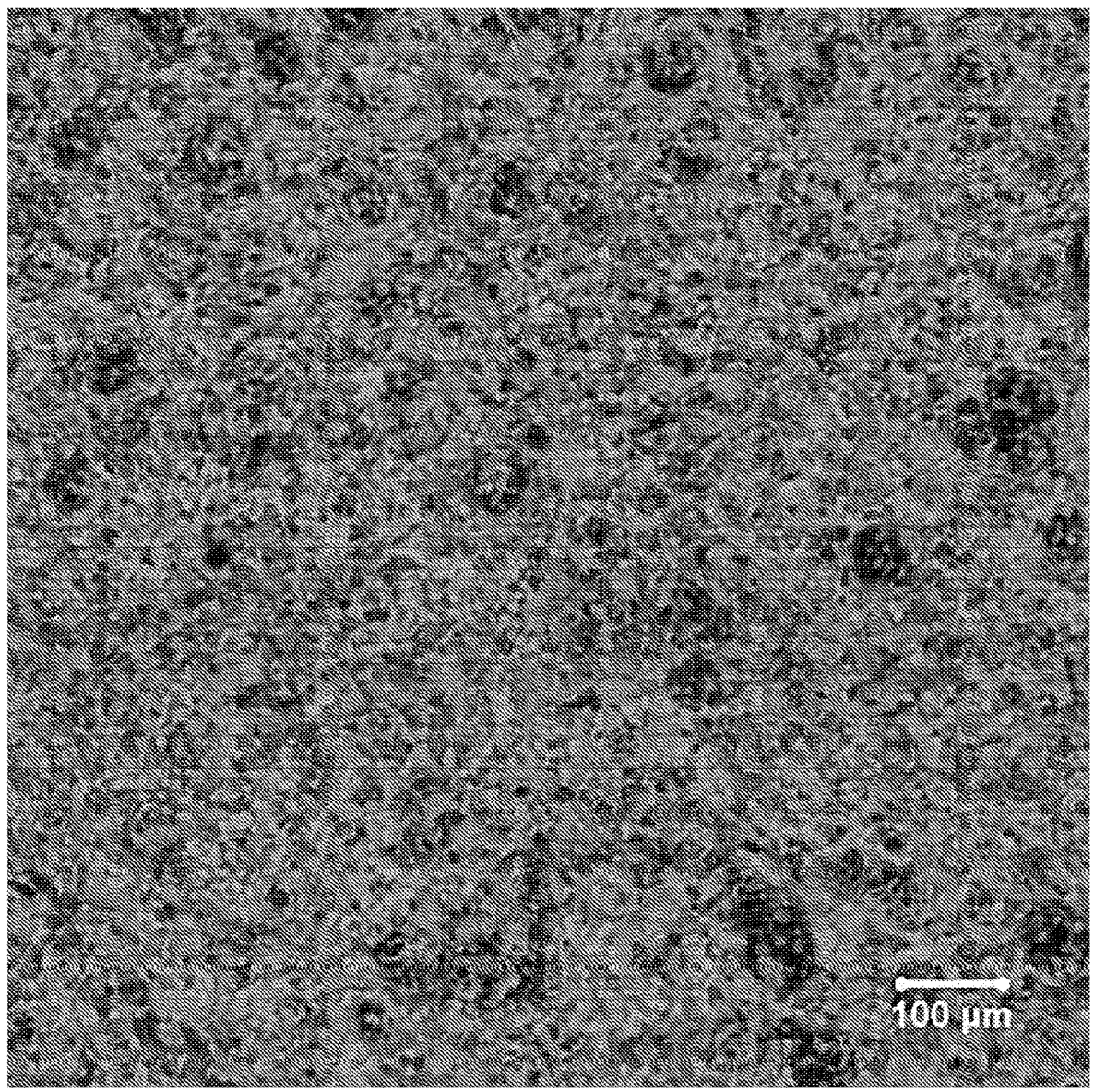

FIGS. 11A-11B are photomicrographs illustrating another example (A) of 3D bioprinted microvessel seen on surface one and iPSC-derived RPE on the opposite side of the scaffold; and (B) iPSC-RPE on 3D printed tissue from surface two.

Figure 12:
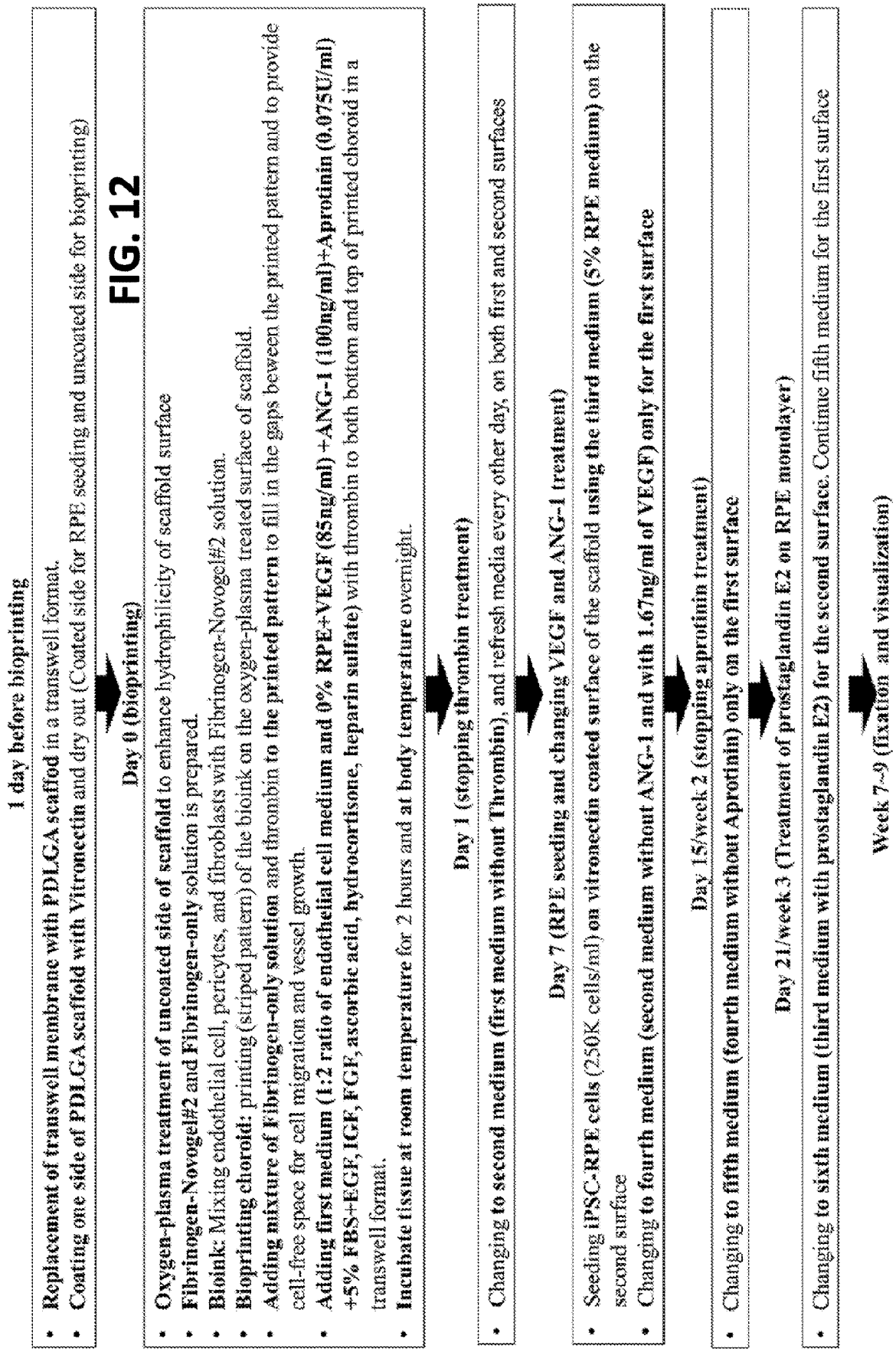

FIG. 12 is a flow chart showing an exemplary culturing method for making the BRB.

Figure 13A:
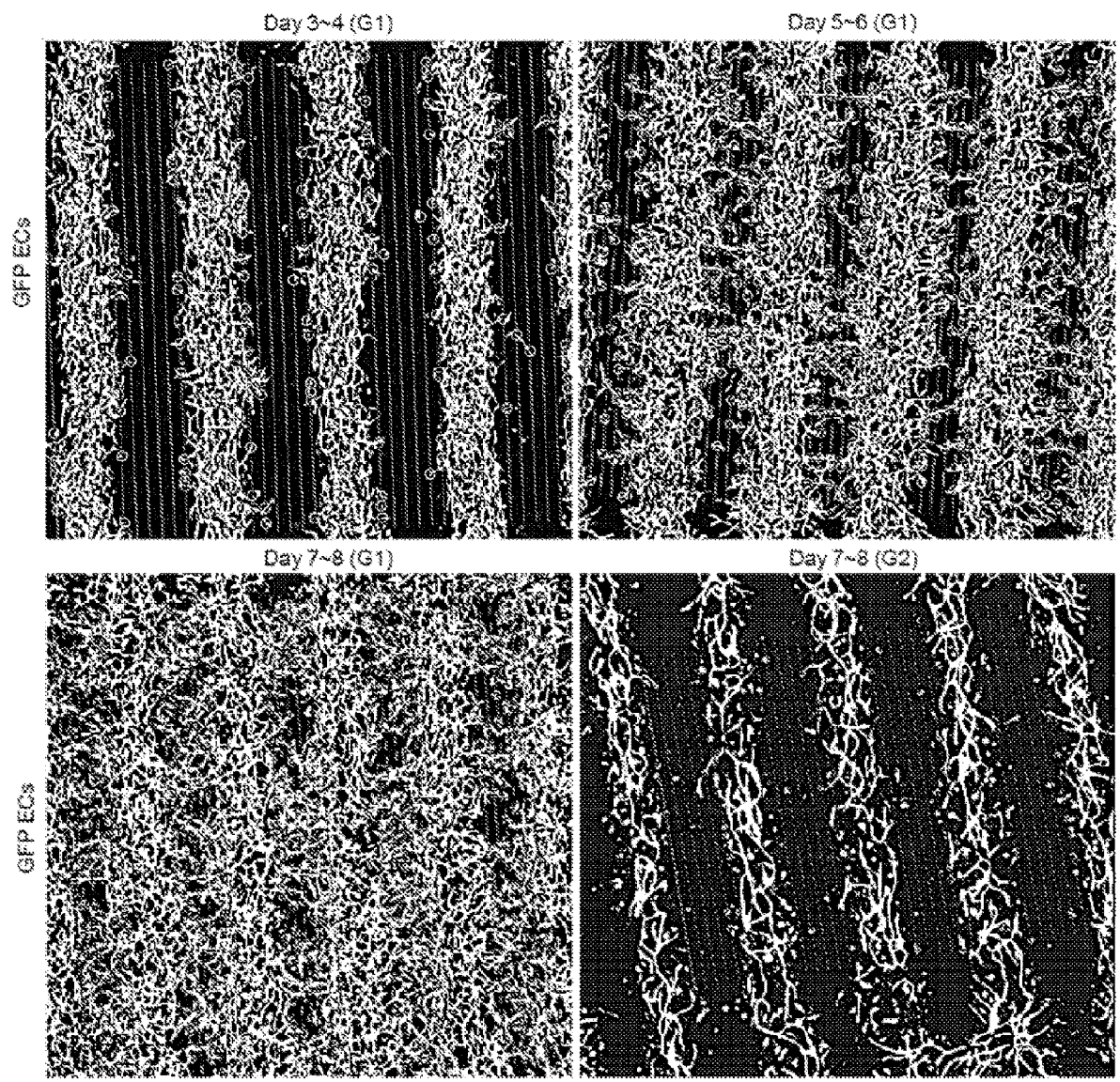
Figures 13B, 13C:
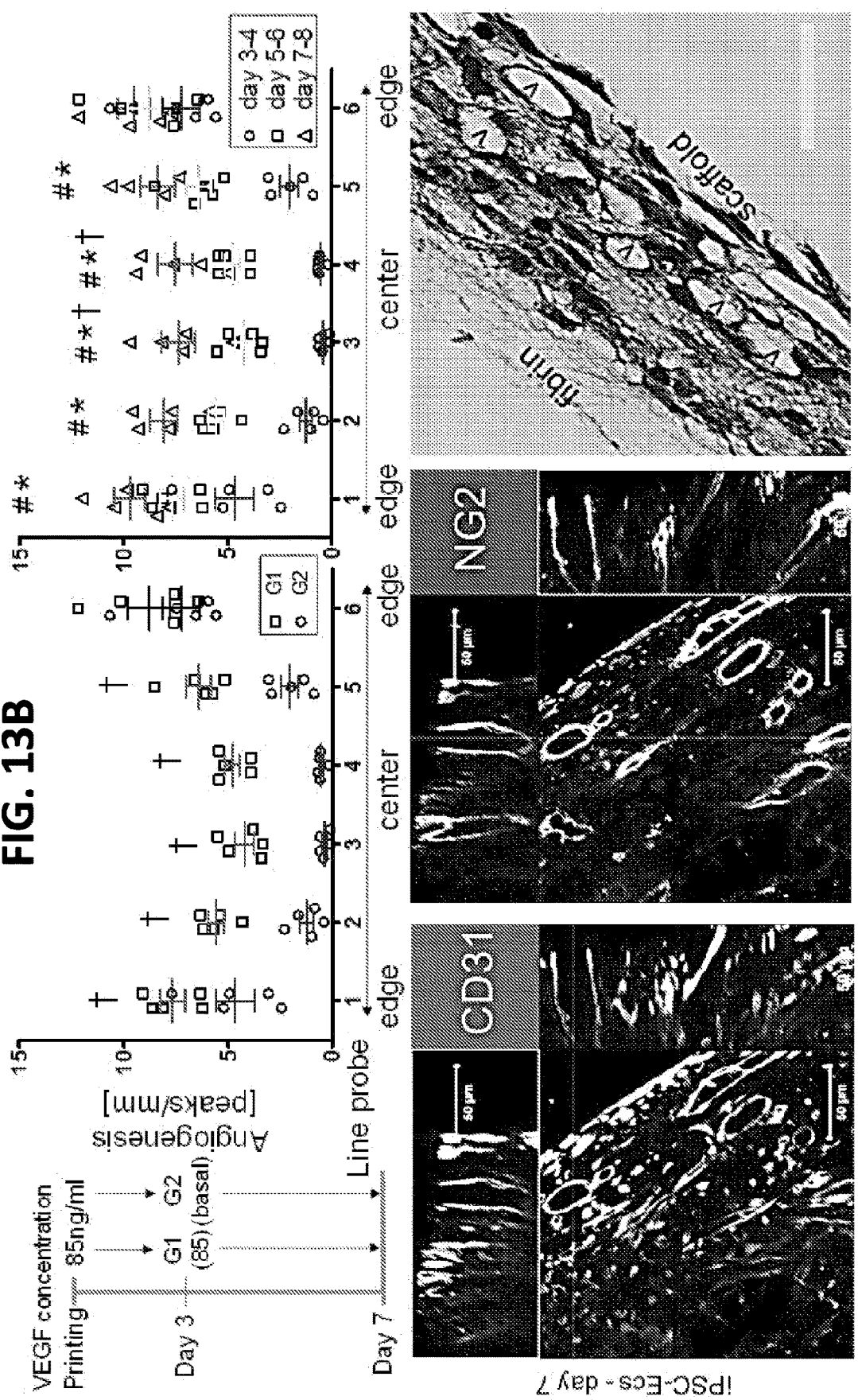

FIGS. 13A-13C are digital images (A and C) and a set of graphs (B) showing results obtained in 3D vascularized tissue containing GFP positive primary endothelial cells, pericytes, and fibroblasts. (A) 8 bit images of printed GFP endothelial cells (white) were quantified. Five line probes were placed in each gap between stripes of the printed geometry. Each line probe detects peaks (hollow circles) of GFP intensity above a threshold. Line 1 and 6, 2 and 5, 3 and 4 indicate edge, intermediate, and center of each gap, respectively. (B) Two experimental groups are compared. Group 1 (G1) indicates 85 ng/ml of VEGF treatment of a week, and group 2 (G2) indicates 85 ng/ml of VEGF treatment for the first 3 days and basal media level of VEGF (1.7 ng/ml) afterward. Angiogenesis was quantified as a number of GFP peaks in each line probe. The quantification of angiogenesis was performed between groups and time frames of G (n=5; number of printings). Error bars indicates standard error and mean. Two-way ANOVA and Bonferroni post-hoc pair comparison. † indicates statistical significance ($p<0.05$) between groups (left figure) and day 5-6 and day 7-8 (right figure). # and * indicates statistical significance ($p<0.05$) in day 3-4 vs. day 5-6 and day 3-4 vs. day 7-8, respectively. (C) Tissues containing iPSC derived endothelial cells at day 7 were cross section cut with 100 and 5 microns thickness using Vibrotome and Microtome. 100 μm thick tissue sections were stained with CD31 (endothelial cells) and NG2 (pericytes). 10 μm thick tissue slices were H&E stained. "v" indicates cross sections of microvessels.

Figure 14:
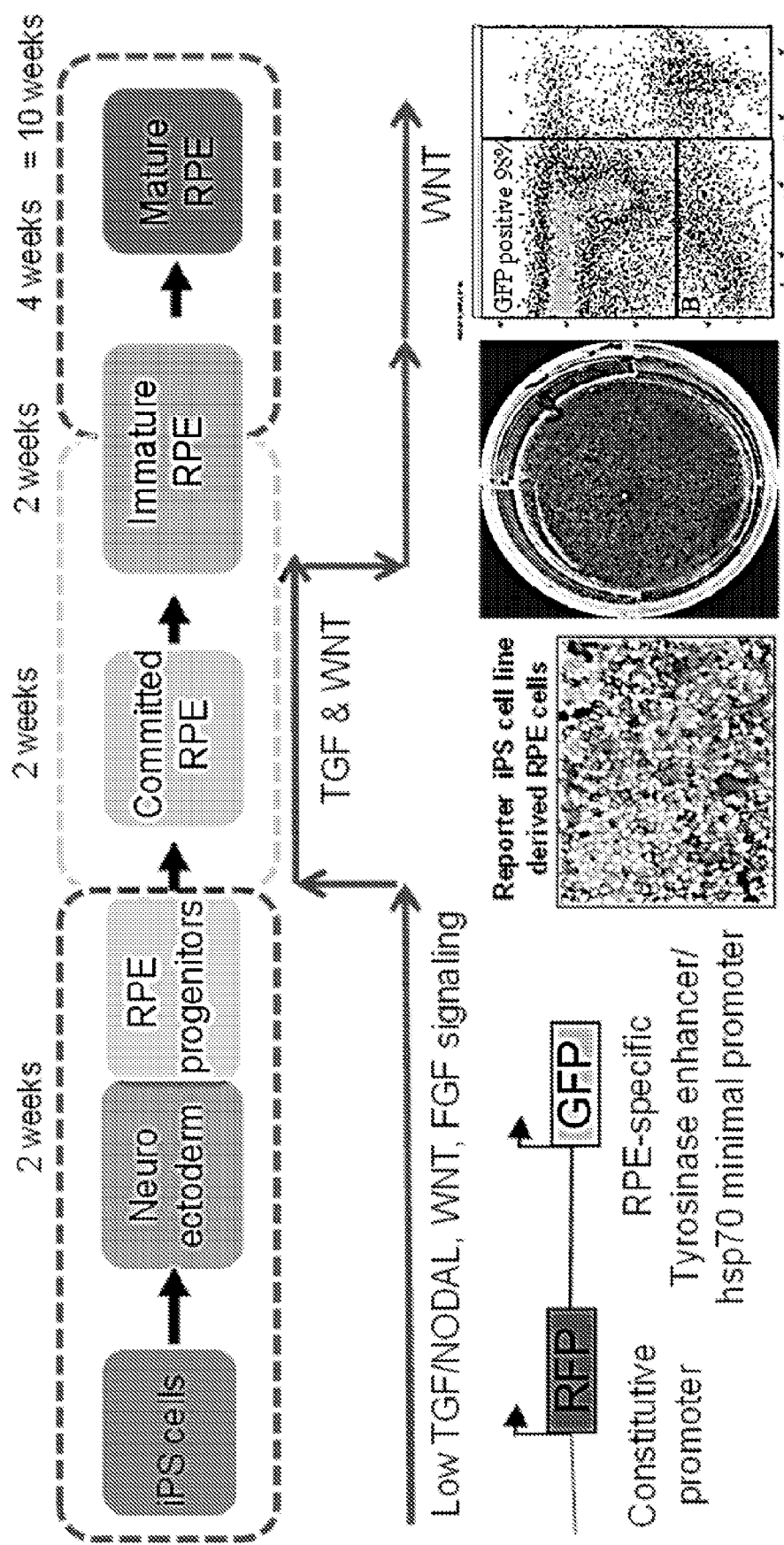
Figure 16B:
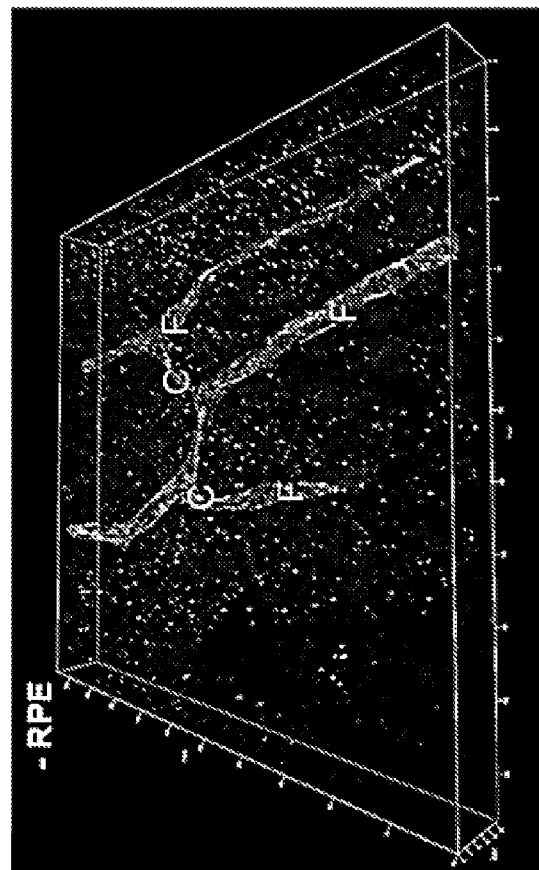
Figure 16A:
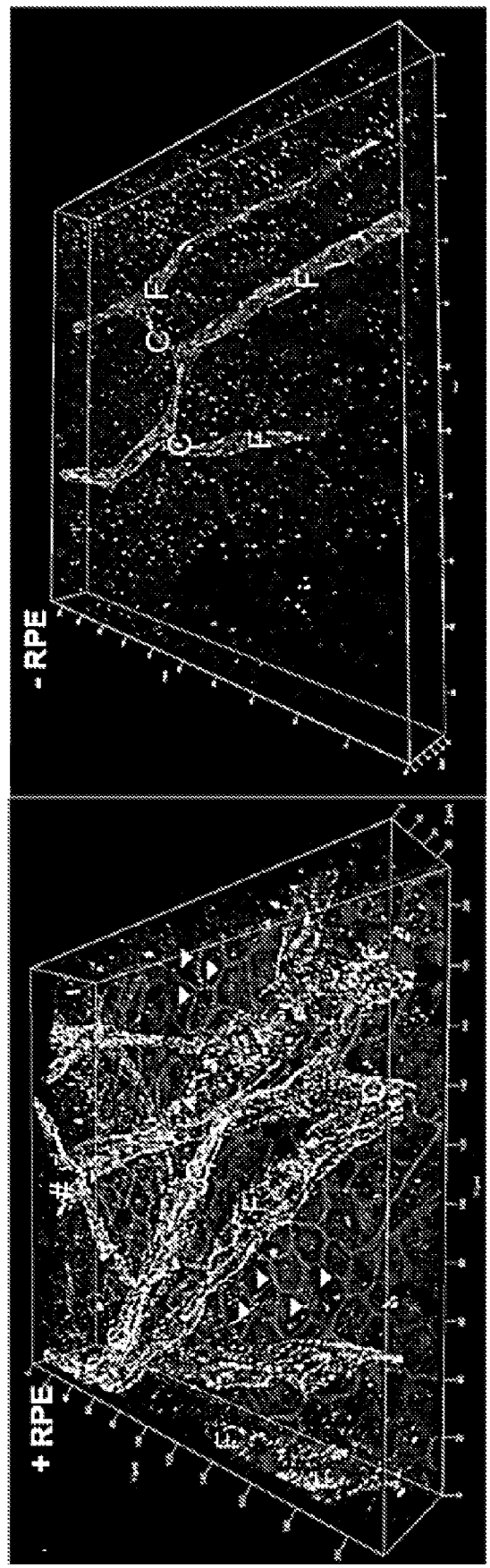
Figure 16C:
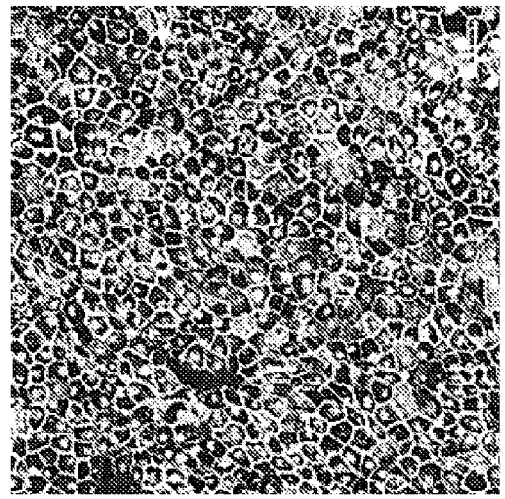
Figure 16J:
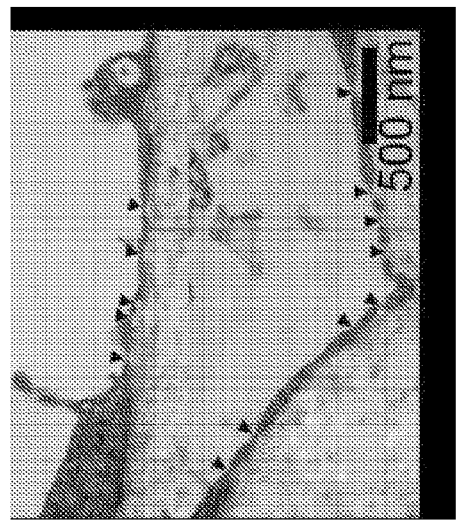
Figure 16I:
Figure 16H:
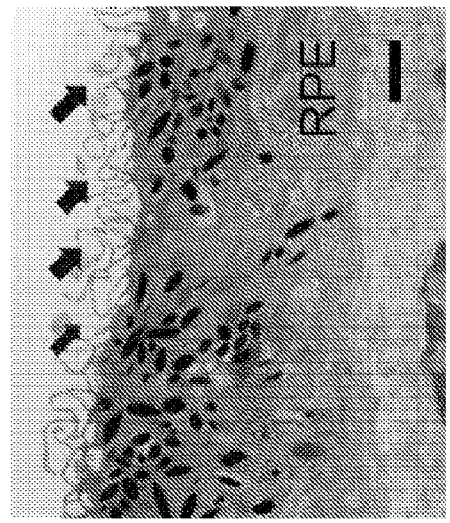

FIG. 14 a schematic diagram of engineering outer blood retina barrier using human induced pluripotent stem cells (iPSCs). Purity can be tested using reporter iPSC line with GFP expression of RPE specific gene. GFP also allows the monitoring of RPE maturation and the epithelial phenotype of RPE in the 3D RPE/choroid tissue.

FIGS. 15A-15C are digital images of bioprinted outer blood retina barrier (BRB) on a PLGA scaffold with inherent viscosity of 0.6. Printed tissues were fixed at 6 weeks after printing. iPSC derived RPE cells were stained with (A and C) Ezrin (cytoplasmic peripheral membrane protein, located in cytoplasm) and E-cadherin (junctional protein, cell boundary). (B) Microvasculature was stained with fenestrated endothelial-linked structure (FELS) protein. (C, panels 1,2) Expression of Ezrin (arrow heads) is localized in apical region of RPE, an evidence of RPE polarity. (C, panel 3) 3D reconstruction of confocal images. Images were taken by Leica DMi8.

FIGS. 16A-16J are digital images showing the effect of RPE on development of the fenestration of "choriocapillaris". (A,B) 3D reconstruction of engineered tissue with and without RPE. After 6-7 weeks of culture, printed tissues were stained with fenestrated endothelial-linked structure (FELS: fenestration marker, "F") and CD31 (endothelial cell marker, "C") in "choroid" and E-cadherin (junctional protein, arrow heads) of RPE. (D-G) microvascular network of local (D,F) and entire (E,G) "choroid" tissues. (D-G) image was separated into FELS and CD31 stains. (H) Transmission electron microscopy of RPE with apical processing (arrows). (I) "Choriocapillaris" is labeled as "v". (J) Fenestration of "choriocapillaris," a special feature of choriocapillaris, labeled as black arrow heads.

FIGS. 17A-17I are digital images showing the effect of STAT3 expression in RPE cells on "choriocapillaris." Healthy, STAT3 overexpressed, and STAT3 mutated iPSC derived RPE cell monolayer were formed on healthy "choroid." After 6 weeks, tissues were fixed in 4% PFA. Z-stack confocal images were separated into three sections as RPE (A-C), subRPE/scaffold (D-F), and "choroid" (G-I). RPE region was stained with Ezrin (cytoplasm) and E-cadherin (cell boundary). Choroid region was stained with FELS and CD31. Scale bar=100 μm. STAT3 overexpression induced vascularization of the subRPE region.

FIGS. 18A-18I are digital images showing the effect of hypoxia on "choriocapillaris." RPE-"choroid" tissues were treated with DMOG (100 μM) after 4 weeks from printing. DMOG inhibits prolyl-4-hydroxylase and induces hypoxia-inducible factor. DMOG was treated on only apical region of RPE or on both apical region of RPE and "choroid" sides. After two weeks of DMOG treatment, tissues were fixed in 4% PFA. Z-stack confocal images were separated into three sections as RPE (A-C), subRPE/scaffold (D-F), and "choroid" (G-I). RPE was recognized by Hoescht (nuclei). Choroid was stained with CD31. Scale bar=100 μm. DMOG treated RPE induced vascularization in the subRPE region.

DETAILED DESCRIPTION OF SEVERAL EMBODIMENTS

Bioprinting technology can be used to build complex three dimensional structures involving multiple cell types. It uses two disclosed features: (1) cells seeded in the form of large droplets as "bio-ink" that contains several hundred to many thousands of cells mixed with degradable biomaterials; (2) cells are seeded using needles that can move in a spatially and temporally controlled user-defined manner with precision. The three dimensional architecture in bioprinted tissue allows all the different cell types to mature simultaneously, thus increasing the likelihood of their working together like a native tissue. Disclosed herein is a three-dimensional engineered BRB that contains a polarized RPE monolayer, and endothelial cells forming microvessels; the three-dimensional engineered BRB is produced by bioprinting cells onto a biocompatible scaffold. This three-dimensional engineered BRB can be produced to from wild-type cells or one or more mutated cells. The three-dimensional engineered BRB or can be produced as a model of a disease. In some embodiments, in order to model a disease, the three-dimensional engineered BRB can be treated with a chemical agent and/or the three-dimensional engineered BRB can include one more cell types that include genetic mutations. In the engineered BRB, three dimensional microvessels derived from the endothelial cells are lined in a tissue containing choroidal fibroblasts and pericytes located underneath retinal pigment epithelial (RPE) cells. This engineered BRB can be used as a model for identifying molecular pathways in diseases of BRB, for discovering and testing drugs that affect BRB, and as a cell-based therapy. In some embodiments, the RPE, endothelial cells, fibroblasts, and/or pericytes can be derived from the same induced pluripotent stem cell line (iPSC), such as a human iPSC cells.

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). In order to facilitate review of the various embodiments of this disclosure, the following explanations of specific terms are provided:

Age-related macular degeneration (AMD): A disease that is a major cause of blindness in the United States and other industrialized nations. (Evans J, Wormald R., British Journal Ophthalmology 80:9-14, 1996; Klein R, Klein B E K, Linton K L P, Ophthalmology 99:933-943, 1992; Vingerling J R, Ophthalmology 102:205-210, 1995). Early AMD is characterized clinically by drusen, which are extracellular deposits of proteins, lipids, and cellular debris, (Hageman G S, Mullins R F, Mol Vis 5:28, 1999), that are located beneath the retinal pigment epithelium (RPE). The RPE provides nutritional, metabolic, and phagocytic functions for the overlying photoreceptors. Significant vision loss results from dysfunction or death of photoreceptors in the macula in association with late stages of AMD (geographic atrophy of the retinal pigment epithelial cells and subretinal neovascularization).

Bio-Ink: A liquid, semi-solid, or solid composition for use in bioprinting. In some embodiments, bio-ink comprises cells, cell solutions, cell aggregates, cell-comprising gels, multicellular bodies, or tissues. In some embodiments, the bio-ink can be a solid or semi-solid. In some embodiments, the bio-ink additionally comprises non-cellular materials that provide specific biomechanical properties that enable bioprinting. In some embodiments, the bio-ink comprises an extrusion compound. In some cases, the extrusion compound can be removed after the bioprinting process. In other embodiments, at least some portion of the extrusion compound remains with the cells post-printing and is not removed.

Bioprinting: Precise deposition of cells (e.g., bio-ink, cell solutions, cell-containing gels, cell suspensions, cell pastes, cell concentrations, multicellular aggregates, multicellular bodies, etc.) using a methodology that is compatible with an automated or semi-automated, computer-aided, three-dimensional printing device (e.g., a bioprinter). Bioprinting encompasses methods compatible with printing living cells such as an extrusion in continuous and/or discontinuous fashion. Extrusion in this context means forcing a semi-solid or solid bio-ink through an orifice, wherein the bio-ink retains its shape to a degree and for a time period after being forced through the orifice. Bioprinting also encompasses aerosol spray methods wherein cells are applied by ejecting a substantially low viscosity liquid in a mist, spray, or droplets onto a surface. Suitable bioprinters include NOVOGEN BIOPRINTERS® from Organovo, Inc. (San Diego, Calif.) and 3D DISCOVERY® from RegenHU Ltd, (Switzerland). Bioprinters can be used to produce three-dimensional engineered tissue, for example by printing cells in multiple layers on a substrate, printing cells on one or both surfaces of a substrate sheet, and/or printing multiple layers on one or both opposite surfaces of substrate sheets.

Biocompatible: Any material, that, when implanted in a mammalian subject, does not provoke an adverse response in the mammal. A biocompatible material, when introduced into an individual, is not toxic or injurious to that individual, nor does it induce immunological rejection of the material in the subject.

Blood-retina barrier (BRB): In vivo, the outer BRB separates the neural retina from choroidal capillaries. The inner BRB includes the tight junctions formed within microvasculature and the retinal microglia located in the inner retina, which is close to the vitreous side. The outer BRB separates the neural retina from choroidal capillaries by tight junctions formed by the epithelial (RPE) cell layer. The outer barrier formed at the RPE cell layer in the eye functions, in part, to regulate the movement of solutes and nutrients from the choroid to the sub-retinal space. The tight junctions located between these cells mediate highly selective diffusion of molecules from the blood to the retina and the barrier helps maintain retinal homeostasis.

Capillary Network: A group of fine branching blood vessels formed by endothelial cells.

Cell: A structural and functional unit of an organism that can replicate independently, is enclosed by a membrane, and contains biomolecules and genetic material. Cells used herein may be naturally-occurring cells or artificially modified cells (e.g., fusion cells, genetically modified cells, etc.). The term "cell population" is used herein to refer to a group of cells, typically of a common (same) type. The cell population can be derived from a common progenitor or may comprise more than one cell type. An "enriched" cell population refers to a cell population derived from a starting cell population (e.g., an unfractionated, heterogeneous cell population) that contains a greater percentage of a specific cell type than the percentage of that cell type in the starting population. The cell populations may be enriched for one or more cell types and/or depleted of one or more cell types.

Cell-Culture Surface: A solid substrate, such as, but not limited to, polystyrene, which can physically support cells and a culture medium. Cell-culture surfaces can be coated with substances to improve cell adhesion, such as an extracellular matrix.

Defined or Fully defined: When used in relation to a medium, an extracellular matrix, or a culture condition, refers to a medium, an extracellular matrix, or a culture condition in which the chemical composition and amounts of approximately all the components are known. For example, a defined medium does not contain undefined factors such as in fetal bovine serum, bovine serum albumin or human serum albumin. Generally, a defined medium comprises a basal media (e.g., Dulbecco's Modified Eagle's Medium (DMEM), F12, or Roswell Park Memorial Institute Medium (RPMI) 1640, containing amino acids, vitamins, inorganic salts, buffers, antioxidants and energy sources)

which is supplemented with recombinant albumin, chemically defined lipids, and recombinant insulin. An exemplary fully defined medium is ESSENTIAL 8™ medium.

Differentiation: The process by which an unspecialized cell becomes a more specialized type with changes in structural and/or functional properties. The mature cell typically has altered cellular structure and tissue-specific proteins. More specifically, in the context of the present methods indicates the process of a human stem cell acquiring the cell type of a retinal pigment epithelial (RPE) cell with features indicative that said RPE cell is a mature, terminally differentiated cell. As used herein, "undifferentiated" refers to cells that display characteristic markers and morphological characteristics of unspecialized cells that clearly distinguish them from terminally differentiated cells of embryo or adult origin.

Disease: A disorder of cell, tissue, organ structure or function that produces specific signs or symptoms or that negatively affects the cell, tissue or organ, respectively, and is not simply a direct result of physical injury. An example of a disease is a retinal disease. Retinitis pigmentosa and age related macular degeneration are both non-limiting examples of retinal diseases. A "diseased cell" is a cell from a subject with a disease of interest. In some embodiments, a diseased cell includes a genetic mutation that is specific to the disease of interest. In some embodiments, a diseased cell is has epigenetic and/or proteomic changes that led to the diseased phenotype Embryonic stem (ES) cell: An undifferentiated pluripotent cell which is obtained from an embryo in an early stage, such as the inner cell mass at the blastocyst stage, or produced by artificial means (e.g. nuclear transfer) and can give rise to any differentiated cell type in an embryo or an adult, including germ cells (e.g. sperm and eggs).

Essentially free: In terms of a specified component, such as cells, this term is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

Extracellular Matrix (ECM): A composite of extracellular proteins, which provide physical and biological support to the surrounding cells. ECM proteins are often secreted by structural cells. A basement membrane is one type of ECM, which is a laminar organization of extracellular proteins supporting RPE and capillary.

Feeder-free or feeder-independent: A culture supplemented with cytokines and growth factors (e.g., TGFβ, bFGF, LIF) as a replacement for a feeder cell layer. Thus, "feeder-free" or feeder-independent culture systems and media may be used to culture and maintain pluripotent cells in an undifferentiated and proliferative state. In some cases, feeder-free cultures utilize an animal-based matrix (e.g. MATRIGEL™) or are grown on a substrate such as fibronectin, collagen or vitronectin. These approaches allow human stem cells to remain in an essentially undifferentiated state without the need for mouse fibroblast "feeder layers."

Fibroblast: A type of cell that synthesizes the extracellular matrix proteins to provide soft tissue construct. Fibroblasts are the most common cells of connective tissue. In vivo, fibroblasts form the structural framework (stroma) for animal tissues, and plays a role in wound healing. Fibroblasts also express the intermediate filament protein vimentin, a feature used as a marker to distinguish their mesodermal origin.

Growth factor: A substance that promotes cell growth, survival, and/or differentiation. Growth factors include molecules that function as growth stimulators (mitogens), factors that stimulate cell migration, factors that function as chemotactic agents or inhibit cell migration or invasion of tumor cells, factors that modulate differentiated functions of cells, factors involved in apoptosis, or factors that promote survival of cells without influencing growth and differentiation. Examples of growth factors are a fibroblast growth factor (FGF), epidermal growth factor (EGF), insulin-like growth factor (IGF), and vascular endothelial growth factor (VEGF).

Growth medium or expansion medium: A synthetic set of culture conditions with the nutrients necessary to support the growth (cell proliferation/expansion) of a specific population of cells. In one embodiment, the cells are stem cells. In other embodiments, the cells are endothelial cells or retinal pigment epithelial cells. Growth media generally include a carbon source, a nitrogen source and a buffer to maintain pH. In one embodiment, growth medium contains a minimal essential media, such as DMEM, supplemented with various nutrients to enhance stem cell growth. Additionally, the minimal essential media may be supplemented with additives such as horse, human, calf or fetal bovine serum.

Hydrogel: A solid, jelly-like material having a controlled cross-linked structure exhibiting no flow when in the steady state. A hydrogel can be a water-swellable polymeric matrix that can absorb a substantial amount of water to form an elastic gel, wherein "matrices" are three-dimensional networks of macromolecules held together by covalent or noncovalent crosslinks. Upon placement in an aqueous environment, dry hydrogels swell to the extent allowed by the degree of cross-linking.

Induced pluripotent stem cells (IPSCs): Cells generated by reprogramming a somatic cell by expressing or inducing expression of a combination of factors (herein referred to as reprogramming factors). iPSCs can be generated using fetal, postnatal, newborn, juvenile, or adult somatic cells. In certain embodiments, factors that can be used to reprogram somatic cells to pluripotent stem cells include, for example, Oct4 (sometimes referred to as Oct 3/4), Sox2, c-Myc, and Klf4, Nanog, and Lin28. In some embodiments, somatic cells are reprogrammed by expressing at least two reprogramming factors, at least three reprogramming factors, or four reprogramming factors to reprogram a somatic cell to a pluripotent stem cell.

Isolated: An "isolated" biological component, such as a nucleic acid, protein or cell that has been substantially separated or purified away from other biological components in the environment (such as a cell) in which the component naturally occurs, i.e., chromosomal and extra-chromosomal DNA and RNA, proteins and other cells. Nucleic acids and proteins that have been "isolated" include nucleic acids and proteins purified by standard purification methods. The term also embraces nucleic acids and proteins prepared by recombinant expression in a host cell as well as chemically synthesized nucleic acids and proteins. Similarly, an "isolated" cell has been substantially separated, produced apart from, or purified away from other cells of the organism in which the cell naturally occurs. Isolated cells can be, for example, at least 99%, at least 98%, at least 97%, at least 96%, 95%, at least 94%, at least 93%, at least 92%, or at least 90% pure.

Label: An agent capable of detection, for example by ELISA, spectrophotometry, flow cytometry, immunohistochemistry, immunofluorescence, microscopy, Northern analysis or Southern analysis. For example, a marker can be attached to a nucleic acid molecule or protein, thereby permitting detection of the nucleic acid molecule or protein. Examples of labels include, but are not limited to, radioactive isotopes, nitorimidazoles, enzyme substrates, co-factors, ligands, chemiluminescent agents, fluorophores, haptens, enzymes, and combinations thereof. Methods for labeling and guidance in the choice of markers appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

In some embodiments, the label is a fluorophore ("fluorescent label"). Fluorophores are chemical compounds, which when excited by exposure to a particular wavelength of light, emits light (i.e., fluoresces), for example at a different wavelength. Fluorophores can be described in terms of their emission profile, or "color." Green fluorophores, for example Cy3, FITC, and Oregon Green, are characterized by their emission at wavelengths generally in the range of 515-540$\lambda$. Red fluorophores, for example Texas Red, Cy5 and tetramethylrhodamine, are characterized by their emission at wavelengths generally in the range of 590-690$\lambda$. In other embodiments, the marker is a protein tag recognized by an antibody, for example a histidine (His)-tag, a hemagglutinin (HA)-tag, or a c-Myc-tag.

Layer: An association of cells, extracellular matrix components, or a biocompatible scaffold, in at least two dimensions, generally that is multiple cells thick. A layer can form a contiguous, substantially contiguous, or non-contiguous sheet of cells and/or extracellular matrix components. In general, each layer of an engineered retinal tissue described herein comprises multiple cells in three dimensions.

Leber congenital amaurosis (LCA): A rare inherited eye disease that appears at birth or in the first few months of life and primarily affects the retina. The presentation can vary because is it associated with multiple genes. However, it is characterized by characterized by nystagmus, photophobia, sluggish or absent pupillary response, and severe vision loss or blindness.

Mammal: This term includes both human and non-human mammals. Examples of mammals include, but are not limited to: humans and veterinary and laboratory animals, such as pigs, cows, goats, cats, dogs, rabbits and mice.

Marker or Label: An agent capable of detection, for example by ELISA, spectrophotometry, flow cytometry, immunohistochemistry, immunofluorescence, microscopy, Northern analysis or Southern analysis. For example, a marker can be attached to a nucleic acid molecule or protein, thereby permitting detection of the nucleic acid molecule or protein. Examples of markers include, but are not limited to, radioactive isotopes, nitorimidazoles, enzyme substrates, co-factors, ligands, chemiluminescent agents, fluorophores, haptens, enzymes, and combinations thereof. Methods for labeling and guidance in the choice of markers appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Pericyte: A contractile cell that wraps around the endothelial cells of capillaries and venules throughout the body, also known as Rouget cells or mural cells. Pericytes are embedded in basement membrane where they communicate with endothelial cells using both direct physical contact and paracrine signaling. Pericytes have a characteristic round nucleus and project finger-like extensions that wrap around the capillary wall, allowing the cells to regulate capillary blood flow in vivo.

Pluripotent: The property of a cell to differentiate into all other cell types in an organism, with the exception of extraembryonic, or placental, cells. Pluripotent stem cells are capable of differentiating to cell types of all three germ layers (e.g., ectodermal, mesodermal, and endodermal cell types) even after prolonged culture.

Pluripotent stem cells: Stem cells that: (a) are capable of differentiating into teratomas when transplanted in immunodeficient (SCID) mice; (b) are capable of differentiating to cell types of all three germ layers (e.g., can differentiate to ectodermal, mesodermal, and endodermal cell types); and (c) express one or more markers of embryonic stem cells (e.g., express Oct 4, alkaline phosphatase, SSEA-3 surface antigen, SSEA-4 surface antigen, nanog, TRA-1-60, TRA-1-81, SOX2, REX1, etc.), but that cannot form an embryo along with its extraembryonic membranes (are not totipotent).

Exemplary pluripotent stem cells include embryonic stem cells derived from the inner cell mass (ICM) of blastocyst stage embryos, as well as embryonic stem cells derived from one or more blastomeres of a cleavage stage or morula stage embryo (optionally without destroying the remainder of the embryo). These embryonic stem cells can be generated from embryonic material produced by fertilization or by asexual means, including somatic cell nuclear transfer (SCNT), parthenogenesis, and androgenesis. PSCs alone cannot develop into a fetal or adult animal when transplanted in utero because they lack the potential to contribute to all extraembryonic tissue (e.g., placenta in vivo or trophoblast in vitro).

Pluripotent stem cells include iPSC generated by reprogramming a somatic cell by expressing or inducing expression of a combination of factors (herein referred to as reprogramming factors.

Purified: Isolated, a term that does not require absolute purity; rather, it is intended as a relative term. Thus, a purified population of cells is greater than about 90%, 91%, 92%, 93%, 94%, 95%, 96%, 97%, 98%, 99% or 100% pure, or, most preferably, essentially free other cell types.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques. Similarly, a recombinant protein is one coded for by a recombinant nucleic acid molecule.

Rectangle: A quadrilateral with four right angles. A square is a species of rectangle. They are examples of polygons, which are plane figures with at least three straight sides and angles. In some embodiments of devices disclosed herein, a frame can be of any shape, such as oval, circular, polygonal, quadrilateral, rectangular or square.

Retina: A light-sensitive layer of tissue, which lines the inner surface of the eye.

Retinal pigment epithelium: A monolayer of pigmented cells between the choroid, a layer filled with blood vessels, and the retina.

Retinal pigment epithelial (RPE) cell: RPE cells can be recognized based on pigmentation, epithelial morphology, and apical-basal polarized cells. Differentiated RPE cells also can be visually recognized by their cobblestone morphology and the initial appearance of pigment. The terms "RPE cell" and "differentiated RPE cell" and "iPSC-derived RPE cell" and "human RPE cell" are terms is used generally to refer to differentiated RPE cells.

Retinitis pigmentosa (RP): An inherited, degenerative eye disease that causes severe vision impairment due to the progressive degeneration of the rod photoreceptor cells in the retina. This form of retinal dystrophy manifests initial symptoms independent of age. The initial retinal degenerative symptoms of Retinitis pigmentosa are characterized by decreased night vision (nyctalopia) and the loss of the mid-peripheral visual field. The rod photoreceptor cells, which are responsible for low-light vision and are orientated in the retinal periphery, are the retinal processes affected first during non-syndromic forms of this disease. Visual decline progresses relatively quickly to the far peripheral field, eventually extending into the central visual field as tunnel vision increases. Visual acuity and color vision can become compromised due to accompanying abnormalities in the cone photoreceptor cells, which are responsible for color vision, visual acuity, and sight in the central visual field. The progression of disease symptoms occurs in a symmetrical manner, with both the left and right eyes experiencing symptoms at a similar rate. There are multiple genes that, when mutated, can cause the retinitis pigmentosa phenotype. Inheritance patterns of RP have been identified as autosomal dominant, autosomal recessive, X-linked, and maternally (mitochondrially) acquired, and are dependent on the specific RP gene mutations present in the parental generation.

Scaffold: A tissue support such as synthetic scaffolds, for example polymer scaffolds and non-synthetic scaffolds, for example pre-formed extracellular matrix or a de-cellularized organ scaffold. A scaffold can be in a particular shape or form so as to influence or delimit a three-dimensional shape or form assumed by a population of proliferating cells. This term also refers to any type of pre-formed scaffold that is integral to the physical structure of the engineered tissue and cannot be removed from the tissue without damage/destruction of said tissue. In some examples the scaffold is a thin three-dimensional substrate having opposite faces that can be separately bioprinted or seeded with cells. For example, the opposite surfaces may be parallel to one another and the outline of the scaffold as viewed from above may be any shape, such as circular, elliptical, oval, or polygonal (for example a rectangle, such as a square).

The term "scaffold-less," therefore, is intended to imply that pre-formed scaffold is not an integral part of the engineered tissue at the time of use, either having been removed or remaining as an inert component of the engineered tissue. "Scaffold-less" is used interchangeably with "scaffold-free" and "free of pre-formed scaffold."

Stem cell: A cell that under suitable conditions is capable of differentiating into a diverse range of specialized cell types, while under other suitable conditions is capable of self-renewing and remaining in an essentially undifferentiated pluripotent state. The term "stem cell" also encompasses a pluripotent cell, multipotent cell, precursor cell and progenitor cell. Exemplary human stem cells can be obtained from hematopoietic or mesenchymal stem cells obtained from bone marrow tissue, embryonic stem cells obtained from embryonic tissue, or embryonic germ cells obtained from genital tissue of a fetus. Exemplary pluripotent stem cells can also be produced from somatic cells by reprogramming them to a pluripotent state by the expression of certain transcription factors associated with pluripotency; these cells are called "induced pluripotent stem cells" or "iPSCs".

Subject: An animal or human subjected to a treatment, observation or experiment.

Treatment: Therapeutic measures that cure, slow down, lessen symptoms of, and/or halt progression of a diagnosed pathologic condition or disorder. In certain embodiments, treating a subject with a retinal degeneration results in a decline in the deterioration of the retinal; an increase in the number of RPE cells, an improvement in vision, or some combination of effects.

Wild type: A strain, gene, or characteristic that prevails among individuals in natural conditions, as distinct from an atypical mutant type. Generally, individuals with a wild-type allele do not have a particular disease condition associated with mutations in that allele.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Biocompatible Scaffold

Biocompatible scaffolds are of use in the methods disclosed herein. Biocompatible scaffolds include synthetic biocompatible scaffolds or natural biocompatible scaffolds such as de-cellularized organ scaffolds. The biocompatible scaffold can include polymer, such as a synthetic polymer.

In some embodiments, the polymer used to produce the biocompatible scaffold is a biodegradable material, such as lactide/glycolide polymer or co-polymer, for example poly (D, L-lactide co-glycolide (PDGLA), poly(lactic-co-glycolic acid) (PLGA), poly(lactic acid) (PLA), poly(-L-lactic acid) (PLLA), poly (glycolic) acid (PGA), poly caprolactone (PCL), polyethylene glycol (PEG), silk, fibroin, collagen (vitrified or recombinant). Additional synthetic biodegradable polymers that may be used include, poly(D-lactide) (PDLA), poly(D,L-lactide) (PDLLA), poly-p-dioxanone (PDO) and polytrimethylene carbonate (PTMC) and their copolymers, as well as polyanhydrides, polyhydroxy butyrate, polyhydroxyvalerate, "pseudo" polyaminoacids (eg. (polyarylates and polycarbonates), polyesteramides (PEA), polyphosphazenes, polypropylene fumarates, and polyorthoesters and copolymers or multipolymers of these with each other and resorbable multi- or copolymers that combine one or more biodegradable component with a nonresorbable component (e.g. poly(lactide-co-ethylene oxide)) thereby making the copolymer biodegradable.

The scaffold can also be fabricated with a blend of polymers. Both natural (for example, collagen, elastin, poly (amino acids), and polysaccharides such as hyaluronic acid, glycosamino glycan, carboxymethylcellulose) and/or synthetic polymers can be used to manufacture scaffolds. The production of biocompatible scaffolds is disclosed, for example, in U.S. Published Patent Application No. 2007/0187857, and PCT Publication No. 2014152906, which are both incorporated herein by reference.

The rate of resorption of the biocompatible scaffold can also be selectively controlled. For example, the scaffold may be manufactured to degrade at different rates depending on the desired application. An substance, such as a therapeutic agent, growth factor, or extracellular matrix, can be coated on the surface of the scaffold, such as by immersing the scaffold into an aqueous solution of the substance, such as in phosphate buffered saline (PBS), and allowed the substance to precipitate onto the scaffold surface(s), or a substance can be sprayed, covalently crosslinked, or applied onto the composite or scaffold surface.

In some embodiments, the bioscaffold includes poly (D, L-lactide co-glycolide (PDGLA), poly(lactic-co-glycolic acid) (PLGA), poly(lactic acid) (PLA), poly(-L-lactic acid) (PLLA), poly (glycolic) acid (PGA), poly caprolactone (PCL), poly ethylene glycol (PEG), silk, fibroin, collagen (vitrified or recombinant), or a combination thereof. The bioscaffold can consist of PDGLA, PLGA, PLA, PLLA, PGA, PCL, PEG, poly ethylene glycol (PEG), silk, fibroin, or collagen (vitrified or recombinant). In a specific non-limiting example, the biocompatible scaffold includes or consists of PDGLA. The PDGLA can be cross-linked or uncross-linked. In specific non-limiting examples, the PDGLA has an inherent viscosity of 0.6-1.0.

In some embodiment, the half-life of the biocompatible scaffold is about two to six weeks, such as about 2, 3, 4, 5, or 6 weeks, or about from about 4 to about 6 weeks, when transplanted in vivo. In some embodiments, the intact biocompatible scaffold is maintained at least 2 weeks, or at least about 3 weeks, or at least about four weeks, to maintain the barrier structure until the RPE cells and the fibroblast produce an extracellular matrix (ECM) in vivo. In specific, non-limiting examples, the intact biocompatible scaffold is maintained for about 2 weeks, and the half-life of the biocompatible scaffold is about 4 to about 6 weeks.

A biocompatible scaffold can include a polymer, such as a synthetic polymer. The polymer can be formed into nanometer scale fibers, such as about 20-500 nm in diameter, but the fibers can be thicker. In one embodiment, the fibers are about 20 to about 50 nm in diameter. In another embodiment, the fibers are about 50 to about 100 nm in diameter. In a further embodiment, the fibers are about 100 to about 200 nm in diameter. In yet another embodiment, the fibers are about 200 to about 300 nm in diameter. In one embodiment, the fibers are about 300 to about 400 nm in diameter. In another embodiment, the fibers are about 400 to about 500 nm in diameter. In a further embodiment, the fibers are about 500 to about 700 nm in diameter. In yet another embodiment, the fibers are about 700 to about 1000 nm in diameter. In an additional embodiment, the fibers are about 1 to about 20 µm in diameter. In one embodiment, the fibers are about 20 to about 40 µm in diameter. In another embodiment, the fibers are about 40 to about 60 µm in diameter. In a further embodiment, the fibers are about 60 to about 80 µm in diameter. In another embodiment, the fibers are about 80 to about 100 µm in diameter. In yet another embodiment, the fibers are 100 µm or more in diameter. In one embodiment, the scaffold is formed by extrusion of polymer(s) using an electrospinning process. Other methods of fabricating nanofibers are available and well known in the art, see U.S. Published Patent application No. 2014/0341965, incorporated herein by reference.

The biocompatible scaffold may have a Young's modulus of at least 0.1 MPa to about 500 MPa and may have a thickness in a range from about 2 µm to about 6 µm, see U.S. Published Patent Application No. 2014/0234381, which is incorporated herein by reference.

In some implementations, the scaffold thickness may be from about 2µ to about 45 µm, such as about 2 µm to about 25 µm, such as 2 µm to about 10 µm, from about 2 µm to about 9 µm, from about 2 µm to about 4 µM, or from about 6 µm to about 9 µm. However, in some implementations, the thickness may be up to 25 µm. In specific non-limiting examples, the biocompatible scaffold is about 2 to about 3 µm thick, and is produced for, example, of higher molecular weight PDGLA (inherent viscosity (I.V.) 1.0). In other embodiments, the biocompatible scaffold is about 6 µm to about 9 µm thick, and is produced, for example, of lower molecular weight PDGLA (I.V. 0.6).

The biocompatible scaffold can be characterized by a diffusivity in the range from about 200 µg/mm$^2$ per day to about 300 µg/mm$^2$ per day, for example, 250 µg/mm$^2$ per day, which is the estimated diffusivity of a native Bruch's membrane.

The biocompatible scaffold can have pores distributed over the surface. Without being bound by theory, pores allow diffusion of nutrients across the membrane and allow cells to communicate through extracellular signaling across the membrane, in order to support RPE, endothelial cell, fibroblast and/or pericyte proliferation and differentiation. At the same time, pores are preferably not large enough to allow cells to migrate or infiltrate through the membrane.

Suitable pores may have diameters of less than about 1 µm, for example, the pores may be sized in range between about 0.1-1.0 µm, such as 0.5-1 µm. In some implementations, pores range in diameter from about 300-500 nm, for example, pores may be about 250, 275, 300, 325, 350, 375, 400, 425, 450, 475, or about 500 nm. In some implementations, pores are about 100, 200, 300, 400, 500, 600, 700, 800, 900 nm in diameter. In some implementations, pores are about 0.1 µm to 2.0 µm, from about 0.3 µm to about 1.7 µm, from about 0.5 µm to about 1.5 µm, or from about 0.8 µm to about 1.0 µm. In some implementations, the pores are about 0.5 to about 1.0 µm, or less. All of the pores in the biocompatible scaffold may be the same size, or the pores may have different sizes. These pore sizes are disclosed, for example, in U.S. Published Patent Application No. 2011/0004304, which is incorporated herein by reference.

Without being bound by theory, uniformity in pore size and/or pore spacing may enable RPE cells to grow in a uniform layer on the membrane, and importantly, to form tight junctions with one another. In some embodiment, the pore size and spacing maintains the morphology of the RPE cells and the endothelial cells on the surfaces of the biocompatible matrix. One function of RPE cells is to regulate molecules that cross into the retina. In addition, tight junctions between RPE cells form a continuous barrier.

Thus, in some implementations, pores are substantially evenly distributed over the surface of the scaffold. The pores may be arrayed in a regular pattern. For example, pores can be spaced about 1.0 µm from other pores. In some implementations, pores can be spaced at least 1.0 µm from other pores. In some implementations, the pores are substantially round. U.S. Published Patent Application No. 2011/0004304, incorporated by reference herein, discloses that pores may alternately have a hexagonal shape, or a modified hexagonal shape wherein the straight edges of a hexagon are replace by curved convex or concave edges. Clusters of pores can be also arranged hexagonally, for example, six or more round pores may be hexagonally arranged so that their overlap results in a modified hexagonal shape with convex edges. The larger pore sizes may be advantageous in that they enable multiple neighboring cells to directly interact, yet provide contact guidance for cell alignment along the grooves of the pores.

In some implementations, at least one surface of the biocompatible scaffold is treated with one or more compounds which aid in adhering a cell to a surface. By way of example but not by way of limitation, in some implementations, oxygen plasma treatment is used. Without being bound by theory, this changes the surface of the biocompatible scaffold to a hydrophilic surface. Thus, the bio-ink can be printed on this surface. In some embodiments, one surface of the biocompatible scaffold is treated with one or more compounds or agents which aid in adhering the cell to a surface, such as oxygen plasma and/or ECM proteins. In other embodiments, two surfaces of the biocompatible scaffold are treated with one or more compounds which aid in adhering the cell to a surface, such as oxygen plasma treatment or ECM proteins.

In additional embodiments, at least one surface of the biocompatible scaffold is treated to include an anchoring structure, such as, but not limited to, an extracellular matrix such as s collagen, laminin, gelatin, fibronectin, chondroitin sulfates, proteoglycans, elastins, hyaluronic acid, vitronectin and/or fibronectin or a combination thereof.

In some embodiments, at least one surface of the biocompatible scaffold is smooth (i.e., has a no surface topography on a scale exceeding a few nanometers). It is disclosed in U.S. Published Patent Application No. 2014/0234381 that on a smooth membrane. RPE cells form a characteristic honeycomb pattern with uninterrupted membranous localization of the tight junction markers. Cell morphology can be evaluated by image analysis.

Cells

The methods disclosed herein utilize retinal pigment epithelial (RPE) cells and endothelial cells, and optionally fibroblasts and pericytes. The cells can be from any mammal. The cells can be from a human, a non-human primate, or any other mammalian subject, such as a canine, porcine, feline, bovine, equine, or rodent subject. Generally, cells are utilized that are from the same species. In a specific non-limiting example, the cells used in the methods disclosed herein, including the RPE cells, endothelial cells, fibroblasts and pericytes are human.

Endothelial cells can be produced from any tissue, such as blood vessels. Fibroblasts can be derived from any connective tissue, including but not limited to, dermis, adipose, bone, choroid, and cartilage, or derived from stem cells or transdifferentiated from any other cell type. Perictyes can be derived from skeletal muscle, blood vessels, brain, retina, and bone marrow, or derived from stem cells or transdifferentiated from any other cell type. The cells can be from a cell line.

Retinal pigment epithelial (RPE) cells can be characterized based upon their pigmentation, epithelial morphology, and apical-basal polarity. Differentiated RPE cells can be visually recognized by their cobblestone morphology and the initial appearance of pigment. In addition, differentiated RPE cells have transepithelial resistance/TER, and transepithelial potential/TEP across the monolayer (TER>100 ohms·cm2; TEP>2 mV), transport fluid and $CO_2$ from the apical to basal side, and regulate a polarized secretion of cytokines. RPE-specific markers may include: cellular retinaldehyde binding protein (CRALBP), microphthalmia-associated transcription factor (MITF), tyrosinase-related protein 1 (TYRP-1), retinal pigment epithelium-specific 65 kDa protein (RPE65), premelanosome protein (PMEL17), bestrophin 1 (BEST1), and c-mer proto-oncogene tyrosine kinase (MERTK). RPE cells do not express (at any detectable level) the embryonic stem cells markers Oct-4, nanog or Rex-2. Specifically, expression of these genes is approximately 100-1000 fold lower in RPE cells than in ES cells or iPSC cells, when assessed by quantitative RT-PCR.

In some embodiments, all of the cells utilized to generate the three-dimensional engineered blood retinal barrier (BRB) comprising a choroid and retinal pigment epithelial cells are derived from the same subject. In other embodiments, the cells utilized to generate the three-dimensional engineered blood retinal barrier (BRB) comprising a choroid and retinal pigment epithelial cells are from different subjects. In some non-limiting examples, the cells are from HLA matched subjects, or universal donor stem cells (with no HLA alleles).

The choice of mammalian individuals as a source of cells is not particularly limited. Allogenic cells can be used.

Thus, in some embodiments, the cells are not matched for MHC (e.g., HLA). In some embodiments, when the cells obtained are to be used for regenerative medicine in humans, cells can be collected from the somatic cells from the subject to be treated, or another subject with the same or substantially the same HLA type as that of the subject to be treated.

"Substantially the same HLA type" indicates that the HLA type of donor matches with that of a patient to the extent that the transplanted cells, which have been obtained by inducing differentiation of iPSCs derived from the donor's somatic cells, can be engrafted when they are transplanted to the patient. The patient optionally can be treated with an immunosuppressant. In one example, it includes an HLA type wherein major HLAs (e.g., the three major loci of HLA-A, HLA-B and HLA-DR, the four major loci further including HLA-Cw) are identical. These cells can be used directly, e.g., the RPE cells, endothelial cells, fibroblasts, pericytes, can be isolated from a subject and used directly, or somatic cells can be used to produce iPSC or ES cells, for the generation of RPE, fibroblasts, pericytes and/or endothelial cells.

In some embodiments, the RPE cells and endothelial cells, and optionally fibroblasts and/or pericytes can be produced from a stem cell, such as an induced pluripotent stem cell (iPSC) or another type of stem cell, such as an embryonic stem cell or directly transdifferentiated from any somatic cells. Exemplary stem cells may be selected from embryonic, placental, umbilical, mesenchymal stem cells. Stem cells may be induced to differentiate into RPE cells, endothelial cells, fibroblasts, or pericytes by methods known in the art, for example, culturing the stem cells in a differentiation medium.

For the production of an iPSC, the starting somatic cell can be any cell of interest. Any cells other than germ cells of mammalian origin (such as, humans, mice, monkeys, pigs, rats etc.) can be used as starting material for the production of iPSCs. Examples include keratinizing epithelial cells, mucosal epithelial cells, exocrine gland epithelial cells, endocrine cells, liver cells, epithelial cells, endothelial cells, fibroblasts, muscle cells, cells of the blood and the immune system, cells of the nervous system including nerve cells and glia cells, pigment cells, and progenitor cells, including hematopoietic stem cells, amongst others. There is no limitation on the degree of cell differentiation, the age of an animal from which cells are collected and the like; even undifferentiated progenitor cells (including somatic stem cells) and finally differentiated mature cells can be used alike as sources of somatic cells in the present invention. In one embodiment, the somatic cell is itself a RPE cell such as a human RPE cell. The RPE cell can be an adult or a fetal RPE cell. Thus, in some embodiments, the somatic cell is a fetal human RPE cell, obtained from a human fetus of about week 9 to about week 38 of gestation, such as about week 9 to about week 16 of gestation, about week 17 to about week 25 of gestation, about 16 to about 19 weeks, or about week 26 to about week 38 of gestation. In this context, "about" means within 2 days.

Somatic cells isolated from a mammal can be pre-cultured using a medium known to be suitable for their cultivation according to the choice of cells before being subjected to the step of nuclear reprogramming. Specific non-limiting examples of such media include, but are not limited to, minimal essential medium (MEM) containing about 5 to 20% fetal calf serum (FCS), Dulbecco's modified Eagle medium (DMEM), RPMI1640 medium, 199 medium, F12 medium, and the like. One of skill in the art can readily ascertain appropriate tissue culture conditions to propagate particular cell types from a mammal, such as a human. In some embodiments, to obtain completely xeno-free human iPSCs, the medium can exclude ingredients derived from non-human animals, such as FCS. Media comprising a basal medium supplemented with human-derived ingredients suitable for cultivation of various somatic cells (particularly, recombinant human proteins such as growth factors), non-essential amino acids, vitamins and the like are commercially available; those skilled in the art are able to choose an appropriate xeno-free medium according to the source of somatic cells. Somatic cells pre-cultured using a xeno-free medium are dissociated from the culture vessel using an appropriate xeno-free cell dissociation solution, and recovered, after which they are brought into contact with nuclear reprogramming substances.

Generally, cells are cultured at about 35 to 38° C., usually at 37° C., in about 4-6% $CO_2$, generally at 5% $CO_2$, unless specifically indicated otherwise below.

Somatic cells can be reprogrammed to produce induced pluripotent stem cells (iPSCs) using methods known to one of skill in the art. One of skill in the art can readily produce induced pluripotent stem cells, see for example, Published U.S. Patent Application No. 20090246875, Published U.S. Patent Application No. 2010/0210014; Published U.S. Patent Application No. 20120276636; U.S. Pat. Nos. 8,058,065; 8,129,187; 8,278,620; PCT Publication NO. WO 2007/069666 A1, and U.S. Pat. No. 8,268,620, which are incorporated herein by reference. Generally, nuclear reprogramming factors are used to produce pluripotent stem cells from a somatic cell. In some embodiments, at least three, or at least four, of Klf4, c-Myc, Oct3/4, Sox2, Nanog, and Lin28 are utilized. In other embodiments, Oct3/4, Sox2, c-Myc and Klf4 is utilized.

For production of iPSC, cells are treated with a nuclear reprogramming substance, which is generally one or more factor(s) capable of inducing an iPSC from a somatic cell or a nucleic acid that encodes these substances (including forms integrated in a vector). The nuclear reprogramming substances generally include at least Oct3/4, Klf4 and Sox2 or nucleic acids that encode these molecules. A functional inhibitor of p53, L-myc or a nucleic acid that encodes L-myc, and Lin28 or Lin28b or a nucleic acid that encodes Lin28 or Lin28b, can be utilized as additional nuclear reprogramming substances. Nanog can also be utilized for nuclear reprogramming. As disclosed in published U.S. Patent Application No. 20120196360, exemplary reprogramming factors for the production of iPSCs include (1) Oct3/4, Klf4, Sox2, L-Myc (Sox2 can be replaced with Sox 1, Sox3, Sox15, Sox17 or Sox18; Klf4 is replaceable with Klf1, Klf2 or Klf5); (2) Oct3/4, Klf4, Sox2, L-Myc, TERT, SV40 Large T antigen (SV40LT); (3) Oct3/4, Klf4, Sox2, L-Myc, TERT, human papilloma virus (HPV)16 E6; (4) Oct3/4, Klf4, Sox2, L-Myc, TERT, HPV16 E7 (5) Oct3/4, Klf4, Sox2, L-Myc, TERT, HPV16 E6, HPV16 E7; (6) Oct3/4, Klf4, Sox2, L-Myc, TERT, Bmi1; (7) Oct3/4, Klf4, Sox2, L-Myc, Lin28; (8) Oct3/4, Klf4, Sox2, L-Myc, Lin28, SV40LT; (9) Oct3/4, Klf4, Sox2, L-Myc, Lin28, TERT, SV40LT; (10) Oct3/4, Klf4, Sox2, L-Myc, SV40LT; (11) Oct3/4, Esrrb, Sox2, L-Myc (Esrrb is replaceable with Esrrg); (12) Oct3/4, Klf4, Sox2; (13) Oct3/4, Klf4, Sox2, TERT, SV40LT; (14) Oct3/4, Klf4, Sox2, TERT, HPV16 E6; (15) Oct3/4, Klf4, Sox2, TERT, HPV16 E7; (16) Oct3/4, Klf4, Sox2, TERT, HPV16 E6, HPV16 E7; (17) Oct3/4, Klf4, Sox2, TERT, Bmi1; (18) Oct3/4, Klf4, Sox2, Lin28 (19) Oct3/4, Klf4, Sox2, Lin28, SV40LT; (20) Oct3/4, Klf4, Sox2, Lin28, TERT, SV40LT; (21) Oct3/4, Klf4, Sox2, SV40LT; or (22) Oct3/4, Esrrb, Sox2 (Esrrb is replaceable with Esrrg). In one non-limiting example, Oct3/4, Klf4, Sox2, and c-Myc are utilized. In other embodiments, Oct4, Nanog, and Sox2 are utilized, see for example, U.S. Pat. No. 7,682,828, which is incorporated herein by reference. These factors include, but are not limited to, Oct3/4, Klf4 and Sox2. In other examples, the factors include, but are not limited to Oct 3/4, Klf4 and Myc. In some non-limiting examples, Oct3/4, Klf4, c-Myc, and Sox2 are utilized. In other non-limiting examples, Oct3/4, Klf4, Sox2 and Sal 4 are utilized.

Mouse and human cDNA sequences of these nuclear reprogramming substances are available with reference to the NCBI accession numbers mentioned in PCT Publication No. WO 2007/069666, which is incorporated herein by reference. Methods for introducing one or more reprogramming substances, or nucleic acids encoding these reprogramming substances, are known in the art, and disclosed for example, in published U.S. Patent Application No. 2012/0196360 and U.S. Pat. No. 8,071,369, which both are incorporated herein by reference.

After being cultured with nuclear reprogramming substances, the cell can, for example, be cultured under conditions suitable for culturing ES cells. In the case of mouse cells, the culture is carried out with the addition of Leukemia Inhibitory Factor (LIF) as a differentiation suppression factor to an ordinary medium. In the case of human cells, it is desirable that basic fibroblast growth factor (bFGF) be added in place of LIF.

The iPSC can then be induced to differentiate, such as to form specific cell types of interest. Method for producing RPE from iPSC are known in the art, see for example, PCT Application No. PCT/US2016/050543 and Published PCT Application No. WO2014/121077, both incorporated herein by reference. Methods for producing fibroblasts, endothelial cells, and pericytes from iPSC and embryonic stem cells are disclosed, for example, in Orlova et al. (2014) Nature protocols, 9(6), 1514-1531; Kusuma and Gerecht (2016) Human Embryonic Stem Cell Protocols, 213-222. Patsch et al., (2015) Nature Cell Biology, 17(8), 994; Hewitt et al., PLoS One 2011 Feb. 28; 6(2):e17128. doi: 10.1371/journal-.pone.0017128, which all are incorporated herein by reference.

In some embodiments, the RPE, endothelial cells, fibroblast and pericytes can be produced from ES cells. Methods for producing RPE, endothelial cells, fibroblast and pericytes from ES cells are disclosed for example, in Levenberg et al. (2002) Proceedings of the National Academy of Sciences 99(7), 4391-4396; Wang et al., (2007) Nature Biotechnology 25(3), 317-318; Idelson et al. (2009) Cell Stem Cell 5(4), 396-408; Klimanskaya et al. (2004) Cloning and Stem Cells 6(3), 217-245; Togo et al., In Vitro Cell Dev Biol Anim. 2011 February; 47(2): 114-24. doi: 10.1007/s11626-010-9367-2. Epub 2010 Nov. 25, which all are incorporated herein by reference.

In other embodiments, cell lines are utilized. Examples of cell lines are BEST-4, 82-6, AMD-CD, and AS10 cells.

In some embodiments, the IPSC is produced from a healthy subject. In other embodiments, the iPSC can be produced from a subject with a particular disease, such as AMD, BEST disease, L-ORD disease, Hyper IgE syndrome, nemo deficiency syndrome, or Sorsby's fundus dystrophy. These iPSC can be used to produce endothelial cells, fibroblasts, pericytes, and RPE cells.

Hydrogels

Bio-inks are disclosed herein that include a hydrogel and cells, such as endothelial cells, fibroblasts, pericytes and RPE cells. In some embodiments, a bio-ink includes a hydrogel and endothelial cells. In other embodiments, a bio-ink includes a hydrogel and endothelial cells, and pericytes and/or fibroblasts. In further embodiments, a bio-ink includes a hydrogel and RPE cells.

The hydrogel can include natural polymers or synthetic (non-natural) polymers. A hydrogel can be non-biodegradable hydrogel, a natural biodegradable hydrogel, and/or a synthetic biodegradable hydrogel. Hydrogels can generally absorb fluid and, at equilibrium, typically are composed of 60-90% fluid and only 10-30% polymer. In one embodiment, the water content of hydrogel is about 70-80%. Generally, a hydrogel is biocompatible.

Altering molecular weights, block structures, degradable linkages, and cross-linking modes can influence strength, elasticity, and degradation properties of the hydrogels (Nguyen and West, 2002, Biomaterials 23(22):4307-14; Ifkovits and Burkick, 2007, Tissue Eng. 13(10):2369-85). Hydrogels can also be modified with functional groups for covalently attaching a variety of proteins (e.g., collagen) or compounds such as therapeutic agents. Molecules which can be incorporated into the hydrogel include, but are not limited to, glycoproteins, fibronectin; peptides and proteins; carbohydrates (both simple and/or complex); proteoglycans: antigens; oligonucleotides (sense and/or antisense DNA and/or RNA); antibodies and growth factors. In one embodiment, the hydrogel includes molecules that aid in the growth and proliferation of a cell, such as an endothelial cell, pericyte, fibroblast, or retinal pigment epithelial cell, when cultured in or on the hydrogel. Non-limiting examples of such molecules can include proteins, peptides, supplements, small molecule inhibitors, glycosaminoglycans, growth factors, nucleic acid sequences, and combinations thereof. These molecule can be a growth factor.

The hydrogel can be a gelatin hydrogel, a collagen hydrogel, a fibrin hydrogel, a polysaccharide hydrogel, an alignate hydrogel, a laminin hydrogel, a fibronectin hydrogel, a laminin hydrogel, a vitronectin hydrogel, a polyethylene glycol hydrogel, a gelatin methacryloyl hydrogel, or a combination thereof. In specific non-limiting examples, the hydrogel is a collagen based hydrogel. In other embodiments, the hydrogel is manufactured from biodegradable materials which degrade in vivo or in vitro, at a sufficiently slow rate to allow the cells to proliferate. Commercially available hydrogels include, but are not limited to, MATRIGEL® and NOVOGEL2@.

In certain embodiments, the hydrogel includes a self-assembly peptide, a fibrin, an alginate, an agarose, a hyaluronan, a hyaluronic acid, a chitosan, a chondroitin sulfate, a polyethylene oxide (PEO), a poly(ethylene glycol) (PEG), a collagen type I, a collagen type II hydrogel, or combination thereof. In a further embodiment, the hydrogel composition includes a hydrogel selected from the following: self-assembly peptide, fibrin, alginate, agarose, hyaluronan, hyaluronic acid, chitosan, chondroitin sulfate, collagen type L collagen type II, and combinations thereof. In additional embodiments, the hydrogel includes bioabsorbable materials selected from gelatin, alginic acid, chitin, chitosan, dextran, polyamino acids, polylysine, and copolymers of these materials.

The hydrogel can be made from alpha hydroxyl polyesters. Exemplary hydrogels are disclosed in U.S. Published Patent Application No. 2007/0098675 and U.S. Published Patent Application No. 2010/0179659, which are both incorporated herein by reference. In one embodiment, the hydrogel includes gelatin. Gelatin hydrogels are disclosed, for example, in Lin et al., Tissue Engineering Part A, DOI: 10.1089/ten.tea.2013.0642, 2014, incorporated herein by reference. In additional embodiments, the hydrogel includes hyaluronan. The hydrogel can include gelatin and hyaluronan.

A hydrogel can be prepared by crosslinking hydrophilic biopolymers or synthetic polymers (see PCT Application No. WO 2013/040559, incorporated herein by reference). Examples of the hydrogels formed from physical or chemical crosslinking of hydrophilic biopolymers include, but are not limited to, hyaluronans, chitosans, alginates, collagen, dextran, pectin, carrageenan, polylysine, gelatin and/or agarose. (see.: W. E. Hennink and C. F. van Nostrum, 2002. Adv. Drug Del. Rev. 54, 13-36 and A. S. Hoffman. 2002, Adv. Drug Del. Rev. 43, 3-12). These materials consist of high-molecular weight backbone chains made of linear or branched polysaccharides or polypeptides.

Examples of hydrogels based on chemical or physical crosslinking of synthetic polymers include but are not limited to (meth)acrylate-oligolactide-PEO-oligolactide-(meth) acrylate, poly(ethylene glycol) (PEO), poly(propylene glycol) (PPO), PEO-PPO-PEO copolymers (Pluronics), poly (phosphazene), poly(methacrylates), poly(N-vinylpyrrolidone), PL(G)A-PEO-PL(G)A copolymers, polyethylene imine), etc. (see A. S Hoffman, Adv. Drug Del. Rev, 43, 3-12, 2002). These hydrogels can be modified with fibronectin, laminin, or vitronectin.

In certain embodiments, one or more multifunctional cross-linking agents may be utilized as reactive moieties that covalently link biopolymers or synthetic polymers. Such bifunctional cross-linking agents may include glutaraldehyde, epoxides (e.g., bis-oxiranes), oxidized dextran, p-azidobenzoyl hydrazide, N-[a.-maleimidoacetoxy]succinimide ester, p-azidophenyl glyoxal monohydrate, bis-[-(4-azidosalicylamido)ethyl]disulfide, bis[sulfosuccinimidyl]suberate, dithiobis[succinimidyl proprionate, disuccinimidyl suberate, 1-ethyl-3-[3-dimethylaminopropyl]carbodiimide hydrochloride (EDC), N-hydroxysuccinimide (NHS) and other bifunctional cross-linking reagents known to those skilled in the art.

Methacrylic anhydride, methacryloyl chloride, and glycidyl methacrylate may be used to add methacrylate groups to one or more monomers of a polymer. Glycidyl methacrylate may be used, for example, for efficiency of reaction.

Polymerizing initiators include electromechanical radiation. Initiation of polymerization may be accomplished by irradiation with visible light, such as 380 to 740 nm, such as about 350 to about 700 nm, such as between about 514 nm and about 365 nm, such as about 380 nm. In some embodiments, the light intensity is about 10 m W/cm$^3$. In some embodiments, polymerization can also include cross-linking with ultraviolet light, such as UVA, UVB, and/or UVC light.

The mechanical properties of a cross-linked polymer matrix, such as a hydrogel may also be related to pore structure. Hydrogels with different mechanical properties may be desirable depending on the desired clinical application.

In one embodiment utilizing a cross-linking agent, polyacrylated materials, such as ethoxylated (20) trimethylpropane triacrylate, can be used as a photo-activated cross-linking agent. Components of an exemplary reaction mixture would include a thermoreversible hydrogel held at 39° C., polyacrylate monomers, such as ethoxylated (20) trimethylpropane triacrylate, a photo-initiator, such as eosin Y, catalytic agents, such as 1-vinyl-2-pyrrolidinone, and triethanolamine. Exposure of this reactive mixture to long-wavelength light (>498 nm) produces a cross-linked hydrogel.

In some embodiments, the hydrogel is a methacrylated gelatin hydrogel, such as a methacrylated hyaluronan (hyaluronic acid) hydrogel. The hydrogel can be a mixture of methacrylated gelatin and methacrylated hyaluronan. The hydrogel can be a gelatin hydrogel, such as a methacrylated gelatin, and/or methacrylated hyaluronan hydrogel that was photocrosslinked with visible light.

A photocrosslinked gelatin can be crosslinked using visible light. Suitable hydrogels are disclosed, for example, in Lin et al., Application of visible light-based projection stereolithography for live cell scaffold fabrication with designed architecture, Biomaterials. 2013 January; 34(2):331-9. doi: 10.1016/j.biomaterials.2012.09.048. Epub 2012 Oct. 22, and Lin et al., Cartilage Tissue Engineering Application of Injectable Gelatin Hydrogel with In Situ Visible-Light-Activated Gelation Capability in both Air and Aqueous Solution, Tissue Eng Part A. 2014 Apr. 9, which are both incorporated herein by reference.

A hydrogel can be further stabilized and enhanced through the addition of one or more enhancing agents. Enhancing agents include any compound added to the hydrogel matrix, in addition to the high molecular weight components, that enhances the hydrogel matrix by providing further stability or functional advantages. These include, for example, polar amino acids, amino acid analogues, amino acid derivatives, intact collagen, and divalent cation chelators, such as ethylenediaminetetraacetic acid (EDTA) or salts thereof. Polar amino acids are intended to include tyrosine, cysteine, serine, threonine, asparagine, glutamine, aspartic acid, glutamic acid, arginine, lysine, and histidine. In specific non-limiting examples, one or more of L-cysteine, L-glutamic acid, L-lysine, and/or L-arginine is utilized. An enhancing agent can be added to the hydrogel composition before or during the crosslinking of the high molecular weight components.

Stabilizing agents known in the art may be incorporated in compositions. Buffers, acids and bases may be incorporated in the compositions to adjust their pH. Agents to increase the diffusion distance of agents released from the composition may also be included.

For inclusion in the hydrogel, cells, such as fibroblasts, pericytes and endothelial cells, or retinal pigment epithelial (RPE) cells, can be expanded. For example, for inclusion in the hydrogel, cells of interest are detached from the surface of a culture container by treating with trypsin-EDTA and then collected. Culture solution is added to the collected cells to create a cell suspension. Centrifugation can be carried out when or after cells have been collected to provide a high cell density of cells. Common conditions for centrifugation include 30 g to 500 g and 1 to 10 minutes. In some embodiments, a cloning ring or cloning cylinder is used to hold the cell suspension on the hydrogel, keeping the cell suspension from flowing away from the hydrogel during seeding.

Bio-Ink

The tissues, arrays, and methods described herein involve bio-ink formulations and bioprinting methods to create three-dimensional engineered BRB structures. In certain embodiments, bioprinting includes the application of one or move bio-inks to a surface of the biocompatible scaffold. The bio-ink can include a medium and a hydrogel. In some embodiments, the bio-ink also includes fibrinogen. In some embodiments, the bio-ink includes endothelial cells, and optionally pericytes and/or fibroblasts. In other embodiments, a bio-ink can include retinal pigment epithelial cells.

The printing methods utilize bio-ink to create geometries, which produce layers or compartments to mimic a native BRB of a retina. In various embodiments, the bio-ink contains a cellular mixture of some proportion of endothelial cells, and optionally pericytes and fibroblasts, and includes a hydrogel (see above). In other embodiments, the bio-ink contains RPE cells and includes a hydrogel. In certain embodiments, bio-inks consist essentially of a certain cell type, e.g., either endothelial cells or RPE cells, and includes a medium and a hydrogel. In this context, "consisting essentially of" means that the specified cell type is the only cell type present, but the bio-ink may contain other non-cellular material including but not limited to extrusion compounds, hydrogels, extracellular matrix components, nutritive and media components, inorganic and organic salts, acids and bases, buffer compounds and other non-cellular components that promote cell survival, adhesion, growth, or facilitate printing.

In some embodiments, the bio-ink is a viscous liquid. In other embodiments, the bio-ink is a semi-solid. In further embodiments, the bio-ink is a semi-solid or a solid. In specific non-limiting examples, the viscosity of the bio-ink is greater than 100 centipoise, greater than 200 centipoise, greater than 500 centipoise, greater than 1,000 centipoise, greater than 2,000 centipoise, greater than 5,000 centipoise, greater than 10,000 centipoise, greater than 20,000 centipoise, greater than 50,000 centipoise, or greater than 100,000 centipoise. In other non-limiting embodiments, the viscosity of the bio-ink is less than 100 centipoise, less than 200 centipoise, less than 500 centipoise, less than 1,000 centipoise, less than 2,000 centipoise, less than 5,000 centipoise, less than 10,000 centipoise, less than 20,000 centipoise, less than 50,000 centipoise, or less than 100,000 centipoise, see U.S. Published Patent Application No. 2016/

0122723, which is incorporated herein by reference for a description of bio-inks and hydrogels.

In some embodiments, the bio-ink comprises greater than 50% live cells by volume. In other embodiments, the bio-ink comprises greater than 60% live cells by volume. In additional embodiments, the bio-ink greater than 70% live cells by volume. In yet other embodiments, the bio-ink comprises greater than 80% live cells by volume. In further embodiments, the bio-ink comprises greater than 90% live cells by volume. In more embodiments, the bio-ink comprises greater than 95% live cells by volume.

In some embodiments, the bio-ink can be applied as a layer on a biocompatible scaffold by an aerosol spray method. In other embodiments, the bio-ink can be applied as a layer or an individual compartment by an extrusion method.

In other embodiments, the bio-ink includes about 5 to about 30 million endothelial cells per milliliter, such as about 5 to about 20 million endothelial cells per milliliter, about 5 to about 15 million endothelial cells per milliliter, about 5 to about 10 million endothelial cells per milliliter, or about 5 to about 6 million endothelial cells per milliliter. In one non-limiting example, about 5.5 million endothelial cells per milliliter are included in the bio-ink. In other non-limiting examples, the bio-ink includes about 5, 5.5, 6, 6.5, 7, 7.5, 8, 9, 10, 15, 20, 25 or 30 million endothelial cells per milliliter.

In further embodiments, fibroblasts and/or pericytes are included in the bio-ink. In some embodiments, the bio-ink includes about 10 to about 50 million fibroblasts per milliliter, such as about 10 to about 40 million fibroblasts per milliliter, about 10 to about 30 million fibroblasts per milliliter, about 10 to about 20 million fibroblasts per milliliter, or about 10 to about 15 million fibroblasts per milliliter. In one non-limiting example, about 10 million fibroblasts per milliliter are included in the bio-ink. In other non-limiting examples, the bio-ink includes about 15, 20, 25, 30, 40, 45 or 50 million fibroblasts per milliliter. In yet other embodiments, the bio-ink includes about 0.5 to about 3 million pericytes, such as about 0.5 to about 2.5 million pericytes per milliliter, about 0.5 to about 2 million pericytes per milliliter, about 0.5 to about 1 million pericytes per milliliter, or about 0.5 to about 0.75 million pericytes per milliliter. In specific non-limiting examples, the bio-ink includes about 0.5, 0.6, 0.7, 0.8, 0.9, 1, 2 or 3 million pericytes per milliliter.

In other embodiments, the bio-ink includes about 5 to about 30 million endothelial cells per milliliter, about 10 to about 50 million fibroblasts per milliliter, and about 0.5 to about 3 million pericytes per milliliter. In further embodiments, the bio-ink includes endothelial cells, fibroblasts and pericytes at a ratio of 1:0.3:0.1 to 1:10:1, respectively. In a specific non-limiting example, the endothelial cells, fibroblasts and pericytes are present in the bio-ink at a ratio of 1:2:0.5, or 1.1:2:0.5, respectively.

Bio-inks can also be produced including RPE, such as including about 0.5 to about 50 million RPE cells per milliliter. In some embodiments, the bio-ink includes 1 to about 40 million RPE cells per milliliter, such as about such as about 2 to about 30 million RPE cells per milliliter, or about 5 to about 20 million RPE cells per milliliter. The bio-ink can include 0.5, 0.75, 1, 1.25, 1.5, 1.75, 2, 3, 4, 5, 6, 7, 8, 9, 10, 15, 20, 25, 30, 35, 40, 45 or 50 million RPE cells per milliliter.

Non-cellular bio-inks can also be used in the methods disclosed herein. These bio-inks do not include living cells, such as endothelial cells, fibroblast, pericytes and RPE cells.

In some embodiments, the non-cellular bio-ink comprises extracellular matrix proteins or peptides such as collagen or fibrinogen, hyaluronate, hyaluronan, fibrin, alginate, agarose, chitosan, chitin, cellulose, pectin, starch, polysaccharides, fibrinogen/thrombin, fibrillin, elastin, gum, cellulose, agar, gluten, casein, albumin, vitronectin, tenascin, entactin/nidogen, glycoproteins, glycosaminoglycans (GAGs) and proteoglycans which may contain for example chrondroitin sulfate, fibronectin, keratin sulfate, laminin, heparan sulfate proteoglycan, decorin, aggrecan, perlecan or any combination thereof. In other embodiments, the bio-ink is a suitable hydrogel, such as a synthetic polymer. Suitable hydrogels include, but are not limited to, those derived from poly (acrylic acid) and derivatives thereof, poly(ethylene oxide) and copolymers thereof, poly(vinyl alcohol), polyphosphazene, and combinations thereof. In various specific embodiments, the confinement material is selected from: hydrogel, NOVOGEL® agarose, alginate, gelatin, MATRIGEL®, hyaluronan, poloxamer, peptide hydrogel, poly(isopropyl n-polyacrylamide), polyethylene glycol diacrylate (PEG-DA), hydroxyethyl methacrylate, polydimethylsiloxane, polyacrylamide, poly(lactic acid), silicon, silk, or combinations thereof. In some embodiments, the non-cellular bio-ink comprises hydrogels or other support materials, cushion materials or confinement materials. In some embodiments, the non-cellular bio-ink does not comprise inorganic or synthetic polymer. In some embodiments, the non-cellular bio-ink does not comprise dead-cell debris.

Methods of Production

Methods for fabricating a three-dimensional engineered blood retinal barrier (BRB) comprising a choroid and retinal pigmented epithelial cells are disclosed herein. Generally, the method includes depositing a bio-ink comprising endothelial cells onto one surface of a biocompatible matrix, and depositing RPE cells, optionally in a bio-ink, onto a second (for example opposite) surface of the sheet of biocompatible matrix, such that the matrix is between the endothelial cells and the RPE cells. A non-cellular bio-ink optionally can be deposited on a surface of the biocompatible scaffold, for example to provide additional culture medium on the surface over bioprinted or otherwise deposited cells.

The cells and the biocompatible matrix form a layered surface, so that the biocompatible matrix is between the endothelial cells and the RPE cells, forming a layered structure. Thus, the three-dimensional engineered blood retinal barrier (BRB) is a discrete structure that extends in the x, y and z planes, such that cells are present in each of the planes, and includes both endothelial cells and RPE cells. The three-dimensional structure can be any suitable shape, including the tissue can be any suitable shape such as a rectangular (for example a square), oval, ellipsoid, circular, trapezoidal, rhomboidal, spherical, cuboidal, and the like.

Bioprinted tissues are made with a method that utilizes a rapid prototyping technology based on two or three-dimensional, automated, computer-aided deposition of cells, including cell solutions, cell suspensions, cell-comprising gels or pastes, cell concentrations, multicellular bodies (e.g., cylinders, spheroids, ribbons, etc.), and, optionally, confinement material onto a biocompatible support by a three-dimensional delivery device (e.g., a bioprinter). The disclosed BRB's are "engineered," as they are tissues wherein cells, cell solutions, cell suspensions, cell-comprising gels or pastes, cell concentrates, multicellular aggregates, and layers thereof are positioned to form three-dimensional structures by a computer-aided device (e.g., a bioprinter) according to a computer script. In further embodiments, the computer script is, for example, one or more computer programs, computer applications, or computer modules. In still further embodiments, three-dimensional tissue structures form through the post-printing adhesion of cells which, in some cases, is similar to self-assembly phenomena in early morphogenesis.

While a number of methods are available to arrange cells and/or layers thereof on a biocompatible scaffold to produce a three-dimensional structure including manual placement, positioning by an automated, computer-aided machine such as a bioprinter is advantageous. For example, the disclosed methods can provide rapid, accurate, and reproducible placement of cells to produce constructs exhibiting planned or pre-determined orientations or patterns of cells, multicellular aggregates and/or layers. In some embodiments, the methods provide a high cell density, while minimizing cell damage.

Bioprinting is disclosed for example, in U.S. Published Application No. 2016/0122723, which is incorporated herein by reference to the extent that it is not inconsistent with the present disclosure. In some embodiments, bioprinting is continuous and/or substantially continuous. A non-limiting example of a continuous bioprinting method is to dispense bio-ink (i.e., cells, cells combined with an excipient or extrusion compound, or aggregates of cells) from a bioprinter via a dispenser tip (e.g., a syringe, needle, capillary tube, etc.) connected to a reservoir of bio-ink. In further non-limiting embodiments, a continuous bioprinting method is to dispense bio-ink in a repeating pattern of functional units. In various embodiments, a repeating functional unit has any suitable geometry, including, for example, circles, squares, rectangles, triangles, polygons, and irregular geometries, thereby resulting in one or more tissue layers with planar geometry achieved via spatial patterning of distinct bio-inks and/or void spaces. In further embodiments, a repeating pattern of bioprinted function units comprises a layer and a plurality of layers are bioprinted adjacently (e.g., stacked) to form an engineered tissue or organ with laminar geometry. In various embodiments, at least two layers are bioprinted to form an engineered tissue. In further embodiments, one or more layers of a tissue are formed with laminar geometry and planar geometry. The layers may be on one another, or on opposite faces of a substrate, or in multiple layers on one or both faces of the substrate.

In some embodiments, the method of bioprinting is discontinuous. A non-limiting example of discontinuous bioprinting is when bio-ink or cells are dispensed, and then the flow of bio-ink or cells is stopped, paused for a certain amount of time, and then started again. This can allow for different bio-inks or cells, or the same bio-inks or cells to be layered with a delay in printing of the cells. In some embodiments, the discontinuous bioprinting is achieved using an aerosol spray type of bioprinting, wherein cells are applied to an existing tissue layer or surface using an aerosol spray technology. In some embodiments, the bio-ink can include endothelial cells and optionally fibroblasts and/or pericytes. In other embodiments, the bio-ink can include RPE cells. In some embodiments, a single layer or plurality of layers of cells or bio-inks are deposited, followed by a temporal delay in deposition of a single layer or plurality of layers cells or bio-inks. Any of the bio-inks can be deposited by extrusion (continues or discontinuous), or spraying (ink jetting or aerosol spraying).

In certain embodiments, the first bio-ink, comprising endothelial cells, and optionally fibroblast and pericytes, is deposited by extrusion onto a surface of the biocompatible scaffold. In other embodiments, the first bio-ink is deposited by spraying onto a surface of the biocompatible scaffold. In certain embodiments, the second bio-ink, comprising RPE cells, is deposited by spraying onto a surface of the biocompatible scaffold. In further embodiments, the second bio-ink, comprising RPE cells, is deposited by extrusion onto a surface of the biocompatible scaffold. In certain embodiments, a third bio-ink comprising a non-cellular matrix bio-ink is deposited by spraying onto a surface, such as the same surface of the biocompatible matrix. In other embodiments, a third bio-ink comprising a non-cellular matrix bio-ink is deposited by extrusion onto a surface, such as the same surface of the biocompatible matrix.

The third bio-ink optionally can be deposited into void spaces on the surface of the biocompatible scaffold, wherein the first bio-ink is not applied, or wherein the second bio-ink is not applied. In some embodiments, a bio-ink including the endothelial cells, and optionally fibroblasts and pericytes, is deposited on one surface of a biocompatible scaffold. Optionally, a third non-cellular bio-ink is deposited in spaces that occur between the deposited first bio-ink.

Any bio-ink disclosed herein can include any of the hydrogels listed above. Exemplary hydrogels include, but are not limited to, a gelatin hydrogel, a collagen hydrogel, a fibrin hydrogel, an alginate hydrogel, a polysaccharide hydrogel, a laminin hydrogel or a gelatin methacryloyl hydrogel. In one embodiment the hydrogel includes fibrin. In some embodiments, using multiple types of hydrogel and multiple bioprinting heads, premade channels can be made within printed tissue after bioprinting. For example, a hydrogel can be bioprinted that dissolves above certain temperature, then another hydrogel, which doesn't dissolve at that temperature, surrounding the previous printed structure, is bioprinted. When the printed tissue is in the inubated, such as, but not limited to, at a temperature such as 37° C., the temperature sensitive hydrogel is dissolved and the dissolved spaces become "channels" that help perfusion (see, for example, Kolesky et al. PNAS 2016 113 (12) 3179-3184 (Mar. 7, 2016, doi:10.1073/pnas.1521342113), incorporated herein by reference.

In some embodiments, the method includes: a. depositing a first bio-ink comprising a hydrogel and a first medium, wherein the hydrogel comprises endothelial cells, onto a biocompatible scaffold, such that the hydrogel adheres to a first surface of the biocompatible scaffold; b. maturing the deposited first bio-ink in a second medium for at least four days (such as five days, or one week) to allow the endothelial cells to form vessels; c. depositing retinal pigment epithelial cells in a third medium to form a single cell layer on a second surface of the biocompatible scaffold, wherein the first and the second surface of the biocompatible scaffold are opposite surfaces, such that biocompatible scaffold is between the endothelial cells and the retinal pigment epithelial cells; and d. culturing the deposited retinal pigment epithelial cells in the third medium so that they proliferate and mature.

A flow chart, showing an exemplary method of producing a three-dimensional engineered BRB is shown in FIG. 12. In some embodiments, one or more of the bio-inks, such as the first bio-ink, includes fibrinogen. Thus, a first medium can be utilized in the bio-ink for the cells that includes an effective amount of thrombin, which converts the fibrinogen strands to insoluble strands. The deposited endothelial cells, and optionally the fibroblasts and the pericytes (if included in the bio-ink), are then cultured in a growth medium that does not include an effective amount of thrombin.

In some embodiments, the first medium and/or the second medium includes an effective amount one or more of vascular endothelial growth factor (VEGF), angiopoietin-1 (ANG-1), aprotinin, epidermal growth factor (EGF), insulin-like growth factor (IGF), and fibroblast growth factor (FGF). Thus, the first medium and the second medium can include one, two, three, four, five or all six of these factors. In a specific non-limiting example, the first and the second media include all of these factors. Exemplary concentrations of EGF are 1-50 ng/ml. Exemplary concentrations of FGF are 1-1,000 ng/ml, and exemplary concentrations of IGF-1 are 1-500 ng/ml. An exemplary medium including these factors is disclosed below. In some embodiments, the first and second media comprise vascular endothelial cell growth factor (VEGF), angiopoietin 1, IGF, EGF, FGF, ascorbic acid, hydrocortisone, heparin sulfate, angiopoietin, and aprotinin. In specific non-limiting examples, the first medium and/or the second medium comprises 1-1,000 ng/ml of VEGF, 50-1000 ng/ml of angiopoietin 1, and 0.075-0.5 U/ml of aprotinin. In other specific non-limiting examples, the first medium and/or the second medium include 100 ng/ml ANG-1, 0.075 U/ml aprotinin. In additional embodiments, the medium includes an effective amount of EFG, IGF, FGF, ascorbic acid, hydrocortisone, and heparin sulfate. In further embodiments, the first medium and/or the second medium include thrombin, such as 0.5 U/ml to 10 U/ml, such as 0.5 U/ml or 1 U/ml.

Any of the biocompatible scaffolds disclosed above can be used in the disclosed methods. In specific non-limiting examples, the first bio-ink is deposited on a biocompatible scaffold that includes PDGLA, PLGA, PLA, PLLA, PGA, silk, fibroin, collagen (vitrified or recombinant), or a combination thereof. The biocompatible scaffold can include, or consist of, PDGLA. Optionally, the PDGLA can be cross-linked.

In further embodiments, the biocompatible scaffold is treated to increase hydrophobicity of at least one surface. In some examples, one surface of the biocompatible scaffold is treated to increase hydrophobicity. In other embodiments, two surfaces of the biocompatible scaffold are treated to increase hydrophobicity. In some examples, the biocompatible scaffold is treated using oxygen plasma prior to the first bio-ink is deposited on the treated surface. The biocompatible scaffold can be treated with oxygen plasma less than about one day prior to depositing the first bio-ink, such as less than about 18 hours, less than about 12 hours, or less than about 6 hours prior to depositing the first bio-ink. In some embodiments, the biocompatible scaffold is treated with oxygen plasma for about 24 hours, 18 hours, 12 hours, 6 hours, 3 hours or 1 hour prior to depositing the first bio-ink.

Cells in the first bio-ink are deposited onto the biocompatible scaffold, and optionally non-cellular bio-ink is deposited onto the same surface of the biocompatible scaffold in areas wherein the first bio-ink is not deposited. This non-cellular bio-ink can include, for example, the same hydrogel include in the first bio-ink. Optionally, fibrinogen is also included in the non-cellular bio-ink.

The fist bio-ink, comprising endothelial cells and optionally fibroblasts and pericytes is cultured on the biocompatible scaffold in a second medium for at least four days, such as at least 4, 5, 6, 7, 8, 9, 10, 11, 12, 13 or 14 days. In some embodiments, the cells are allowed to mature for at least five days, or at least a week. When the first bio-ink and optionally the non-cellular bio-ink include fibrinogen, the second medium does not include an effective amount of thrombin. The second medium is further described above. The culturing in the second medium occurs on the surface of the biocompatible scaffold on which the endothelial cells have been printed. Culturing in the second medium can occur, for example, by placing the substrate on the second medium with the face of the substrate that has been bioprinted with the endothelial cells in contact with the second medium. Alternatively, the second medium can be deposited on the surface of the bioprinted tissue to bring the second medium into contact with the endothelial cells on the surface of the substrate.

RPE cells are seeded onto a second surface of the biocompatible scaffold, such that the biocompatible scaffold is between the endothelial cells and the RPE cells. Thus, the endothelial cells and the RPE cells are on opposite surfaces. The RPE cells can be utilized in a second bio-ink, as described above. Alternatively, the RPE cells can be directly added to the second surface of the biocompatible surface without bioprinting. In some embodiments, the second surface of the biocompatible scaffold is coated with a component for cell adhesion, such as an extracellular matrix, prior to depositing the retinal pigment epithelial cells onto the second surface of the biocompatible matrix. The extracellular matrix can include one or more of collagen, laminin, gelatin, chondroitin sulfate, proteoglycans, elastin, hyaluronic acid, vitronectin and/or fibronectin. In some embodiments, the method includes adding a suspension of RPE cells to the second surface of the biocompatible scaffold, wherein the biocompatible scaffold includes an extracellular matrix. In one non-limiting example, the extracellular matrix includes vitronectin.

In some embodiments, about 100,000 to 400,000 RPE cells per 1 centimeter are deposited on the surface of the biocompatible scaffold. In several examples, about 100,000 to about 300,000 RPE cells per 1 centimeter are deposited on the surface of the biocompatible scaffold, or about 100,000 to about 200,000 RPE cells per 1 centimeter are deposited on the surface of the biocompatible scaffold.

Alternatively, depositing the retinal pigment epithelial cells can include depositing a second bio-ink comprising retinal pigment epithelial cells, a medium, and the second medium. The second bio-ink can include a hydrogel, and wherein the hydrogel in the second bio-ink comprise a gelatin hydrogel, a collagen hydrogel, a fibrin hydrogel, a polysaccharide hydrogel, an alignate hydrogel, a laminin hydrogel, a fibronectin hydrogel, a laminin hydrogel, a vitronectin hydrogel, a polyethylene glycol hydrogel, or a gelatin methacryloyl hydrogel. Bio-inks and hydrogels are disclosed above.

The RPE cells are cultured in a medium on the second surface of the biocompatible matrix. In some embodiments, this medium does not include VEGF and ANG-1. Thus, the RPE cells can be seeded in a third medium, which does not include an effective amount of ANG-1 and VEGF. An exemplary medium is disclosed in the examples section. In further embodiments, the medium can included VEGF and ANG-1. In some embodiments, the RPE cells are cultured until a monolayer of RPE cells is formed. The cells can be cultured, for example, for at least a week, such as for about 7, 8, 9, 10, 11 or 12, 13, 14, 15, 16 days.

In some embodiments, the RPE monolayer is contacted with prostaglandin E2, such as by including it in the culture medium. In some embodiments, the medium includes about 1-400 M prostaglandin E2. The RPE cells can be cultured in the medium including prostaglandin E2 at about 1 to 3 weeks after seeding, such as at about 2 weeks after seeding. Suitable concentrations include about 1, 10, 12, 50, 75, 100, 200, 300 or 400 μM prostaglandin E2. In a specific non-limiting example, the RPE is contacted with 50 µM prostaglandin E2. In other specific non-limiting examples the RPE cells are cultured in about 50 µM prostaglandin E2 at about 2 weeks after seeding the RPE cells on the second surface of the biocompatible matrix, In some embodiments, methods of fabricating a three-dimensional engineered blood retinal barrier (BRB) comprising a choroid and retinal pigment epithelial cells are provided. These methods include the following steps:

a. depositing a first bio-ink comprising endothelial cells, fibroblasts and pericytes in a collagen and fibrinogen hydrogel and a first medium comprising thrombin, vascular endothelial grown factor, epithelial growth factor (EGF), fibroblast growth factor (FGF), insulin-like growth factor (IGF), ascorbic acid, hydrocortisone, heparin sulfate, angiopoietin-1 and aprotinin, onto a biocompatible oxygen plasma treated poly (D, L-lactide co-glycolide) PDGLA scaffold, such that bioink of the endothelial cells, fibroblasts and periyctes adhere to a first surface of the biocompatible scaffold;

b. maturing the deposited first bio-ink on the first surface in the second medium comprising an effective amount of vascular endothelial grown factor, EGF, FGF, IGF, ascorbic acid, hydrocortisone, heparin sulfate, and angiopoietin-1 and aprotinin, in the absence of thrombin, for at four days to allow the endothelial cells to form vessels;

c. depositing retinal pigment epithelial cells in a third medium to form a layer on a second surface of the biocompatible scaffold, wherein the first and the second surface of the biocompatible scaffold are opposite surfaces, such that biocompatible scaffold is between the endothelial cells and the retinal pigment epithelial cells, and wherein the second surface is coated with vitronectin, and wherein the third medium comprises an effective amount of taurine-hydrocortisone-triiodo-thyronin, hydrocortisone, Triiodo-thyronin, fetal bovine serum d. culturing the deposited retinal pigment epithelial cells in the third medium comprising the effective amount of taurine-hydrocortisone-triiodo-thyronin, hydrocortisone, triiodo-thyronin, fetal bovine serum so that the deposited retinal pigment epithelial cells proliferate and mature; and e. culturing the endothelial cells, fibroblasts and the pericytes in a fourth medium comprising an effective amount of vascular endothelial grown factor, wherein the fourth medium does not comprise thrombin and angiopoietin-1;

f. culturing the endothelial cells, fibroblasts and the pericytes in a fifth medium optionally comprising an effective amount of vascular endothelial grown factor, wherein the fifth medium does not comprise thrombin, angiopoietin-1, and aprotinin; and g. culturing the retinal pigment epithelial cells in a sixth medium comprising an effective amount of prostaglandin E2 added to the third medium, thereby forming the three three-dimensional engineered BRB in which the cultured endothelial cells develop into an artificial choroid and the cultured retinal pigment epithelium cells develop into an artificial retinal pigment epithelium.

Generally, cells or the biocompatible scaffolds including cells, such as RPE cells and/or endothelial cells, are cultured at about 35 to 38° C., usually at 37° C., in about 4-6% $CO_2$, generally at 5% $CO_2$. In some embodiments, serum is included in any of the media disclosed herein, such as about 2-10% serum, for example, 5% serum. In some examples, the serum is fetal bovine serum.

Three Dimensional Engineered Ocular Tissue

Figure 1A:
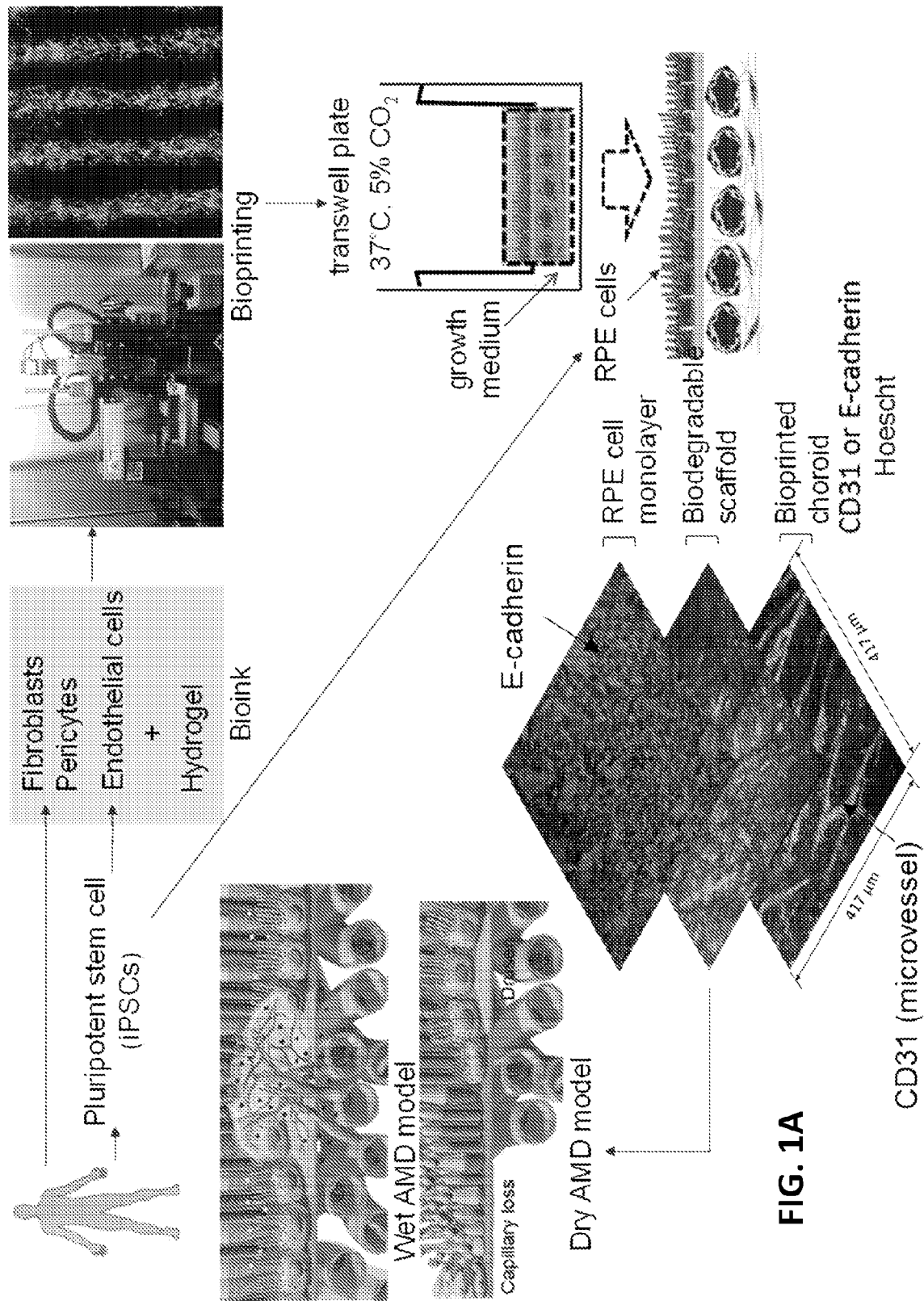
Figure 2:
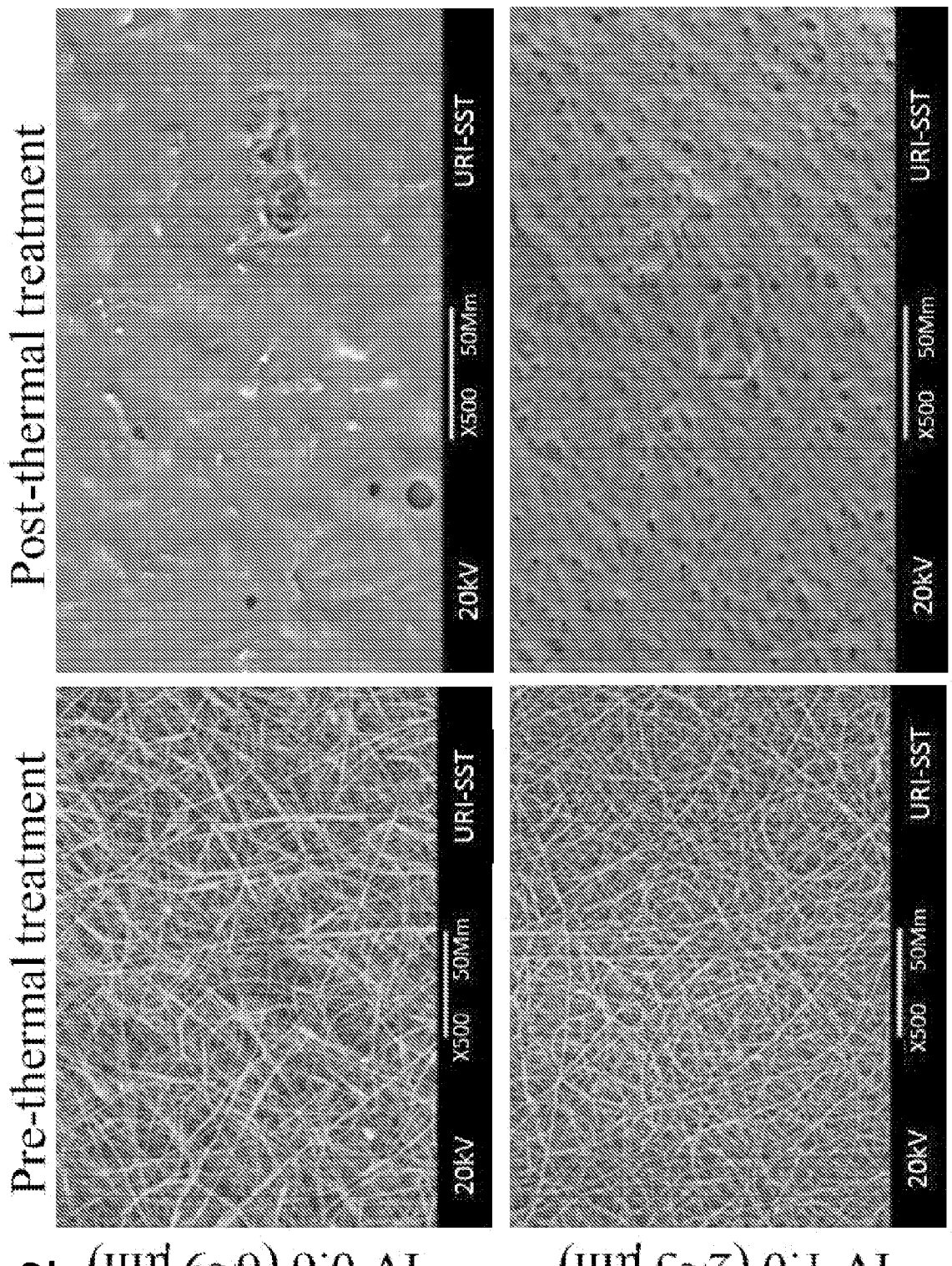
FIG. 2 shows photomicrographs of a poly (D,L-lactide-co-glycolide) (PDLGA) scaffold preparation with two different inherent viscosities (IV0.6 and 1.0). PDLGA (50:50, 1.0 and 0.6 I.V., respectively) were procured from Polysciences (Warminster, Pa.). A. 10% (w:v) PDLGA solution of the 1.0 I.V. and a 15% PDLGA solution of the 0.6 I.V. Electrospun scaffolds were measured for thickness (at 9 different locations/sheet) using an Ames Thickness Gauge. Materials were ethylene oxide sterilized using an Anprolene Sterilizer (12 hour cycle, 25° C., 72 hour exposure to vacuum (99%)) before they were shipped. Electrospun PDLGA materials were mounted onto an individual stub, sputter-coated with gold (Denton Vacuum Desk II) and viewed using JEOL JSM 5900LV SEM. Fiber diameter is approximately 500 nm in pre-thermal treated scaffolds.

The methods disclosed herein can be used to produce a three-dimensional engineered ocular tissue model, see for example, FIG. 1A and FIG. 14. Any of the material and methods disclosed above can be utilized to produce the three-dimensional engineered ocular tissue.

In some embodiments, this model includes a three-dimensional engineered outer blood retinal barrier (BRB), wherein the BRB includes a first layer and a second layer that form the three-dimensional structure. The first layer includes a choroid (or choroidal vasculature) that has a first bio-ink including a plurality of endothelial cells. In some non-limiting examples, the first bio-ink includes about 5 to about 30 million endothelial cells per milliliter. The second layer includes a plurality of retinal pigment epithelial cells. Optionally, a biocompatible scaffold is between the first layer and the second layer.

In some embodiments, the biocompatible scaffold can include, or consist of, PDGLA, PLGA, PLA, PLLA, PGA, PCL, PEG, silk, fibroin, collagen (vitrified or recombinant), or a combination thereof. In a specific non-limiting example, the biocompatible scaffold comprises PDGLA, such as cross-linked poly (D, L-lactide co-glycolide) (PDGLA). In another specific non-limiting example, the PDGLA is oxygen-plasma treated poly (D, L-lactide co-glycolide (PDGLA).

In some embodiments, the biocompatible scaffold can also include an extracellular matrix, for example that is coated on a surface of the biocompatible scaffold. The extracellular matrix can include a collagen, a laminin, a gelatin, a chondroitin sulfate, a proteoglycans, an elastin, a hyaluronic acid, avitronectin, a fibronectin or a combination thereof. In some embodiments, about 100,000 to 400,000 retinal pigment epithelial cells are present per 1 centimeter of a surface of the biocompatible scaffold.

In some embodiments, the biocompatible scaffold can be removed before use. For example, the biodegradable scaffold can be allowed to degrade in vitro, such as for about 24 hours to about 24 weeks, such as for about 48 hours to about 20 weeks, for about 72 hours to about 10 weeks. Exemplary periods for degradation include, but are not limited to, about 1, 2, 3, 4, 5, 6, 7, 8, 9, 1, 11, 12, 13, or 12 days. Exemplary periods for degradation also include 1, 2, 3, 4, 5, 6, 7, 8, 9, 10, 11, 12, 13, 14, 15, 16, 17, 18, 19, 20, 21, 22, 23 or 24 weeks. Exemplary periods for degradation can also be 1, 2, 3, 4, 5, or 6 months. The degradation can occur in a culture. In other embodiments, the biocompatible scaffold can be treated enzymatically, with heat, changes in pH or other chemicals to degrade the biocompatible scaffold. One of skill in the art can readily identify processes of use. In some embodiments, degradation is performed such that the three dimensional model is substantially free of the biocompatible scaffold at the time of use. Thus, the biocompatible scaffold cannot be detected using procedures known in the art.

The biocompatible scaffold may have a Young's modulus of at least 0.1 MPa to about 500 MPa and may have a thickness in a range from about 2 µm to about 6 µm, see U.S. Published Patent Application No. 2014/0234381, which is incorporated herein by reference.

In some implementations, the scaffold thickness may be from about 2µ to about 45 µm, such as about 2 µm to about 25 µm, such as 2 µm to about 10 µm, from about 2 µm to about 9 µm, from about 2 µm to about 4 µM, or from about 6 µm to about 9 µm. However, in some implementations, the thickness may be up to 25 µm. In specific non-limiting examples, the biocompatible scaffold is about 2 to about 3 µm thick, and is produced for, example, of higher molecular weight PDGLA (inherent viscosity (I.V.) 1.0). In other embodiments, the biocompatible scaffold is about 6 µm to about 9 µm thick, and is produced, for example, of lower molecular weight PDGLA (I.V. 0.6).

The biocompatible scaffold can be characterized by a diffusivity in the range from about 200 µg/mm² per day to about 300 µg/mm² per day, for example, 250 µg/mm² per day, which is the estimated diffusivity of a native Bruch's membrane.

The biocompatible scaffold can have pores distributed over the surface. Without being bound by theory, pores allow diffusion of nutrients across the membrane and allow cells to communicate through extracellular signaling across the membrane, in order to support RPE, endothelial cell, fibroblast and/or pericyte proliferation and differentiation. At the same time, pores are preferably not large enough to allow cells to migrate or infiltrate through the membrane. Pore sizes of use are specified above.

In further embodiments, the first bio-ink can include a plurality of fibroblasts and a plurality of pericytes. In some non-limiting examples, the first bio-ink includes about 10 to about 50 million fibroblasts per milliliter. In additional non-limiting examples, the first bio-ink comprises about 0.5 to about 3 million pericytes per milliliter.

The endothelial cells, fibroblasts and pericytes can be included in the first bioink in any ratio. In some embodiments, the endothelial cells, the fibroblasts and the pericytes are present in the first bio-ink at a ratio of 1:0.3:0.1 to 1:10:1, respectively. In additional embodiments, the endothelial cells, the fibroblasts and the pericytes are present in the first bio-ink at a ratio of 1:2:0.5, respectively.

The cells in the three-dimensional engineered ocular tissue model can be from any human species, including humans, non-human primates, and veterinary subjects. In some embodiments, all of the cells in the three-dimensional engineered ocular tissue model are from the same species.

One or more of the retinal pigment epithelial cells, endothelial cells, fibroblasts and pericytes can be human cells. In some embodiments, all of the retinal pigment epithelial cells, endothelial cells, fibroblasts and pericytes are human cells. In other embodiments, the endothelial cells and the retinal pigment epithelial cells are human cells.

These retinal pigment epithelial cells, endothelial cells, fibroblasts and pericytes can be from the same source or from different sources. In some embodiments, the retinal pigment epithelial cells, endothelial cells, fibroblasts and pericytes are from the same subject, or are derived from cells from the same subject. As discussed above, retinal pigment epithelial cells, endothelial cells, fibroblasts and/or pericytes can be MHC haplotype matched, patient-specific, or allogeneic.

In some embodiments, retinal pigment epithelial cells, endothelial cells, fibroblasts and/or pericytes are produced from induced pluripotent stem cells, embryonic stem cells, or multipotent stem cells.

Any cell can be used as a starting point for iPSCs. For example, cell types could be keratinocytes, fibroblasts, hematopoietic cells, mesenchymal cells, liver cells, or stomach cells. T cells may also be used as a source of somatic cells for reprogramming (U.S. Pat. No. 8,741,648). There is no limitation on the degree of cell differentiation or the age of an animal from which cells are collected; even undifferentiated progenitor cells (including somatic stem cells) and finally differentiated mature cells can be used as sources of somatic cells in the methods disclosed herein. In one embodiment, the somatic cell is itself a RPE cells such as a human RPE cell. The RPE cell can be an adult or a fetal RPE cell. iPSCs can be grown under conditions that are known to differentiate human ES cells into specific cell types, and express human ES cell markers including: SSEA-1, SSEA-3, SSEA-4, TRA-1-60, and TRA-1-81.

Somatic cells can be reprogrammed to produce induced pluripotent stem cells (iPSCs) using methods known to one of skill in the art. One of skill in the art can readily produce induced pluripotent stem cells, see for example, Published U.S. Patent Application No. 20090246875, Published U.S. Patent Application No. 2010/0210014; Published U.S. Patent Application No. 20120276636; U.S. Pat. Nos. 8,058,065; 8,129,187; 8,278,620; PCT Publication NO. WO 2007/069666 A1, and U.S. Pat. No. 8,268,620, which are incorporated herein by reference. Generally, nuclear reprogramming factors are used to produce pluripotent stem cells from a somatic cell. In some embodiments, at least three, or at least four, of Klf4, c-Myc, Oct3/4, Sox2, Nanog, and Lin28 are utilized. In other embodiments, Oct3/4, Sox2, c-Myc and Klf4 are utilized.

As discussed above, mouse and human cDNA sequences of these nuclear reprogramming substances are available with reference to the NCBI accession numbers mentioned in WO 2007/069666, which is incorporated herein by reference. Methods for introducing one or more reprogramming substances, or nucleic acids encoding these reprogramming substances, are known in the art, and disclosed for example, in published U.S. Patent Application No. 2012/0196360 and U.S. Pat. No. 8,071,369, which both are incorporated herein by reference.

The cells can be treated with a nuclear reprogramming substance, which is generally one or more factor(s) capable of inducing an iPSC from a somatic cell or a nucleic acid that encodes these substances (including forms integrated in a vector). The nuclear reprogramming substances generally include at least Oct3/4, Klf4 and Sox2 or nucleic acids that encode these molecules. A functional inhibitor of p53, L-myc or a nucleic acid that encodes L-myc, and Lin28 or Lin28b or a nucleic acid that encodes Lin28 or Lin28b, can be utilized as additional nuclear reprogramming substances. Nanog can also be utilized for nuclear reprogramming. An additional 22 examples are provided above. In one non-limiting example, Oct3/4, Klf4, Sox2, and c-Myc are utilized. In other embodiments, Oct4, Nanog, and Sox2 are utilized, see for example, U.S. Pat. No. 7,682,828, which is incorporated herein by reference. These factors include, but are not limited to, Oct3/4, Klf4 and Sox2. In other examples, the factors include, but are not limited to Oct 3/4, Klf4 and Myc. In some non-limiting examples, Oct3/4, Klf4, c-Myc, and Sox2 are utilized. In other non-limiting examples, Oct3/4, Klf4, Sox2 and Sal 4 are utilized. Factors like Nanog, Lin28, Klf4, or c-Myc can increase reprogramming efficiency and can be expressed from several different expression vectors. For example, an integrating vector such as the EBV element-based system can be used (U.S. Pat. No. 8,546,140). In a further aspect, reprogramming proteins could be introduced directly into somatic cells by protein transduction. As noted above, reprogramming may further comprise contacting the cells with one or more signaling receptors including glycogen synthase kinase 3 (GSK-3) inhibitor, a mitogen-activated protein kinase kinase (MEK) inhibitor, a transforming growth factor beta (TGF-β) receptor inhibitor or signaling inhibitor, leukemia inhibitory factor (LIF), a p53 inhibitor, an NF-kappa B inhibitor, or a combination thereof. Those regulators may include small molecules, inhibitory nucleotides, expression cassettes, or protein factors. It is anticipated that virtually any iPS cells or cell lines may be used.

In some embodiments, the iPSC can be modified to express exogenous nucleic acids, such as to include a tyrosinase enhancer operably linked to a promoter and a nucleic acid sequence encoding a first marker. The tyrosinase gene is disclosed, for example, in GENBANK® Accession No. 22173, as available on Jan. 1, 2013. This sequence aligns to chromosome 7 of mouse strain C57BL/6 location 5286971-5291691 (invert orientation). A 4721 base pair sequence is sufficient for expression in RPE cells, see Murisier et al., Dev. Biol. 303: 838-847, 2007, which is incorporated herein by reference. This construct is expressed in retinal pigment epithelial cells. Other enhancers can be utilized. Other RPE-specific enhancers include D-MITF, DCT, TYRP1, RPE65, VMD2, MERTK, MYRIP, and RAB27A. Suitable promoters include, but are not limited to, any promoter expressed in retinal pigment epithelial cells including the tyrosinase promoter. The construct can also include other elements, such as a ribosome binding site for translational initiation (internal ribosomal binding sequences), and a transcription/translation terminator. Generally, it is advantageous to transfect cells with the construct. Suitable vectors for stable transfection include, but are not limited to retroviral vectors, lentiviral vectors and Sendai virus.

Plasmids have been designed with a number of goals in mind, such as achieving regulated high copy number and avoiding potential causes of plasmid instability in bacteria, and providing means for plasmid selection that are compatible with use in mammalian cells, including human cells. Particular attention has been paid to the dual requirements of plasmids for use in human cells. First, they are suitable for maintenance and fermentation in *E. coli*, so that large amounts of DNA can be produced and purified. Second, they are safe and suitable for use in human patients and animals. The first requirement calls for high copy number plasmids that can be selected for and stably maintained relatively easily during bacterial fermentation. The second requirement calls for attention to elements such as selectable markers and other coding sequences. In some embodiments plasmids that encode a marker are composed of: (1) a high copy number replication origin, (2) a selectable marker, such as, but not limited to, the neo gene for antibiotic selection with kanamycin, (3) transcription termination sequences, including the tyrosinase enhancer and (4) a multicloning site for incorporation of various nucleic acid cassettes; and (5) a nucleic acid sequence encoding a marker operably linked to the tyrosinase promoter. There are numerous plasmid vectors that are known in the art for inducing a nucleic acid encoding a protein. These include, but are not limited to, the vectors disclosed in U.S. Pat. Nos. 6,103,470; 7,598,364; 7,989,425; and 6,416,998, which are incorporated herein by reference.

A viral gene delivery system can be an RNA-based or DNA-based viral vector. An episomal gene delivery system can be a plasmid, an Epstein-Barr virus (EBV)-based episomal vector, a yeast-based vector, an adenovirus-based vector, a simian virus 40 (SV40)-based episomal vector, a bovine papilloma virus (BPV)-based vector, or a lentiviral vector.

Markers include, but are not limited to, fluorescent proteins (for example, green fluorescent protein or red fluorescent protein), enzymes (for example, horse radish peroxidase or alkaline phosphatase or firefly/*Renilla* luciferase or nanoluc), or other proteins. A marker may be a protein (including secreted, cell surface, or internal proteins; either synthesized or taken up by the cell); a nucleic acid (such as an mRNA, or enzymatically active nucleic acid molecule) or a polysaccharide. Included are determinants of any such cell components that are detectable by antibody, lectin, probe or nucleic acid amplification reaction that are specific for the marker of the cell type of interest. The markers can also be identified by a biochemical or enzyme assay or biological response that depends on the function of the gene product. Nucleic acid sequences encoding these markers can be operably linked to the tyrosinase enhancer. In addition, other genes can be included, such as genes that may influence stem cell to RPE differentiation, or RPE function, or physiology, or pathology. Thus, in some embodiments, a nucleic acid is included that encodes one or more of MITF, PAX6, TFEC, OTX2, LHX2, VMD2, CFTR, RPE65, MFRP, CTRP5, CFH, C3, C2B, APOE, APOB, mTOR, FOXO, AMPK, SIRT1-6, HTRP1, ABCA4, TIMP3, VEGFA, CFI, TLR3, TLR4, APP, CD46, BACE1, ELOLV4, ADAM 10, CD55, CD59, and ARMS2.

Methods of differentiating iPSC to different cell types, such as retinal pigment epithelial cells, are known in the art, see for example, PCT Publication No. WO 2017/044483, which is incorporated herein by reference. Retinal pigment epithelial cells, endothelial cells, fibroblasts and pericytes can be produced from iPSC using methods known in the art.

In some embodiments, retinal pigment epithelial cells, endothelial cells, fibroblasts and pericytes can be healthy (wild-type) cells, such as from a healthy (wild-type) subject. The cells can be isolated directly, from cell lines, or produced from iPSC derived from somatic cells of a healthy (wild-type) subject. In other embodiments, one or more of the retinal pigment epithelial cells, endothelial cells, fibroblasts and pericytes are diseased cells. These cells can be isolated directly, from cell lines, or produced from iPSC, such as an iPSC derived from somatic cells from a diseased subject. Cell lines can also be utilized.

In some embodiments, a diseased cells is from a subject with a disease of interest, such as an ocular disease, for example, a retinal disease. Retinal diseases include, but are not limited to, acute macular degeneration, retinitis pigmentosa and Leber congenital amaurosis (LCA), "dry" macular degeneration, "wet" macular degeneration, late-onset retinal degeneration, Sorsby's fundus dystrophy, Stargardt's diseases, Best vitelliform macular degeneration, aniridia, microphthalmia, Joubert's syndrome, Usher syndrome, rod-cone dystrophy, night-blindness, Oguchi disease, Malattia Leventinese, cone-rod dystrophy, choroideremia, blue-cone monochromacy, or Bardet-Biedl syndrome.

In some embodiments, the cells can be treated with an agent, such as a chemical agent, to mimic the disease. In some embodiments, the cells, and/or the three dimensional ocular tissue itself, is treated with a chemical agent, such as to induce hypoxia, inflammation, oxidative stress, and/or proteotoxic stress.

In other embodiments, the retinal pigment epithelial cells, endothelial cells, fibroblasts and/or pericytes can include one or more mutations specific to a disease process. The mutations can be naturally occurring, or can be introduced using molecular methods, such as knockout, knockin, and CRISRP/Cas9 gene targeting. Thus, cells can be utilized that include recombinant nucleic acids.

In some embodiments, the retinal pigment epithelial cells, endothelial cells, fibroblasts and/or pericytes include a mutation in one or more of A2AR, A2BR, A3R, AC010973, AGT, AGTR1, AKT, APRIL, ASCC1, ATF6B, ATG, ATM, ATR, AZI2, BAD, BAFF, BCR, BCR, BECN1, BTRC, C1, C2, C2B, C3, C4, C5, CAPN6, CAPN7, CARD10, CARD6, CARD8, CAT, CCDC50, CCR3, CCR5, CD137, CD16, CD19, CD21, CD22, CD28, CD45, CD79, CDC42, CDH13, CFTR, CFTR, CNGA, CNGB, CNTFR, CRLF2, CXCR4, CYGB, DCD, DRAM, DUSP1, EDNRB, EGF, EGFR, EIF4F, ENC1, EPO, ERBB, ERK, ESR, ESR1, ESR2, FAK, FAK2, FGF, FGFR, FYCO1, GASTA2, GCAP2, GDNF, GLRX2, GRK1, GSTM1, GSTM2, GSTM3, GSTM4, GSTM5, HERPUD, HGF, HGFR, HPX, IAP, IAP, ICOS, IFN, IGFR, IL-1, IL-10, IL-12, IL-15, IL-17, IL-17, IL-19, IL-20, IL21R, IL-23, IL-23, IL-23, IL23R, IL31RA, IL-4, IL-5, IL-5, IL-6, IL-7, IL-9, IL-9, IRGM, JAB, JAK1, JAK3, JNK1, JUN, LTD4, LXR, MASP, MEF2, MEK, MGST1, MIF, MPL, MTOR, NDUFA13, NFAT, NFKB, NGF, NKAP, NKAPL, NKRF, NOD2, NOTCH1, NOX1, OSGIN1, OSGIN2, OXSR1, P38, PARK7, PDE6G, PDGF, PDGFR, PDK, PI3K, PKA, PKC, PKR, PON2, PPAR, PPM1D, PRKD1, PRLR, PTPN21, RAC, RAC, RAF, RB1CC1, RDH13, REL, RETGC, RNF25, S1P1, SCARA3, SENP6, SESN1, SHP-2, SLC24A1, SLC24A2, SNIP1, SOCS3, SOD3, SQSTM1, SRC, SREBP, STAT3, STK39, STX5, SUMO, SUMO, TANK, TBK1, TBKBP1, TCR, TGF, TGFR, TICAM, TIE2, TLR, TNF, TNFR, TNFRSF11A, TP53, TP53I3, TRPM2, TXNRD, TXNRD1, TYK2, UBE2L3, UCP3, USP2, UVRAG, VEGF, VEGFR, VNN, WDFY3, WNT, XDH, and/or ZNF382. The mutation can be engineered using molecular techniques, such as in an iPSC, or introduced directly in retinal pigment epithelial cells, endothelial cells, fibroblasts or pericytes using molecular techniques.

In some embodiments, one or more of the retinal pigment epithelial cells, endothelial cells, fibroblasts and pericytes are diseased cells from diseased human donors. The disease can be, for example, acute macular degeneration, retinitis pigmentosa or LCA. In some embodiments, the human donor can have a naturally occurring mutation in one or more of A2AR, A2BR, A3R, AC010973, AGT, AGTR1, AKT, APRIL, ASCC1, ATF6B, ATG, ATM, ATR, AZI2, BAD, BAFF, BCR, BCR, BECN1, BTRC, C1, C2, C2B, C3, C4, C5, CAPN6, CAPN7, CARD10, CARD6, CARD8, CAT, CCDC50, CCR3, CCR5, CCR5, CD137, CD16, CD19, CD21, CD22, CD28, CD45, CD79, CDC42, CDH13, CFTR, CFTR, CNGA, CNGB, CNTFR, CRLF2, CXCR4, CYGB, DCD, DRAM, DUSP1, EDNRB, EGF, EGFR, EIF4F, ENC1, EPO, ERBB, ERK, ESR, ESR1, ESR2, FAK, FAK2, FGF, FGFR, FYCO1, GASTA2, GCAP2, GDNF, GLRX2, GRK1, GSTM1, GSTM2, GSTM3, GSTM4, GSTM5, HERPUD, HGF, HGFR, HPX, IAP, IAP, ICOS, IFN, IGFR, IL-1, IL-10, IL-12, IL-15, IL-17, IL-17, IL-19, IL-20, IL21R, IL-23, IL-23, IL-23, IL23R, IL31RA, IL-4, IL-5, IL-5, IL-6, IL-7, IL-9, IL-9, IRGM, JAB, JAK1, JAK3, JNK1, JUN, LTD4, LXR, MASP, MEF2, MEK, MGST1, MIF, MPL, MTOR, NDUFA13, NFAT, NFKB, NGF, NKAP, NKAPL, NKRF, NOD2, NOTCH1, NOX1, OSGIN1, OSGIN2, OXSR1, P38, PARK7, PDE6G, PDGF, PDGFR, PDK, PI3K, PKA, PKC, PKR, PON2, PPAR, PPM1D, PRKD1, PRLR, PTPN21, RAC, RAC, RAF, RB1CC1, RDH13, REL, RETGC, RNF25, S1P1, SCARA3, SENP6, SESN1, SHP-2, SLC24A1, SLC24A2, SNIP1, SOCS3, SOD3, SQSTM1, SRC, SREBP, STAT3, STK39, STX5, SUMO, SUMO, TANK, TBK1, TBKBP1, TCR, TGF, TGFR, TICAM, TIE2, TLR, TNF, TNFR, TNFRSF11A, TP53, TP53I3, TRPM2, TXNRD, TXNRD1, TYK2, UBE2L3, UCP3, USP2, UVRAG, VEGF, VEGFR, VNN, WDFY3, WNT, XDH, and/or ZNF382.

In some embodiments, the three dimensional ocular tissue is non-innervated. In other embodiments, neurons are added and the three dimensional ocular tissue is innervated.

Optionally, the first bio-ink further can include a hydrogel. The hydrogel can be a gelatin hydrogel, a collagen hydrogel, a fibrin hydrogel, a polysaccharide hydrogel, an alginate hydrogel, a laminin hydrogel, a fibronectin hydrogel, a laminin hydrogel, a vitronectin hydrogel, a polyethylene glycol hydrogel, a gelatin methacryloyl hydrogel, or a combination thereof. In some non-limiting embodiments, the hydrogel comprises a collagen-based hydrogel.

In further embodiments, the first bio-ink further includes a first medium. Optionally, the first medium can include one or more active agents. The bioprinted structure (formed by the first bioink) can be cultured in the first medium. In some embodiments, the first medium includes thrombin, a vascular endothelial grown factor, an epithelial growth factor (EGF), a fibroblast growth factor (FGF), an insulin-like growth factor (IGF), an ascorbic acid, a hydrocortisone, a heparin sulfate, an angiopoietin-1, an aprotinin, or a combination thereof. Additional agents are disclosed above.

The first medium can include an effective amount one or more of vascular endothelial growth factor (VEGF), angiopoietin-1 (ANG-1), aprotinin, epidermal growth factor (EGF), insulin-like growth factor (IGF), and fibroblast growth factor (FGF). Thus, the first medium can include one, two, three, four, five or all six of these factors. Exemplary concentrations of EGF are 1-50 ng/ml. Exemplary concentrations of FGF are 1-1,000 ng/ml, and exemplary concentrations of IGF-1 are 1-500 ng/ml. In some embodiments, the first medium includes vascular endothelial cell growth factor (VEGF), angiopoietin 1, IGF, EGF, FGF, ascorbic acid, hydrocortisone, heparin sulfate, angiopoietin, and aprotinin. In specific non-limiting examples, the first medium includes 1-1,000 ng/ml of VEGF, 50-1000 ng/ml of angiopoietin 1, and 0.075-0.5 U/ml of aprotinin. In other specific non-limiting examples, the first medium includes 100 ng/ml ANG-1, 0.075 U/ml aprotinin. In additional embodiments, the first medium includes an effective amount of EFG, IGF, FGF, ascorbic acid, hydrocortisone, and heparin sulfate. In further embodiments, the first medium includes thrombin, such as 0.5 U/ml to 10 U/ml, such as 0.5 U/ml or 1 U/ml. In a specific, non-limiting example, the first medium can include 1-1,000 ng/ml of endothelial cell growth factor (VEGF), 50-1000 ng/ml of angiopoietin 1, and 0.075-0.5 U/ml of aprotinin.

The bioprinted structure (formed by the first bioink) can be cultured in a second medium. In some embodiments, the first layer and/or the second layer of the three-dimensional engineered outer BRB are cultured in the second medium. The second medium can include an effective amount one or more of vascular endothelial growth factor (VEGF), angiopoietin-1 (ANG-1), aprotinin, epidermal growth factor (EGF), insulin-like growth factor (IGF), and fibroblast growth factor (FGF). Thus, the second medium can include one, two, three, four, five or all six of these factors. In a specific non-limiting example, the second medium includes all of these factors. Exemplary concentrations of EGF are 1-50 ng/ml. Exemplary concentrations of FGF are 1-1,000 ng/ml, and exemplary concentrations of IGF-1 are 1-500 ng/ml. An exemplary medium including these factors is disclosed below. In some embodiments, the second medium includes vascular endothelial cell growth factor (VEGF), angiopoietin 1, IGF, EGF, FGF, ascorbic acid, hydrocortisone, heparin sulfate, angiopoietin, and aprotinin. In specific non-limiting examples, the second medium comprises 1-1,000 ng/ml of VEGF, 50-1000 ng/ml of angiopoietin 1, and 0.075-0.5 U/ml of aprotinin. In other specific non-limiting examples, the second medium includes 100 ng/ml ANG-1, 0.075 U/ml aprotinin. In additional embodiments, the second medium includes an effective amount of EFG, IGF, FGF, ascorbic acid, hydrocortisone, and heparin sulfate. In further embodiments, the first medium and/or the second medium include thrombin, such as 0.5 U/ml to 10 U/ml, such as 0.5 U/ml or 1 U/ml. In some embodiments, the second medium comprises a vascular endothelial growth factor, an EGF, an FGF, an IGF, an ascorbic acid, a hydrocortisone, a heparin sulfate, an angiopoietin-1, an aprotinin, or a combination thereof.

The bioprinted structure (formed by the first bioink) can be cultured in a third medium. In some embodiments, the first layer and/or the second layer of the three-dimensional engineered outer BRB are cultured in the third medium. The third medium can include a taurine-hydrocortisone-triiodo-thyronin, a hydrocortisone, a triiodo-thyronin, a fetal bovine serum, or a combination thereof. In some embodiments, the bioprinted structure is cultured sequentially in the first medium, second medium, and/or third medium.

The ocular tissue model can include a first layer that is deposited by bio-printing. Bio-printing can include extrusion of the first bio-ink onto a first surface of the biocompatible scaffold.

In some embodiments, the ocular tissue model can be used in one or more of: drug discovery, drug testing, preclinical research, toxicity testing, absorption, distribution, metabolism, and excretion testing (ADME), drug metabolism and pharmacokinetics testing (DMPK), disease modeling, infectious disease modeling, host disease modeling, three-dimensional biology studies, cell-based screening, gene therapy testing, and biomarker discovery. In other embodiments, the ocular tissue model is for use in implantation into an eye of a human subject, see below. In further embodiments, the wherein the ocular tissue model is substantially free of the biocompatible scaffold at the time of use.

In some embodiments, a kit is provided. The kit that can include, for example, one or more media and components for the production of a three-dimensional, engineered ocular tissue model. The reagent system may be packaged either in aqueous media or in lyophilized form, where appropriate. In other embodiments, a kit is provided that include the three-dimensional, engineered ocular tissue model itself.

The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be contained in a vial.

One or more components of the kit, such as a medium, may be provided as dried powder(s). When reagents and/or components are provided as a dry powder, the powder can be reconstituted by the addition of a suitable solvent. It is envisioned that the solvent may also be provided in another container means.

The kits also will typically include a means for containing the kit component(s) in close confinement for commercial sale. Such containers may include injection or blow molded plastic containers into which the desired vials are retained. The kit can also include instructions for use, such as in printed or electronic format, such as digital format.

Methods of Treatment

The disclosed three-dimensional engineered BRB comprising a choroid and retinal pigmented epithelial cells can be used to treat macular degeneration, such as age-related macular degeneration, macular dystrophies such as Stargardt's and Stargardt's-like disease, Sorsby's Fundus Dystrophies, RPE tear, Choroidal Neovascularization, Best disease (vitelliform macular dystrophy), and adult vitelliform dystrophy or subtypes of retinitis pigmentosa, are associated with a degeneration or deterioration of the retina itself, or physical injury or trauma to the retina, choroid, or RPE cells. Age-related macular degeneration (AMD) is a leading cause of blindness among people over 55 years of age; this disease is caused by genetic and environmental factors. AMD progresses from the dysfunction and death of retinal pigment epithelium (RPE) cells to photoreceptor loss and deficits in sharp vision. Transplantation of functional RPE cells can be used to replace the retinal pigment epithelium monolayer. Studies have shown, however, that injection of cell suspensions was not successful, because the transplanted cells died within two weeks, and the monolayer structure that is essential to RPE function was never formed. Therefore, injection of single cell suspension of RPE is not effective. The methods disclosed herein provide an engineered BRB comprising a choroid and retinal pigmented epithelial cells that can be transplanted into the eye, recapitulating the endogenous structure.

Methods are disclosed herein for treating symptoms of a retinal degeneration in a patient, for example, by implanting in one or both eyes the engineered BRB, including the choroid and retinal pigment cells, as disclosed herein. In one embodiment, the Symptoms of AMD include, for example, choroidal new vessel growth (CNV), atrophy of the fovea, atrophy of the subfoveal retinal pigment epithelium, atrophy of the choroid, and/or loss of central vision. In the early stages of AMD, it may sufficient to replace only RPE cells, for example, by implanting the engineered BRB disclosed herein. Without being bound by theory, the implanted RPE cells may mediate prevention of further loss of RPE cells and/or degeneration of the Bruch's membrane. At advanced stages of AMD, patients may experience loss of both RPE cells and photoreceptor cells. Thus, in some embodiments, the methods can further comprise implanting compositions comprising photoreceptor cells. Methods for transplanting a scaffold and RPE cells are disclosed, for example, in PCT Publication No. WO 2012177968 and PCT Publication No. 2016/007852, which are both incorporated herein by reference.

The size of the composition to be implanted may be generally determined by comparing the clinical assessment of the size of the region of retinal pathology present in a particular patient, with the constraints imposed by surgical feasibility of delivering an implant of a particular size. For example, in degenerations involving the central retina (e.g., age-related macular degeneration), a circular implant of from about 1.0-2.5 mm diameter (e.g., of about 1.5 mm diameter) that approximates the anatomic fovea will frequently be appropriate. In some cases, larger implants may be appropriate, maximally corresponding to the area of posterior retina lying between the temporal vascular arcades (histologic macula, clinical posterior pole) which is an ovoid area of approximately 6.0 mm (vertical)×7.5 mm (horizontal) centered on the fovea or positioned in the extra-foveal region. In some instances, it may likewise be appropriate to fashion a polymer scaffold of smaller dimension, as small as about 0.5 mm, to be placed in an area of circumscribed pathology. In addition, it may be of interest to custom fashion implants of irregular shape to suit the patient, for instance to cover areas of pathology while avoiding areas of residual high vision.

In some embodiments, the methods include administering an immunosuppressive agent that reduces an immune response, for example, by downregulating the response of inflammatory cells or by inducing apoptosis of inflammatory cells. In other embodiments, the method includes administering a therapeutically effective amount of a neuroprotective agent that promotes survival and/or reduces degeneration of retinal neurons. In yet other embodiments, the method can include administering a therapeutically effective amount of an agent to inhibit unwanted angiogenesis, for example, to counteract the choroidal new vessel (CNV) growth under the fovea in AMD patients. An exemplary therapeutic agent can reduce activity of vascular endothelial growth factor (VEGF), for example, by binding to the receptor site of active forms of VEGF and preventing interaction of VEGF with its receptors. A therapeutically effective amount of and that suppresses the expression of VEGF by inhibiting pathways leading to VEGF secretion, such as STAT3, NF-kB, HIF-1α. Other drugs can prevent atrophy of RPE cells by targeting complement pathway, autophagy, or NF-kB pathways.

In further embodiment, the method includes administering to the subject a therapeutically effective amount of Ciliary Neurotrophic Factor (CNTF), Brain-Derived Neurotrophic Factor (BDNF), or Pigment Epithelial Derived Factor (PEDF), which can be used, for example, to promote development or function of neurons such as photoreceptor cells. Other exemplary, non-limiting embodiments include administering to the subject a therapeutically effective amount of thrombospondin 1, an anti-inflammatory cytokine (for example, interleukin (IL)-1ra, IL-6, Fas ligand or tumor growth factor (TGF)-beta, a neurotrophic/neuroprotective growth factor such as, but not limited to, glial cell line-derived growth factor, brain-derived neurotrophic factor, nerve growth factor, neurotrophin-3, -4/5, -6, and vitamin E. Such agents may be provided singly or in combination.

Screening Methods

Methods are provided herein for determining the effect of a test agent. The method includes contacting a three-dimensional engineered BRB comprising a choroid and retinal pigmented epithelial cells produced by the methods disclosed herein with the test agent. A phenotype of cells within the choroid is then evaluated. For example, a phenotype of the RPE cells or the capillaries formed by the endothelial cells can be evaluated. In further embodiments, the three-dimensional structure of the choroid with retinal pigment epithelial cells is evaluated. A change in the phenotype of the cells and/or a change in the three-dimensional structure indicates that the agent has an effect. A positive effect can be form example, maintenance of the barrier functions of the RPE cells, or increased survival or one or more of the cell types. A negative effect of the test agent can be death of RPE cells, a decrease in barrier function, capillary disassociation, overgrown capillaries or invasion of the capillaries into the RPE layer. The choroid can also be evaluated, such as to determine if it is disassociating. In addition, pericytes can be evaluated to determine if they are coating the vessels.

The test compound can be any compound of interest, including chemical compounds, small molecules, polypeptides, growth factors, cytokines, or other biological agents (for example antibodies). In several examples, a panel of potential neurotrophic agents are screened. In other embodiments a panel of polypeptide variants is screened.

Methods for preparing a combinatorial library of molecules that can be tested for a desired activity are well known in the art and include, for example, methods of making a phage display library of peptides, which can be constrained peptides (see, for example, U.S. Pat. Nos. 5,622, 699; 5,206,347; Scott and Smith, *Science* 249:386-390, 1992; Markland et al., *Gene* 109:13-19, 1991), a peptide library (U.S. Pat. No. 5,264,563); an FDA-approved drug library (see, for example, Huang, E; Southall, N; Wang, Y et al., *Science Translational Medicine* 3: 1-12); a peptidomimetic library (Blondelle et al., *Trends Anal Chem.* 14:83-92, 1995); a nucleic acid library (O'Connell et al., *Proc. Natl Acad. Sci., USA* 93:5883-5887, 1996; Tuerk and Gold, *Science* 249:505-510, 1990; Gold et al., *Ann. Rev. Biochem.* 64:763-797, 1995); an oligosaccharide library (York et al., *Carb. Res.* 285:99-128, 1996; Liang et al., *Science* 274: 1520-1522, 1996; Ding et al., *Adv. Expt. Med. Biol.* 376: 261-269, 1995); a lipoprotein library (de Kruif et al., *FEBS Lett.* 3 99:23 2-23 6, 1996); a glycoprotein or glycolipid library (Karaoglu et al., *J Cell Biol.* 130.567-577, 1995); or a chemical library containing, for example, drugs or other pharmaceutical agents (Gordon et al., *J Med. Chem.* 37.1385-1401, 1994; Ecker and Crooke, *BioTechnology* 13:351-360, 1995). Polynucleotides can be particularly useful as agents that can alter a function of cells (such as, but not limited to endothelial cells and fibroblasts and RPE cells) because nucleic acid molecules having binding specificity for cellular targets, including cellular polypeptides, exist naturally, and because synthetic molecules having such specificity can be readily prepared and identified (see, for example, U.S. Pat. No. 5,750,342).

In one embodiment, for a high throughput format, three-dimensional engineered BRBs comprising a choroid and retinal pigmented epithelial cells can be introduced into wells of a multi-well plate or of a glass slide or microchip, and can be contacted with the test agent. Generally, the BRBs are organized in an array, particularly an addressable array, such that robotics conveniently can be used for manipulating solutions and for monitoring cells in the BRB, particularly with respect to the function being examined. An advantage of using a high throughput format is that a number of test agents can be examined in parallel, and, if desired, control reactions also can be run under identical conditions as the test conditions.

As such, the methods disclosed herein provide a means to screen one, a few, or a large number of test agents in order to identify an agent that can alter a function of cells, for example, an agent that induces the cells to differentiate into a desired cell type, or that affects differentiation, survival and/or cell proliferation. High throughput screens can be used to assess phenotype and survival. These screens can be used to identify drugs that can affect RPE phenotype and survival, or endothelial cell proliferation and survival. Architecture of the BRB can also be examined.

The engineered BRB can also be used for image-based assays, measurement of secreted proteins, expression of markers, and production of lipids, proteins or mRNAs. In various further embodiments, the engineered BRB are for use in assays to detect or measure one or more of: barrier function, molecular binding (including radio ligand binding), molecular uptake, activity (e.g., enzymatic activity and receptor activity, etc.), gene expression, protein expression, protein modifications (non-limiting examples include: phosphorylation, ubiquitination, acetylation, glycosylation, lipidation, etc.) receptor agonism, receptor antagonism, cell signaling, apoptosis, DNA damage, stress response, cohesion, permeability, inflammation, pigmentation, chemosensitivity, transfection, cell migration, chemotaxis, cell viability, cell proliferation, safety, efficacy, metabolism, toxicity, infectivity, and abuse liability. In various embodiments, the engineered BRB can be used for toxicology, pharmaceutical or cosmetic testing.

3D Printing Inserts

A 3D printing insert is also provided in some embodiments to facilitate bioprinting of the scaffold. The specialized insert can be used in lieu of the modified TRANSWELL® permeable support, see Example 2. The inserts are adapted to fit securely in a culture well (such as a cylindrical culture well) while providing an exposed printing frame (for example a rectilinear frame opening, such as a square or rectangular frame opening) that frames a substrate contained within the insert. The insert has a length that is substantially the same as the inner diameter of the culture wells to enable the insert to fit in and be securely retained within the culture well. Outer walls of the insert are curved to be complementary in shape and/or size to the walls of the well in which it seats. The insert body also has a central collar in which the printing substrate seats, and into which a support structure (such as a cylindrical end of the holder) can press against the substrate to retain the substrate firmly in place against the frame support structure. A plurality of ports extend through the body of the insert to establish fluid communication between the circular recess and the exterior of the insert body for introducing liquid media through the walls of the insert body.

For example, the insert has a central collar of any shape (such as circular or square) that circumscribes the printing frame, and the insert is matable with a holder that is retainable in the central collar to hold the scaffold within the central collar to securely maintain the fixed position of the scaffold in the printing frame. The insert may have a plurality of spacer arms, for example two arms, that extend radially from the collar a sufficient distance for placement against the wall of the chamber, and the arms terminate in a surface that conforms to the shape of the wall of the chamber. If the wall of the chamber is curved, the arms terminate in a curved surface that is complementary to a curve of the wall. In some embodiments the chamber is a culture dish and the arms extend substantially symmetrically from the collar a sufficient distance to position the well centrally within the culture dish. In some examples the culture well is present in a multi-well-plate.

In some disclosed embodiments, the aperture that forms the printing frame is polygonal and of a sufficient size to be circumscribed by the collar, and the collar is of sufficient size to retain the scaffold when the scaffold is larger than the aperture. For example, when the collar is cylindrical the printing frame may be rectangular and surrounded by the collar. In certain examples, inlet and outlet ports extend through the insert for infusing culture media into and through the insert, then through the frame aperture, and out of the insert body to circulate the culture media through the substrate to nourish cells growing on the substrate into the frame aperture. The scaffold may, for example, be a sheet shaped to fit against an inside wall of the collar so that cells may be grown on both faces (upper and lower) of the sheet as the tissue media is supplied to the substrate.

In certain embodiments, a holder is inserted within the collar to retain the scaffold securely against the aperture of the printing frame. In some disclosed examples, the holder is funnel-shaped and comprises a frustoconical body and a narrower cylindrical stem. The cylindrical stem fits within the collar of the insert when the substrate is positioned against the frame aperture to retain the substrate against the aperture. The body of the funnel can be used to manipulate and/or position the substrate in a bioprinting orientation with the substrate exposed through the aperture. In some examples, methods of using the insert include placing the scaffold in the collar of the insert with the scaffold abutting and exposed through the aperture of the printing frame. The holder is inserted into the collar of the insert body and against the scaffold to retain the printing scaffold securely against the frame to restrain it against movement during bioprinting as cellular layers are carefully positioned in three-dimensional space on the surface of the substrate. The scaffold is desirably of a size that conforms to and fits within the collar of the insert body. For example, the scaffold is a thin circular sheet have an outer diameter slightly less than the inner diameter of the cylindrical collar of the insert to permit the sheet to fit securely within the collar and be held in a stationary position against the aperture of the printing frame through which one face of the scaffold sheet is exposed. The cylindrical stem of the holder is then inserted into the collar against the aperture of the printing frame, and the cylindrical stem of the holder is inserted into the collar until the leading edge of the stem abuts against the scaffold to retain the scaffold exposed in the printing frame in a fixed position.

The holder is then used to withdraw the insert from the culture well, orient the insert with the bioprinting frame exposed to a printer head, and bioprint on the scaffold through the printing frame. For example, the holder is grasped to withdraw the insert from the culture well, and the funnel is placed on a support surface below a three-dimensional (3D) bio-printer head. The holder may be positioned on the support surface with the substrate precisely aligned in position (for example horizontally) below the bio-printer head for bioprinting of cells on the surface of the sheet that forms the substrate, and then bioprinting on the substrate through the aperture of the printing frame. In some examples, the method also includes seeding or bioprinting on an opposite face of the scaffold that is not exposed through the frame to create a multilayer artificial tissue. The opposite face of the substrate can be seeded or bioprinted through the holder, for example through the funnel of the holder. Once the cells are present on one or both faces of the substrate, the insert is placed back in the culture well and culture media is infused through the ports of the insert into the printing frame to supply nutrients to the bioprinted cells. Alternatively, the infusion ports are absent and culture media is added to the culture well and/or through the funnel of the holder.

The inserts can be any shapes and made from any biocompatible materials as long as the insert can hold the printed tissue. The peripheral surface of the insert can have any desirable shape, such as curved, square or irregular. The printing frame, although illustrated as square or rectangular, can be any shape, such as a polygon (for example a pentagon or hexagon) or round (such as a circle or oval shape). The collar that surrounds the printing frame can also be any variety of shapes and cross-sections, for example a polygonal (such as a rectangular, pentagonal or hexagonal) cross-section or a circular or ovoid cross-section. Also the insert can have any number of premade channels for perfusion, or none at all.

Specific examples of the inserts are shown in FIGS. 3A-3G. The inserts are generally thin and have a central support body and peripheral portions that are shaped to retain the insert at a central location in a well in which the insert is placed. The insert body includes a cylindrical recess in the top of the insert body into which is to be inserted a holder having an engagement portion of complementary shape to firmly engage the insert with the holder. The cylindrical recess circumscribes and communicates with an underlying cuboidal or other shaped-recess in the bottom face of the insert that provides, for example, a rectangular printing frame around the face of the scaffold that is to be printed.

The scaffold that serves as the printing substrate is placed in the cylindrical recess with one face of the scaffold sheet resting against and exposed through the underlying square recess that forms a printing frame around the face of the scaffold that is to be printed. A curved (for example cylindrical) engagement portion of the holder is then placed in the cylindrical recess of the insert with the edges of the holder engaged against the walls of the cylindrical recess, and the leading edge of the cylindrical portion of the holder abutting the scaffold to hold the scaffold firmly in place. As in FIG. 1G, the insert is then inverted so the printing frame points upwardly with one face of the scaffold sheet exposed through the rectangular frame. The holder supports the scaffold over a working surface as one or more printing needles deposit the bio-ink on the substrate in a desired pattern, for example in spaced parallel rows on the substrate.

In an embodiment of the spacer shown in FIG. 3D, insert 30 is shaped to fit snugly against the walls of a cylindrical well, such as the walls of wells (not shown) in a 6 well culture plate. The insert is elongated so that it has a length that is capable of extending between the walls of a culture well. Insert 30 has a central rectangular body 32 that flares in width to form peripheral arms 34, 36 each of which has smooth curved outer surfaces such as arcuate surface 38. Arm 36 has a similar smooth curved outer face. The length of insert 30 (central body plus arms) is substantially the same as the diameter of the well in which insert 30 fits, and the curvature of the arcuate surfaces of arms 34, 36 is complementary to the curvature of the walls of the well in which it is designed to seat. A central opening in the upper face of body 32 is partially formed by a cylindrical recess 40 that forms a collar that extends through only part of the height of insert 30. Cylindrical recess 40 circumscribes and communicates with a cuboid-shaped recess 42 in the bottom face of body 32 such that recesses 40, 42 cooperatively form the central opening extending completely through body 32, and recess 42 forms a frame for bioprinting a substrate. Multiple ports 44, 46 and 48 extend through body 32 above recess 42 from the exposed longitudinal edge of body 32 to communicate with cylindrical recess 40. Each of these ports enters the side wall of insert 30, opens into an edge of recess 42, and then continues through mirror image ports in an opposing edge of recess 42 and out of insert body 32. In this manner, a continuous flow path is established for the optional infusion of culture media into the insert and through the aperture to supply nutrients to cells that are to be cultured on the substrate when the substrate is positioned in the insert.

The cuboid-shaped recess 42 can be of other than a cuboid-shape, for example any parallelepiped or rectangular parallelepiped, a hemisphere, tetrahedron or any other shape that presents a frame border around the substrate that is mounted in the recess 40. Similarly, cylindrical recess 40 can be of any shape that is complementary to and capable of mating with a portion of the holder to help attach the holder to the insert.

In use, the printing substrate (not shown) is prepared to be of similar diameter but lesser height than cylindrical recess 40. The substrate is placed tightly into cylindrical recess 40, and a cylindrical mating portion of the holder is inserted into recess 40 on top of the substrate to connect the holder to the insert and firmly press the substrate against the inside of frame 42. Insert 30 is then inverted from the orientation shown in FIG. 3D so that it is supported on a working surface by the holder, and the surface of the substrate that is exposed through rectangular-shaped frame formed by recess 42 is bioprinted. After bioprinting of the exposed surface is complete, the insert is then reoriented with the holder above it in a culture well, with the bioprinted substrate surface facing the bottom of the well. Culture media is then infused through ports 44, 46, 48 to allow cells on the bioprinted surface to grow toward the bottom of the well. Mirror image ports exist on opposite edges of square recess 42, which allows the culture media to flow into one set of ports along a first edge of recess 42 and out of the corresponding set of the ports on an opposite edge of recess 42.

Figure 3B:
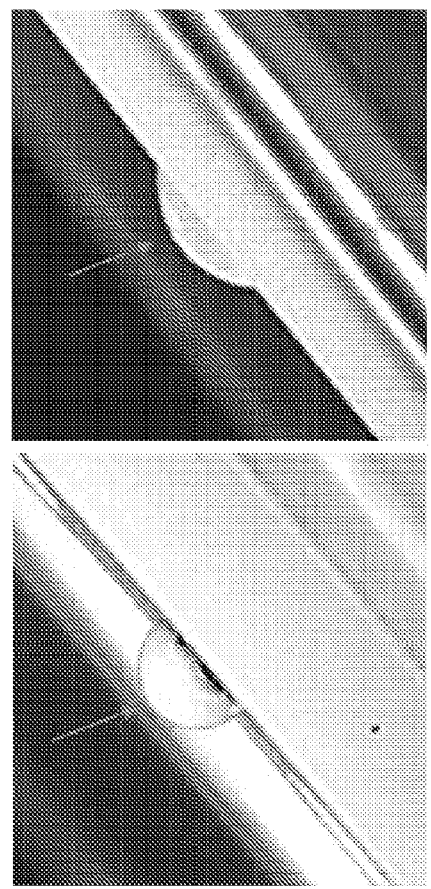
Figure 3C:
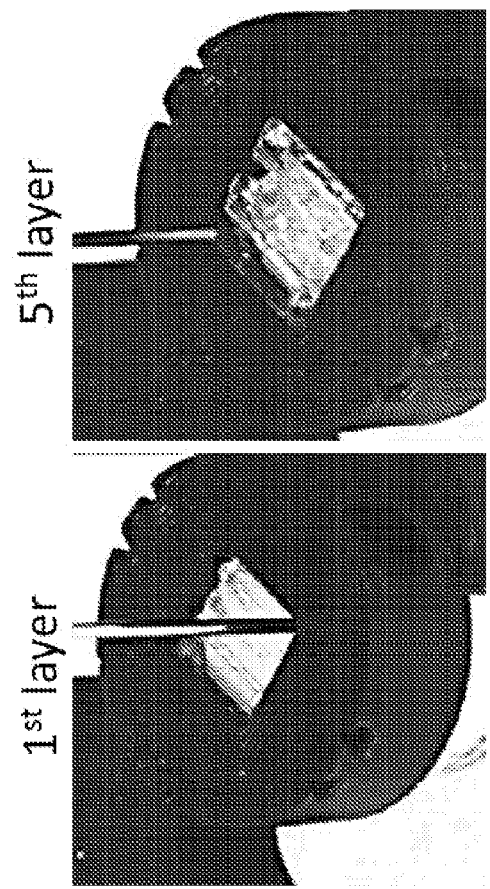
Figure 3A:
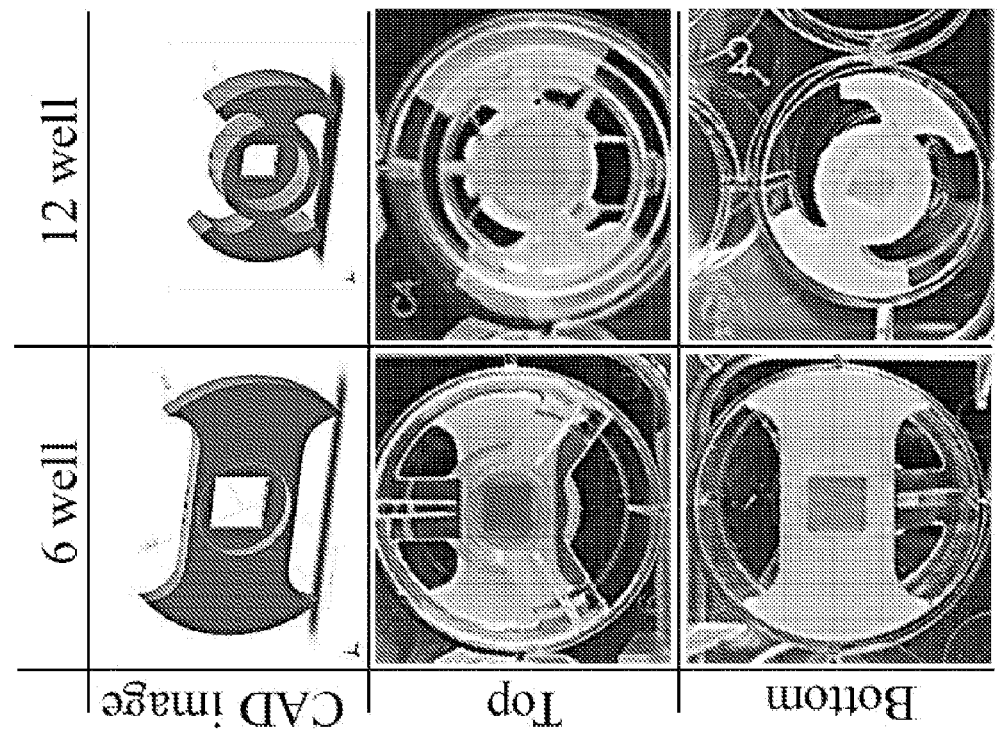
Figure 3E:
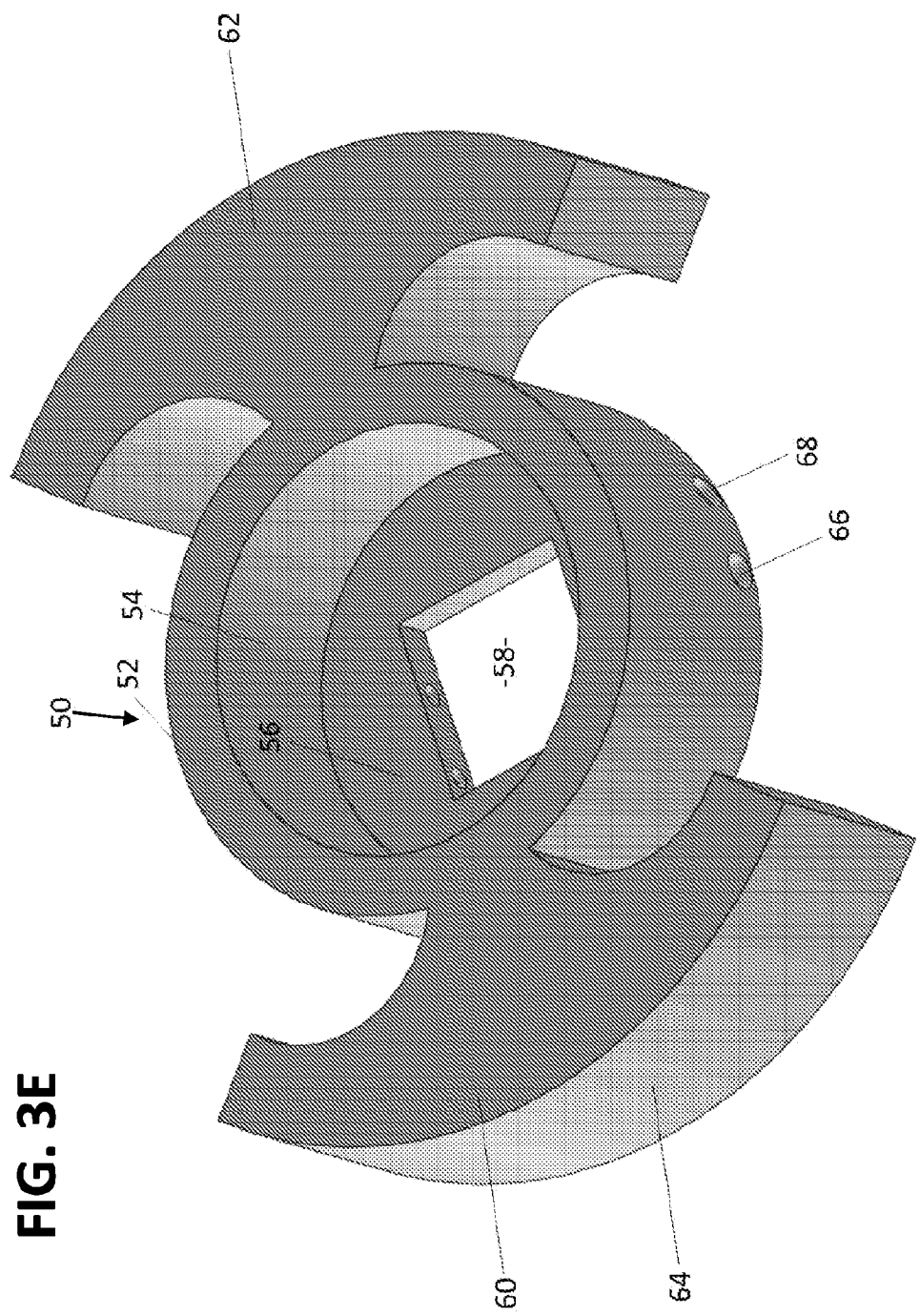

In a second embodiment shown in FIG. 3E, insert 50 has a central body that includes a cylindrical collar 52 that forms an internal cylindrical recess 54 with a lower face 56 in which is located a central cuboid-shaped recess 58 that forms a square frame border. First and second spacer arms 60, 62 form wedges that extend radially from collar 52 as a narrow attachment throat to a circumferentially enlarged external surface of the arms such as surface 64. The circumferentially enlarged surface of the arms has a curved shape that is complementary to the curvature of a culture well. A pair of ports 66, 68 extend from the outer wall of collar 52 through the bottom of cylindrical recess 54 to communicate with outlet ports on a first edge of frame 58. A mirror image set of outlet ports is positioned on an opposite edge of square recess 58 and extend through the central body below surface 56 to exit on the outer wall of the collar.

Figure 3F:
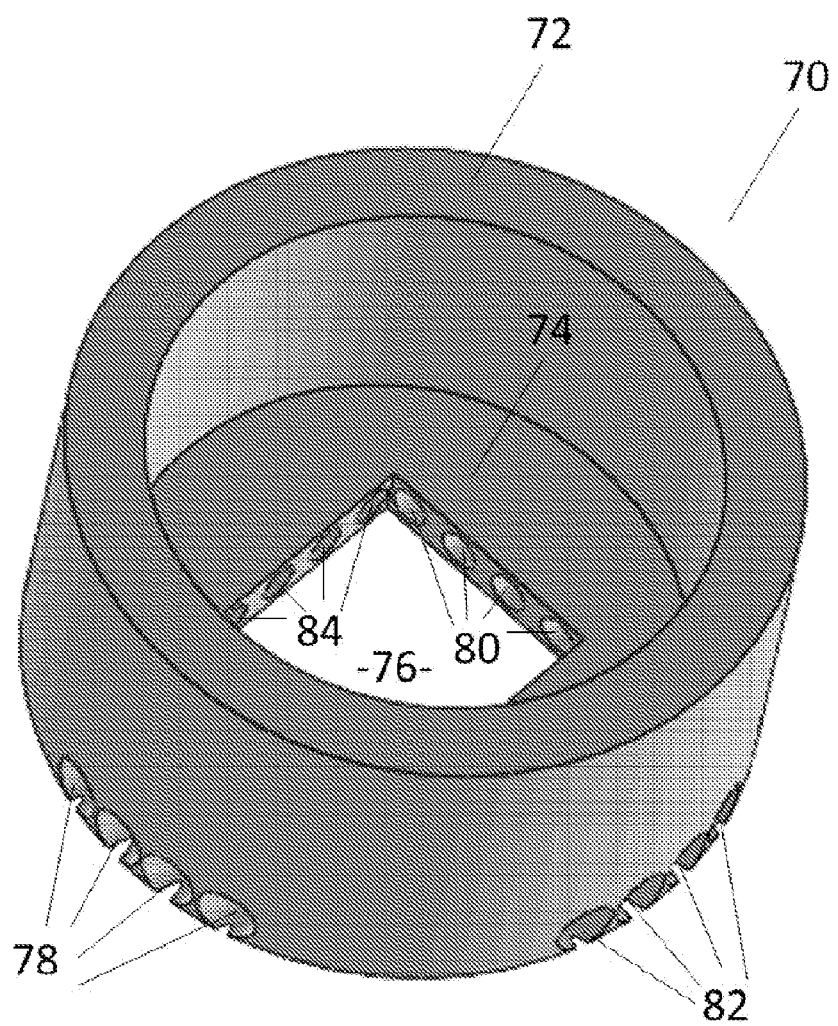
Figure 3H:
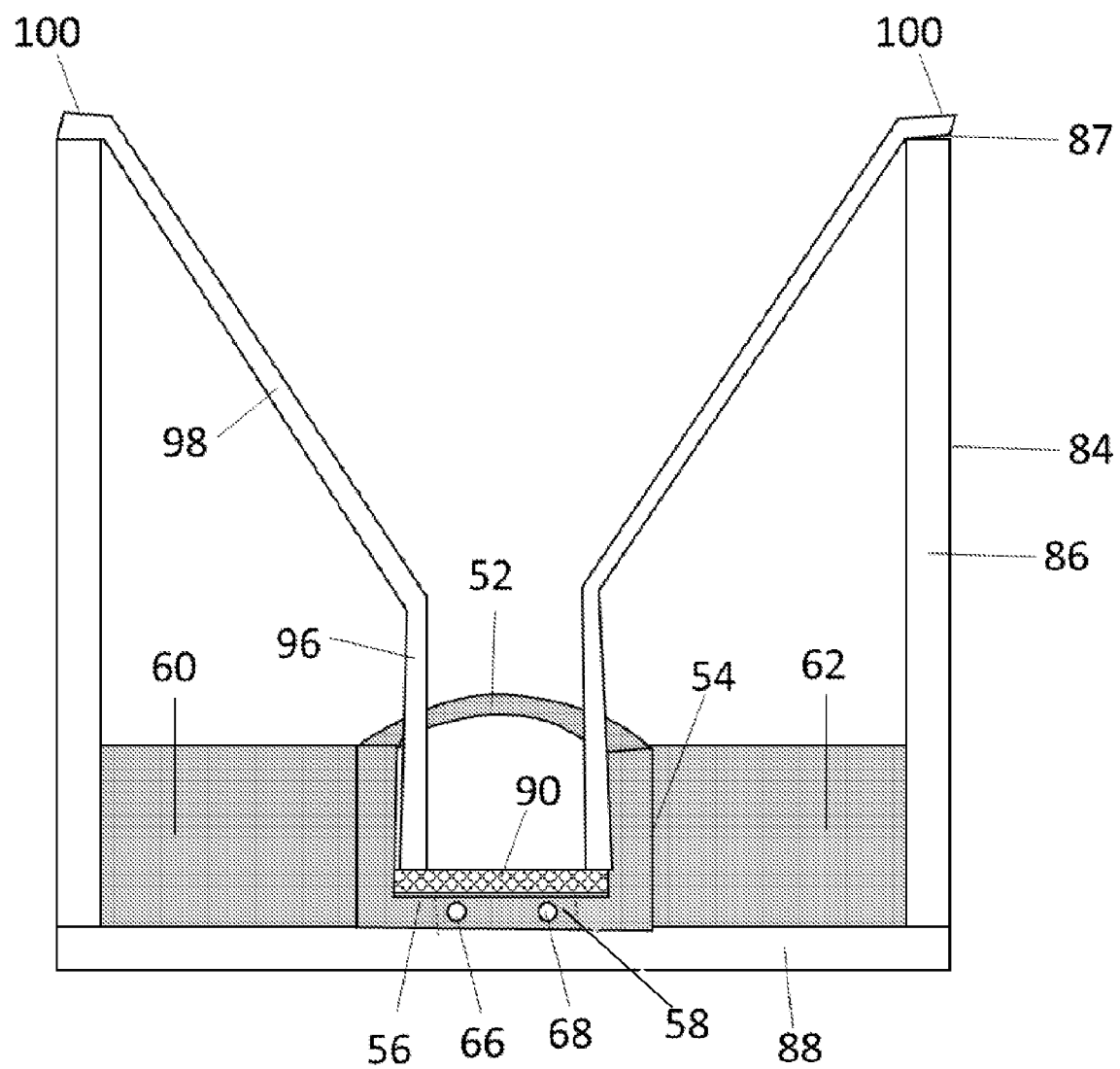
Figure 4:
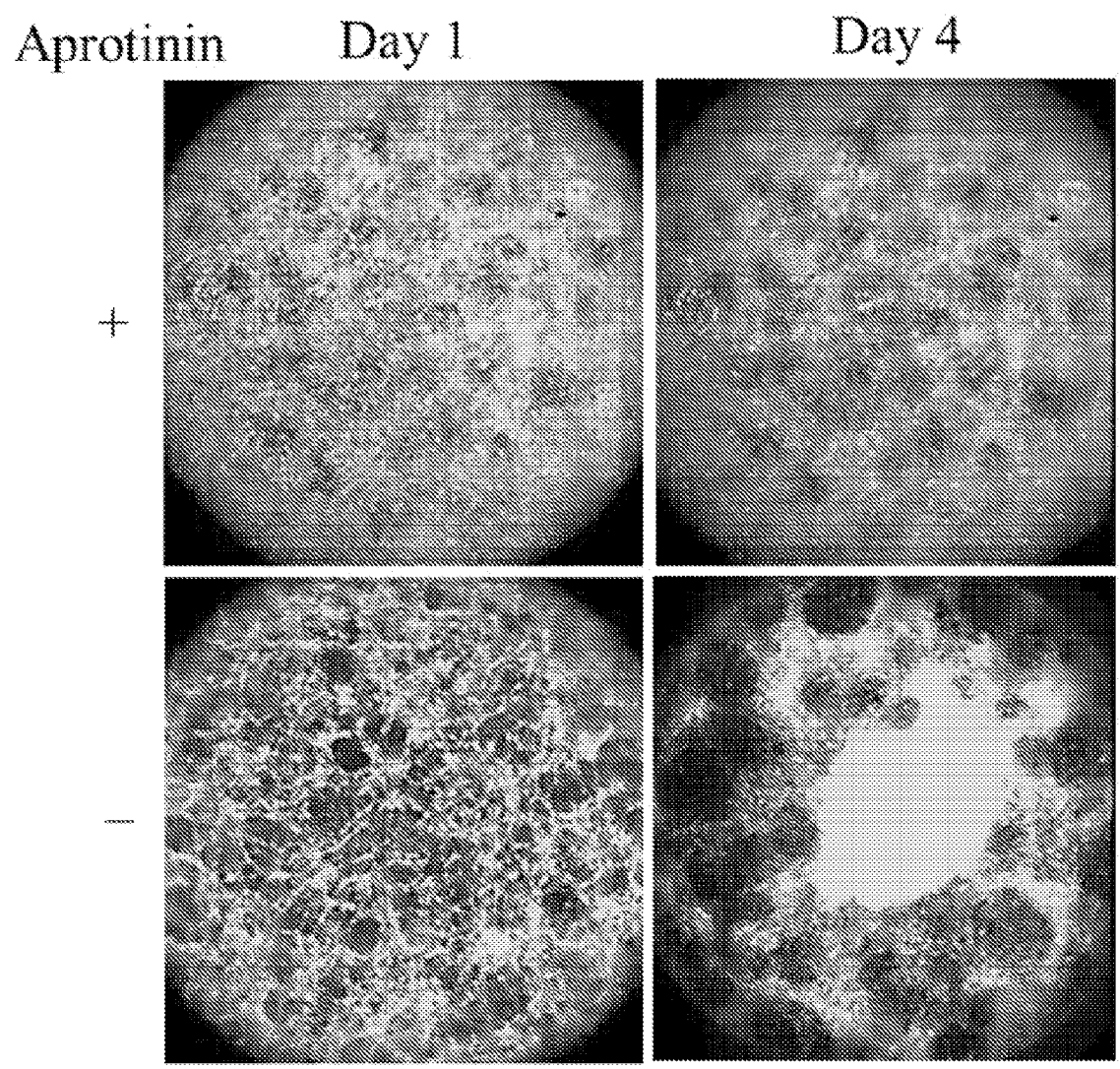
FIG. 4 shows photomicrographs demonstrating the effects of fibrin gel degradation on endothelial cells (2.5 mg/ml). Endothelial cells (4 million cells/ml) were seeded within a 24 multiwell plate. Each image represent entire well.
Figures 5A, 5B:
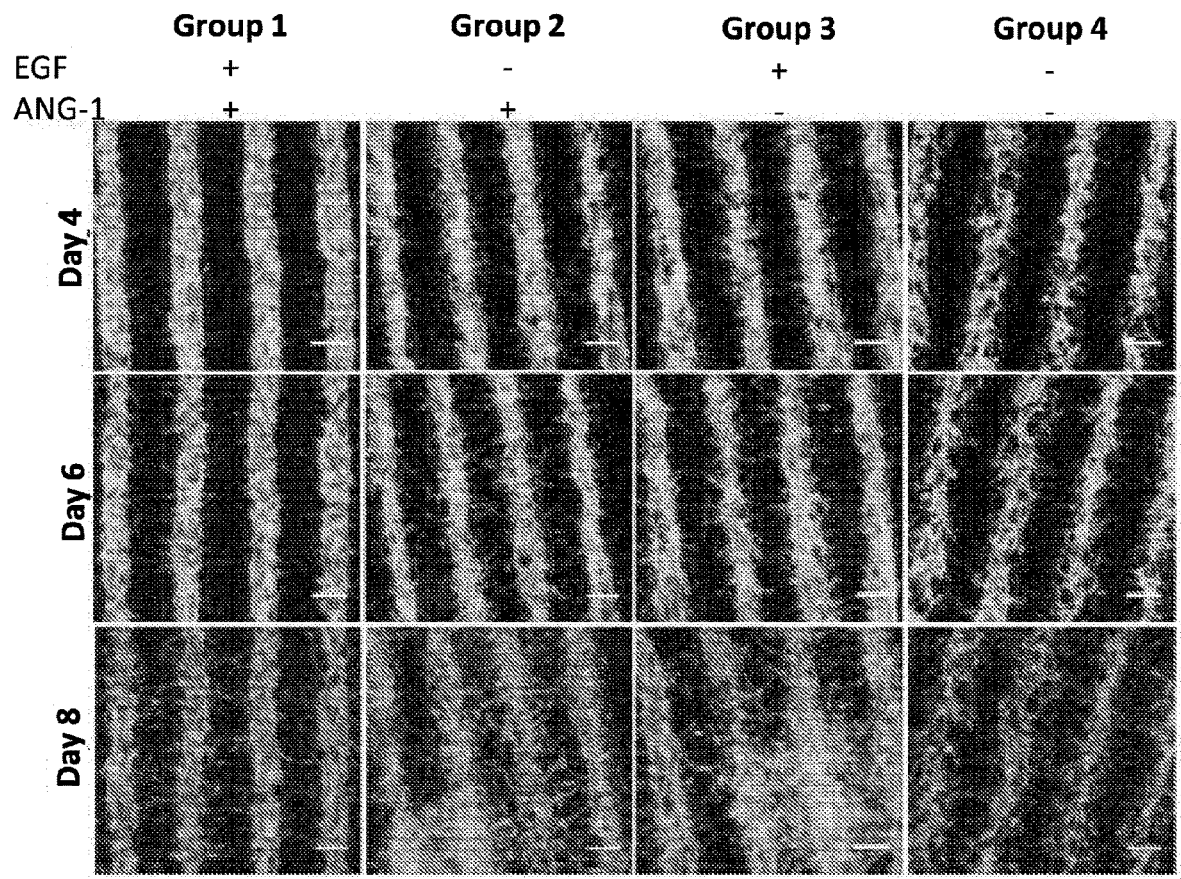

Use of insert 50 is illustrated in FIGS. 3G and 3H in which insert 50 is shown wedged into the bottom of a culture well 84. Culture well 84 is cylindrical and has a continuous side wall 86 with an annular upper lip 87, and a flat bottom wall 88. The flat bottom face of insert 50 is seated on bottom wall 88 of well 84, and arms 60, 62 of insert 50 extend radially outwardly from collar 52 to position the collar centrally in well 84. A circular sheet of printing substrate 90 is placed in the bottom of collar 52 on lower face 56 and is held in place by a funnel-shaped holder 94 that has a cylindrical stem portion 96 and an upper frustoconical funnel portion 98 that terminates at its top edge in an angled peripheral flange 100 that seats on annular upper lip 87 of well 84. Cylindrical portion 96 of holder 94 fits tightly against the inner walls of collar 52 to firmly press substrate 90 against the printing frame formed by square recess 58.

Holder 94 and its attached insert may then be inverted from the orientation shown in FIG. 3H (as in FIG. 1G) to display an upwardly-facing printing frame and printing substrate 90 for bioprinting. For example, peripheral flange 100 of funnel portion 98 is seated on a flat support surface so that funnel-shaped holder firmly orients itself on the support surface. Holder 94 thereby supports substrate 90 in the frame spaced above the support surface for bioprinting. Once printing is completed, holder 94 may be once again inverted and returned to the culturing orientation shown in FIG. 3H in culture well 84. Culture media may be infused through ports 66, 68 and through square recess 58 to provide additional nutrients to the printed bio-tissue as it grows into square recess 58 toward culture plate bottom wall 88. With holder 94 in the orientation shown in FIG. 3G, additional cells may be seeded on to the surface of substrate 90 that is exposed within collar 52. In specific disclosed examples, vascular cells are printed on substrate 90 through the printing frame recess 58, and RPE cells are seeded on to the opposite surface of substrate 90 through holder 94, for fabricating a three-dimensional engineered blood retinal barrier (BRB) comprising a choroid on one face of the substrate and retinal pigment epithelial cells on its other face.

In a third embodiment shown in FIG. 3F, insert 70 is a cylindrical collar 72 of a size and shape that fits tightly into a culture well in which it is to be used. Collar 72 has a bottom wall 74 with a flat upper and parallel flat lower surface. A square printing frame 76 extends through bottom wall 72 and is circumscribed by collar 72. A series of ports 78, 82 are arranged around the exterior of collar 72 and communicate with ports 80, 84 around the interior of frame 76 to permit culture media to be infused through the ports into and through printing frame 76. Some of the ports are used to introduce the culture media into frame 76 and other ports permit the culture media to flow out frame 76.

EXAMPLES

Human iPS cell technology combined with in vitro development and tissue engineering approaches allow the possibility of developing potential cellular and tissue therapies for patients with severe degenerative diseases or with severe damage caused by an injury. Additionally, iPS cells can be derived in a patient-specific manner and can be used to develop autologous tissue that will likely evade immune-rejection. Bioprinting technology can be used to build complex 3D structures involving multiple cell types. It uses two features: (1) cells seeded in the form of large droplets as "bio-ink" that contains several hundred to a few thousand cells (for example 200-2000 cells) mixed with degradable biomaterials; (2) cells are seeded using needles that can move in a spatially and temporally controlled user-defined manner with a 20 μm precision.

The 3D architecture in bioprinted tissue allows all the different cell types to mature simultaneously, thus increasing the likelihood of their working together like a native tissue. The engineered blood retina barrier contains a polarized RPE monolayer, and endothelial cells derived from the same iPS cell line. 3D microvessels derived from endothelial cells will be lined in a tissue containing choroidal fibroblasts and pericytes located underneath RPE cells. This in vitro tissue can be used as a human model for identifying molecular pathways in diseases of BRB, for discovering and testing drugs that affect BRB, and as a cell based therapy.

Example 1

Overview

The design of the bioprinted choroidal tissue is described with respect to determining its: 1) design structure (type of tissue, shape, thickness); 2) bio-ink; 3) cell concentration; 4) cellular composition of bio-ink; 5) printing substrate; 6) media composition; 7) volume of media; 8) frequency of media change; 9) total culture time; 10) printing; 11) visual, histological, and biochemical analysis. These elements are exemplified in FIGS. 1-14.

1) Design of structure: 3D engineered vascularized tissue is printed on a electrospun Poly(lactic-coglycolic) Acid (PLGA) scaffold. Printed geometry has been determined to facilitate qualitative/quantitative analysis of angiogenesis. Diameter of initial printed tissue was around 10 mm, which can be easily modified. 0.5-25 μm thickness of PLGA scaffold offers spaces for fibroblast to generate extracellular matrix (ECM) structure mimicking Bruch's membrane as well as mechanical support of the printed 3D vascularized tissue. RPE cells are seeded on the other side of the scaffold as a monolayer.

2) Bio-ink: An example of a bio-ink was developed using a natural hydrogel Fibrin mixed with a commercial hydrogel from Organovo (NOVOGEL® #2). NOVOGEL® #2 is a collagen-derived gel, which has similar characteristics to gelatin and can be replaced by any similar gel. NOVOGEL® #2 polymerizes at 4° C. and dissolves at 37° C. and because of this property it is not appropriate for vasculogenesis of embedded endothelial cells. A combination hydrogel was generated by combining NOVOGEL® #2 with fibrin gel, which has been used successfully for 3D vasculogenesis. Fibrin gel is generated by mixture of fibrinogen and thrombin, and addition of aprotinin reduces gel degradation by inhibiting enzyme reaction. Fibrin gel itself was not suitable for bioprinting due to fibrous characteristics and timely polymerization that hindered uniform distribution of embedded cells within printing gel.

A (2.5 mg/ml) solution in D-PBS (0.075 U of aprotinin/ml) was used since fibrinogen doesn't affect polymerization of NOVOGEL® #2 until thrombin is added. After printing encapsulated cells in gel mixture, growth media was added containing thrombin (0.5 U/ml), and the printed sample was incubated with media at room temperature for two hours, which provides time for polymerization of fibrinogen. As NOVOGEL® #2 degrades at 37° C., polymerized fibrin provides appropriate environment for vasculogenesis from embedded endothelial cells.

3 and 4) Cell concentration: Tissue density, coalescence, and health may vary with difference in concentration. Spheroidal co culture system experiments indicated that an optimum ratio of fibroblast and endothelial cells is 10:1. An exemplary protocol used endothelial cell concentration in a range of 5 million cells/ml, fibroblast concentration in a wide range of 10 million cells/ml, and pericyte concentration in about 0.5 million cells/ml.

5) Print substrate: Cells were printed on electro-spun PLGA scaffold, which were assembled in a multi-transwell platform. TRANSWELL is a registered trademark of Corning for a permeable support with a microporous membrane that permit the update and secrete molecules on both their basal and apical surfaces. These devices are described in detail in TRANSWELL® Permeable Supports Selection and Use Guide from Corning. The PLGA scaffold replaces the native permeable support of a commercially available TRANSWELL®, and provides a biocompatible and degradable scaffold consisting of fibers having diameters of several hundred nanometers. Prior to bioprinting, oxygen-plasma treatment was applied for 30 minutes on the surface of the PLGA scaffold to enhance adherence of printed cell-gel structure. Oxygen plasma coating improves the surface condition by changing the surface from hydrophobic to hydrophilic, and provided sterilization. The 3D inserts disclosed herein, see FIG. 3 can also be used for bioprinting.

6,7,8) Media components, change frequency, and volume: Each cell type often requires up to 5% fetal bovine serum. For the microvascular endothelial cells, endothelial cell media containing FGF, VEGF, IGF-1, hydrocortisone, heparin sulfate, (Lifeline cell technology, MD) was used. A supplement was required for iPSC derived endothelial cells (Cellular dynamics international, WI). 5% fetal bovine serum containing RPE medium was used for fibroblast culture as well. After printing, media is mixed at a 1:2 ratio for cell growth within printed fibrin gel. Media was changed to a thrombin free media after 24 hours, then every 48 hours for the remaining culture period 9) Culture time and RPE seeding: Vasculogenesis has been observed by 5 days after printing. The printed tissue was viable for at least a 9 week period. At day 7 after printing endothelial cells, RPE cells were seeded on the opposite face of the polymer scaffold. At two weeks after RPE seeding, prostaglandin was added for the maturation of the RPE monolayer. 4~9 weeks of culture time was used to maintain printed tissue. The tissue was viable for at least 9 weeks.

10) Visualization: GFP expressing primary endothelial cells were used for live tissue visualization, and an immunostaining technique was used to visualize iPSC derived RPE/endothelial cells and pericytes. A tissue sectioning technique was used to visualize a cross section of the BRB tissue followed by immunohistochemistry. Fluorescence is captured by a confocal microscope (Carl Zeiss, Germany).

An overall depiction of the method of making the bioengineered BRB is shown in FIG. 1A wherein pluripotent stem cells (iPSCs) were differentiated into endothelial cells, fibroblasts and pericytes. The cells were suspended in the hydrogel bio-ink and bioprinted on the first face of the PLGA scaffold. The cells were on that first face of the scaffold were cultured in a well while the scaffold was suspended from a Transwell holder with the bioprinted face toward the bottom of the well to produce a bioprinted choroid on the first face of the substrate. At day 7 after bioprinting, RPE cells were deposited on the opposite face of the substrate through the holder, and the RPE cells were cultured in a well on a Transwell holder that suspends the substrate. The end product is depicted schematically in an exploded view in FIG. 1A with the layers shown separated for clarity. An RPE monolayer is present on and adherent to the top face of an intermediate biodegradable scaffold layer, and a bottom layer of bioprinted choroid is shown adherent to the bottom face of the biodegradable scaffold.

Example 2

Exemplary Protocols

A flow chart showing the steps of an exemplary method is provided in FIG. 12. Individual steps of the method are illustrated schematically in FIGS. 1B-1H. This embodiment of the protocol includes the following steps:

The day before printing, scaffolds are assembled for printing. A desired printing frame (e.g. corning 3407 Snapwell plate or corning 3470 Transwell® plate, or customized 3D printed frame etc.) are selected. The SNAPWELL®/Transwell® membrane (shaded region 10 in FIG. 1B) is removed from the frame after disassembling the bottom half of the snapwell. Removal of the membrane leaves the cylindrical bottom portion of the transwell with an open end that forms a printing frame 12 (FIG. 1C). Alternatively, the 3D insert can be used, see FIG. 3.

A PLGA (or other biocompatible material) scaffold is obtained at the correct size using a biopsy punch on a thin PLGA sheet, and the punched-out scaffold is mounted on the printing frame. Silicone adhesive is used to attach the scaffold to the printing frame. A mixed adhesive is placed on the lid of a petri dish and the bottom of the printing frame 12 is coated in the adhesive to form an adhesive ring 14 (FIG. 1D). The scaffold 16 (FIG. 1E) is attached to the bottom of the adhesive-coated frame and allowed to dry for 5 minutes. After the adhesive is set, the bottom half of the Snapwell is reattached to the frustoconical funnel body 18 of the holder as shown in FIG. 1F (this step is not needed if using a Transwell). If using Snapwells, add adhesive to a sterile O-ring made of Teflon (or comparable substitute) and set the O-ring inside the bottom opening of the snapwell so that it is flush and watertight with the scaffold.

The illustrated scaffold 16 is a thin, substantially flat substrate having opposite parallel first and second surfaces. Cells can be printed on both surfaces of the scaffold or just one. For ease of description, the surface that is exposed at the bottom of the well will be referred to as the bottom surface and the opposite surface to which the printing frame is attached will be referred to as the top surface of the substrate. In the disclosed embodiment, only one surface of the scaffold (the bottom surface) is used for printing and the other surface (the top surface) is used for seeding cells such as epithelial cells. The non-printing or top surface of substrate 16 is coated with an ECM solution such as vitronectin, fibronectin, or any other cell attachment factors. Substrate 16 is incubated overnight (1 hour at room temperature, and 1-12 hours in an incubator to remove wrinkles from thinner scaffolds). Water is removed from the printing apparatus which is then stored in sterile conditions until it is time to print.

On the day of printing, all required media and trypsin are thawed, and the printing scaffolds are inspected to confirm they have no tears. Vials of bio-ink (cells+hydrogel) and thrombin aliquots are prepared. A relatively dilute solution of Fibrinogen (2.5~20 mg/mL) is prepared, and stored in a water bath until Fibrinogen dissolves. Another more concentrated solution of fibrinogen is prepared (for example, at least double the concentration as compared to the dilute solution; other ECMs like collagen can also be mixed in the dilute fibrinogen). Once both fibrinogen solutions are completely in suspension, aprotinin/tranexamic acid/aminocaproic acid is added to both tubes, mixed well, filtered and then stored in a water bath. Aprotinin concentration is 0.05~0.3 U/ml. One tube of Novogel #2 (Organovo, Calif.) or Gelatin (60 mg~200 mg/ml) is added to the dilute solution of fibrinogen and incubated for an additional 30 minutes Store at 4° C. until ready to print.

Growth media (30-50 mL) is prepared, including thrombin (0.5 U-10 U/ml). The printing scaffold 16 is completely dried and subjected to oxygen-plasma treatment for 20-60 minutes. The plasma treatment sterilizes the scaffold and makes it hydrophilic so that bio-ink can adhere better to the surface.

A cell mixture is prepared by passaging and counting cells, and if multiple cell types are used, establishing ratios (ranges such as: endothelial cells: 5-30 million cells/ml, Fibroblasts: 10-50 million cells/ml, Pericytes: 0.5-3 million cells/ml). The cell mixture is loaded in a tube designated for the bio-ink, then centrifuged at 500 G for 4 minutes to spin it down. Once the supernatant has been removed, the fibrin gel is added and the pellet disturbed. Once suspended, the bio-ink is quickly loaded into the printing syringe, ensuring that no bubbles float to the plunger, and stored for 10-15 minutes at 4 degrees C.

The substrate 16 that is adhered to the printing frame is then exposed to the printer by inverting the funnel 18 (FIG. 1G) so that the funnel rests on a support with the printing surface ("bottom surface") of substrate 16 facing upward and exposed for printing. The printer is started by turning the hood power on, pressing the reset button, flipping the switch on the power source, and then powering on the keyboard. After spraying the work area, the syringe is loaded, the plunger depressed to remove air bubbles, and the dispense position fixed. This is accomplished by using the directional arrows to manipulate the x,y, and z coordinates of the bioprinter needle. Once the x and y coordinates are set, the printing needle(s) is lowered until it barely disturbs the scaffold. After selecting the script (script is written separately and it dictates the printing syringe movement) the bioprinter begins to print. After printing is complete, 3-5 minutes are allowed to elapse. Then 360 uL of the denser fibrin/collagen gel/Matrigel with or without cell inclusion is added to the top layer of the print, and it is allowed to polymerize for 20 minutes. Then 4 mL of the prepped media is added to each well and allowed 2 hours to incubate at room temperature before placing the gels in the 37 degree C. incubator.

RPE Seeding Protocol

The funnel 18 is reoriented as shown in FIG. 1H, suspended in a well 20 of a multiwell plate with the funnel 18 at the top of well 20 and substrate 16 positioned with its already-printed surface down, with the printed surface adjacent or against the bottom surface of well 20. The previously printed choroid is on the bioprinted (bottom) face of substrate 16.

Seven days after the printing step, RPE cells are trypsinized by adding 3 ml of disassociation reagent (TrypLE or 0.25% Trypsin) to each well, and incubated at 37 degrees C. for 30-40 minutes. If necessary, a cell scraper is used to gently remove any cells that are not dislodged. After incubation, 2-3 mLs of RPE media are added to the wells and the contents transferred to the 50 mL tube. The tube is centrifuged at 1000 rpm for 5 minutes to collect a pellet. RPE monolayer readily clumps, thus mixing with a syringe and long needle and cell strainer can enhance breaking clumped cells.

The RPE cell suspension is added to the top of scaffold 16 through funnel 18 to the non-printed face of the scaffold. After seeding, 500 uL of RPE media is added to the top of the well (Transwell), and 3-5 mL's to the basal side of the Transwell. Media is changed every other day. This procedure is repeated until a monolayer has formed. The previously printed choroid remains on the bottom face of substrate 16 in FIG. 1H, with 200-400 K RPE cells per 1 cm diameter of circular area on the top face of substrate 16.

Example 3

Exemplary Reagents

| Hydrogel (Bio-ink) | |
| --- | --- |
| Current bio-ink | Potential alternative |
| Novogel#2 | Gelatin/collagen derived gel, Gelatin methacryloyl (GelMA) |
| Fibrin gel | Collagen type I, Matrigel, Alginate/polysaccharide derived gel, Laminin, Pura Matrix |

| Scaffold (bioprinting substrate) | |
| --- | --- |
| Current material | Potential alternative |
| POLY (D,L-LACTIDE-CO-GLYCOLIDE) (PDLGA) | PLGA or poly(lactic-co-glycolic acid), PLA or Poly(lactic acid), Silk, fibroin, Any biogegradable materials can be applied. |

RPE media with 5% FBS
MEM-alpha modified medium (Sigma-Aldrich) is used as the base medium to prepare 5% serum containing media for culturing of RPE cells (RPE medium; Table 1 below).

| Name | Amount | Potential alternative |
| --- | --- | --- |
| MEM, alpha modification | 500 mL | Any basal media |
| N1 supplement | 5 mL | Any neural cell growth media supplement |
| Penicillin-streptomycin | 5 mL | Gentamycin, amphotericin, Penicillin Streptomycin, or any antibiotics |
| GlutaMax - I | 5 mL | L-glutamine |
| Non essential amino acids | 5 mL | Any supplement including alanine, arginine, asparagine, aspartic acid, cysteine, glutamic acid, glutamine, glycine, proline, serine, and tyrosine |
| THT* | | |
| Taurine | 125 mg | |
| Hydrocortisone | 10 μg | |
| Triiodo-thyronin | 0.0065 μg | |
| Fetal bovine serum** | 5% | Hyclone FBS, another serum type can be 2~10% |

*THT is made by dissolving taurine-hydrocortisone-triiodo-thyronin in 1 1.5 mL PBS before making the medium.
Multiple aliquots are made and stored at −80° C. to simplify culturing preparation of the culture medium.
Fetal bovine serum used in media preparation is obtained from Atlanta Biologicals (Norcross, GA). Each bottle of the serum is heat inactivated (56° C. for 1 hr) prior to use.

| Primary/iPSC derived endothelial cell media (10% FBS) | | |
| --- | --- | --- |
| Name | Amount | Potential alternatives |
| VascuLife Basal Media | 500 mL | DMEM, MEM, or can be any basal media |
| iCell Endothelial cells: Medium Supplement* | 50 mL | |
| Rh VEGF | 500 uL | Ephrin, VEGF A, B, C, and E. VEGF 121~206, Placenta growth factor (PlGF) |
| Rh IGF-1 | 500 uL | Insulin, IGF-1, IGF-2 |
| Rh FGF-b | 500 uL | FGF-acidic, Heparin-binding growth factor (HBGF)-5 and 6, keratinocyte growth factor (KGF), Androgen-induced growth factor (AIGF), glia-activating factor(GAF), fibroblast growth factor homologous factor(FHF) |
| Ascorbic Acid | 500 uL | |
| Rh EGF | 500 uL | UniProtKB - L8EC91 (L8EC91_HUMAN), TGF-alpha, Amphiregulain, HB-EGF, b-Cellulin, Epiregulin, Epigen, NRG-1/2/3/4, Caleb, |
| Heparin sulfate | 500 uL | |
| L-Glutamine | 500 uL | |
| Hydrocortisone | 500 uL | |
| Antibiotics | | Gentamycin, amphotericin, Penicillin Streptomycin, or any antibiotics |

*Cell supplement contains FBS, final FBS concentration is 10%

| Tissue Culture Media for printed choroid after printing | | | |
| --- | --- | --- | --- |
| Name | Amount | Final Concentration | Potential alternative factors |
| RPE media with 5% FBS | 100 mL | Na | |
| Endothelial cell media | 50 mL | Na | |
| Recombinant Human Vascular endothelial | 250 uL | 85 ng/mL, 5 ng/mL 0 ng/mL* | Ephrin, VEGF A, B, C, and E. VEGF 121~206, Placenta growth factor (PlGF) |

-continued

Tissue Culture Media for printed choroid after printing

| Name | Amount | Final Concentration | Potential alternative factors |
|---|---|---|---|
| growth factor (VEGF) 165 Protein | | | |
| Angiopoietin 1 | 1500 uL | 100 ng/mL, 0 ng/mL** | Platelet-derived growth factor (PDGF), Sphingosine-1-phosphate (S1P), Notch, Transforming growth factor beta (TGFβ), CXCL12 |
| Aprotinin | 600 uL | 0.075 U/mL, 0 U/mL*** | Tranexamic acid, Aminocaproic acid |
| Fetal Bovine Serum | 2500 uL | 5% Final Concentration | Can be 2~10% |

*Depends on phase of tissue culture, but the concentration scales down with time
**Depends on phase of tissue culture, but the concentration scales down with time
***Depends on phase of tissue culture, but the concentration scales down with time Example 4

Results in the Ocular Tissue Model

The results presented in FIGS. 13A-13B show the redefined geometry of bioprinting in XY plane enables separation of vascular development into angiogenesis dominant (gaps) and vasculogenesis dominant (printed region) regions. The quantification of angiogenesis in gaps validated the printed microvascular network by showing that angiogenesis significantly depended on concentration of vascular endothelial growth factors (VEGF). A week of VEGF treatment significantly enhanced growth and viability of microvascular network. Histological cut of cross section of the tissues show the hollow tube formation of endothelial cells surrounded by pericyte (colocalization of two markers), which resembles in vivo. This system can be used as a disease model, see FIGS. 17, 18. In one example, the cells are derived from iPSC.

FIGS. 15A-15C shows a prototype of engineered outer blood retina barrier. FIG. 15A shows complete formation of RPE monolayer on one side of PLGA scaffold. FIG. 15B shows fully vascularized tissue, a choroid, printed on the other side of the scaffold. FIG. 15C, panel 1 and 15 C, panel 2 shows that Ezrin expression in apical region of RPE confirms polarity of RPE. 15C, panel 3 shows overall 3D image reconstructed from confocal images. The results shown in FIGS. 15A-15C confirm that 3D structure of the engineered tissue mimics a native choroid.

FIG. 16 shows comparative studies between tissue with and without RPE on the scaffold. Tissue with RPE exhibit thicker diameter of microvessel (FIG. 16D vs. FIG. 16F; CD31) and stronger expression of fenestration marker (FIG. 16D vs. FIG. 16F and FIG. 16E vs. FIG. 16G; FELS) than tissue without RPE. Inclusion of RPE also induced significant amount of vessel growth and maintained vessel viability (FIG. 16E vs. FIG. 16G; CD31). TEM data (FIG. 16H) shows strong pigmentation and apical processing (arrows). TEM data of the microvessel confirmed the ultrastructure of fenestration (arrow heads), which is a special feature of choriocapillaris. Hence, the results confirmed that there was significant roles of RPE on the viability and functions of choroid, which is similar to the choroid in vivo.

STAT3 overexpression was previously reported in wet AMD. It was tested if STAT3 expression in RPE plays a role in "choroidal" neovascularization using the present methods and model system (see FIG. 17). STAT3 overexpressed iPSC derived RPE and patient who has STAT3 gene mutation specific iPSC derived RPE were used on a "healthy choroid". The RPE monolayer did not show noticeable changes, but STAT3 overexpression of RPE significantly induced vascularization in subRPE region (FIG. 17D vs. FIG. 17F). STAT3 mutation of RPE appeared to destabilize vascular structure (FIG. 17G vs. FIG. 17H). Thus, FIG. 17 provides an example of disease model using gene modified iPSCs and patient specific iPSCs.

It was tested if hypoxic condition of RPE or RPE-"choroid" plays a role in "choroidal" neovascularization. Hypoxia has been reported as a crucial factor to induce wet AMD. A chemical compound, DMOG, was used to induce hypoxia-inducible factor in RPE or every cell type within the tissue. The RPE monolayer did not show noticeable changes, but DMOG treatment of either RPE only or both RPE and "choroid" significantly induced vascularization in sub-RPE region (FIG. 18D to FIG. 18F). Thus, FIG. 18 shows an example of a disease model produced using a chemical inducer of molecular targets.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. A method of fabricating a three-dimensional engineered blood retinal barrier (BRB) comprising a choroid and retinal pigmented epithelial cells, the method comprising:
 a) depositing a first bio-ink comprising a hydrogel and a first medium, wherein the hydrogel comprises endothelial cells, onto a biocompatible scaffold comprising first and second opposite surfaces, such that the hydrogel adheres to a first surface of the biocompatible scaffold;
 b) maturing the deposited first bio-ink on the first surface of the biocompatible scaffold in a second medium for at least four days to allow the endothelial cells to form vessels;
 c) depositing retinal pigment epithelial cells in a third medium to form a single cell layer on the second surface of the biocompatible scaffold, such that the biocompatible scaffold is between the endothelial cells and the retinal pigment epithelial cells; and
 d) culturing the deposited retinal pigment epithelial cells in the third medium on the biocompatible scaffold so that they proliferate and mature,
 thereby forming the three-dimensional engineered BRB with an artificial choroid on the first surface and an artificial retinal pigment epithelium on the second surface.

2. The method of claim 1, wherein the biocompatible scaffold comprises poly (D, L-lactide co-glycolide (PDGLA), poly(lactic-co-glycolic acid) (PLGA), poly(lactic acid) (PLA), poly(-L-lactic acid) (PLLA), poly (glycolic) acid (PGA), poly caprolactone (PCL), poly ethylene glycol (PEG), silk, fibroin, collagen, or a combination thereof.

3. The method of claim 1, wherein the biocompatible scaffold comprises poly (D, L-lactide co-glycolide (PDGLA).

4. The method of claim 1, wherein the biocompatible scaffold consists of cross-linked poly (D, L-lactide co-glycolide (PDGLA).

5. The method of claim 3, wherein the poly (D, L-lactide co-glycolide) (PDGLA) is treated with oxygen plasma prior to depositing the first bio-ink.

6. The method of claim 5, wherein the poly (D, L-lactide co-glycolide) (PDGLA) is treated with the oxygen plasma for less than one day prior to depositing the first bio-ink.

7. The method of claim 1, wherein the first bio-ink further comprises fibroblasts and/or pericytes.

8. The method of claim 7, wherein the first bio-ink comprises about 5 to about 30 million endothelial cells per milliliter, about 10 to about 50 million fibroblasts per milliliter, and about 0.5 to about 3 million pericytes per milliliter.

9. The method of claim 7, wherein the endothelial cells, fibroblasts and pericytes are present in the first bio-ink at a ratio of 1:0.3:0.1 to 1:10:1, respectively.

10. The method of claim 9, wherein the endothelial cells, fibroblasts and pericytes are present in the first bio-ink at a ratio of 1:2:0.5, respectively.

11. The method of claim 7, wherein the retinal pigment epithelial cells, endothelial cells, fibroblasts and/or pericytes are produced from induced pluripotent stem cells.

12. The method of claim 7, wherein the endothelial cells, fibroblasts, pericytes, and retinal pigment epithelial cells are human cells.

13. The method of claim 1, wherein the first bio-ink is deposited by bioprinting, the bioprinting comprising extrusion of the bio-ink onto the biocompatible scaffold.

14. The method of claim 1, wherein the hydrogel in the first bio-ink comprises a collagen based hydrogel.

15. The method of claim 1, wherein the hydrogel in the first bio-ink comprises a gelatin hydrogel, a collagen hydrogel, a fibrin hydrogel, a polysaccharide hydrogel, an alginate hydrogel, a laminin hydrogel, a fibronectin hydrogel, a laminin hydrogel, a vitronectin hydrogel, a polyethylene glycol hydrogel, a gelatin methacryloyl hydrogel, or a combination thereof.

16. The method of claim 1, wherein the first and second media comprise vascular endothelial cell growth factor (VEGF), angiopoietin 1, insulin-like growth factor (IGF), epithelial growth factor (EGF), fibroblast growth factor (FGF), ascorbic acid, hydrocortisone, heparin sulfate, angiopoietin, and aprotinin.

17. The method of claim 16, wherein the first medium comprises 1-1,000 ng/ml of VEGF, 50-1000 ng/ml of angiopoietin 1, and 0.075-0.5 U/ml of aprotinin.

18. The method of claim 1, further comprising coating the second surface of the biocompatible matrix with an extracellular matrix prior to depositing the retinal pigment epithelial cells onto the second surface of the biocompatible scaffold.

19. The method of claim 18, wherein the extracellular matrix comprises collagen, laminin, gelatin, chondroitin sulfate, proteoglycans, elastin, hyaluronic acid, vitronectin and/or fibronectin or a combination thereof.

20. The method of claim 1, wherein depositing the retinal pigment epithelial cells comprises adding a suspension of retinal pigment epithelial cells to the second surface of the biocompatible scaffold.

21. The method of claim 1, wherein the retinal pigment cells are cultured in the third medium until a monolayer is formed.

22. The method of claim 1, wherein the retinal pigment epithelial cells are deposited onto the second surface of the biocompatible scaffold at five or more days following bioprinting the first bio-ink onto the first surface of the biocompatible scaffold.

23. The method of claim 22, comprising depositing 100,000 to 400,000 retinal pigment epithelial cells per 1 centimeter of the surface of the biocompatible scaffold.

24. The method of claim 1, wherein depositing the retinal pigment epithelial cells comprises depositing a second bio-ink comprising retinal pigment epithelial cells and the third medium.

25. The method of claim 24, wherein the second bio-ink comprises a hydrogel, and wherein the hydrogel in the second bio-ink comprise a gelatin hydrogel, a collagen hydrogel, a fibrin hydrogel, a polysaccharide hydrogel, an alignate hydrogel, a laminin hydrogel, a fibronectin hydrogel, a laminin hydrogel, a vitronectin hydrogel, a polyethylene glycol hydrogel, or a gelatin methacryloyl hydrogel.

26. The method of claim 1, wherein the endothelial cells and the retinal pigment epithelial cells are human cells.

27. The method of claim 1, further comprising transplanting the three-dimensional engineered BRB comprising the choroid and retinal pigment epithelial cells into the eye of a subject.

28. The method of claim 27, wherein the subject has acute macular degeneration.

29. A method of fabricating a three-dimensional engineered blood retinal barrier (BRB) comprising a choroid and retinal pigment epithelial cells, the method comprising:
  a) depositing a first bio-ink comprising endothelial cells, fibroblasts and pericytes in a collagen and fibrinogen hydrogel and a first medium comprising thrombin, vascular endothelial grown factor, epithelial growth factor (EGF), fibroblast growth factor (FGF), insulin-like growth factor (IGF), ascorbic acid, hydrocortisone, heparin sulfate, angiopoietin-1 and aprotinin, onto a biocompatible oxygen plasma treated poly (D, L-lactide co-glycolide) PDGLA scaffold, such that the endothelial cells, fibroblasts and periyctes adhere to a first surface of the biocompatible scaffold;
  b) maturing the deposited first bio-ink in a second medium comprising an effective amount of vascular endothelial grown factor, EGF, FGF, IGF, ascorbic acid, hydrocortisone, heparin sulfate, angiopoietin-1 and aprotinin, in the absence of thrombin, for at least four days to allow the endothelial cells to form vessels;
  c) depositing retinal pigment epithelial cells in a third medium to form a layer on a second surface of the biocompatible scaffold, wherein the first and the second surface of the biocompatible scaffold are opposite surfaces, such that biocompatible scaffold is between the endothelial cells and the retinal pigment epithelial cells, and wherein the second surface is coated with vitronectin, and wherein the third medium comprises an effective amount of taurine-hydrocortisone-triiodo-thyronin, hydrocortisone, Triiodo-thyronin, and fetal bovine serum;
  d) culturing the deposited retinal pigment epithelial cells in the third medium comprising the effective amount of taurine-hydrocortisone-triiodo-thyronin, hydrocortisone, triiodo-thyronin, and fetal bovine serum so that the deposited retinal pigment epithelial cells proliferate and mature; and
  e) culturing the endothelial cells, fibroblasts and the pericytes in a fourth medium comprising an effective amount of vascular endothelial growth factor, wherein the fourth medium does not comprise thrombin and angiopoietin-1, thereby producing a microvascular network;
  thereby forming the three three-dimensional engineered BRB.

30. A method of determining the effect of a test agent on a BRB, the method comprising:
- contacting a three-dimensional engineered BRB comprising a choroid and retinal pigmented epithelial cells produced by the method of claim 1 with a test agent; and
- evaluating i) a phenotype of cells within the choroid and retinal pigment epithelial cells, and/or ii) three-dimensional structure of the choroid and retinal pigment epithelial cells,
- wherein a change in i) the phenotype of the cells or ii) the three-dimensional structure of the choroid and retinal pigment epithelial cells, respectively, indicates that the agent has an effect on the BRB.

* * * * *